US011993662B2

(12) United States Patent
Chu et al.

(10) Patent No.: US 11,993,662 B2
(45) Date of Patent: May 28, 2024

(54) GENERAL SEQUENCE OF CHIMERIC ANTIGEN RECEPTOR, CHIMERIC ANTIGEN RECEPTOR AND AN APPLICATION THEREOF

(71) Applicant: Fudan University, Shanghai (CN)

(72) Inventors: Yiwei Chu, Shanghai (CN); Yuedi Wang, Shanghai (CN); Feifei Luo, Shanghai (CN)

(73) Assignee: Fudan University, Shanghai (CN)

( * ) Notice: Subject to any disclaimer, the term of this patent is extended or adjusted under 35 U.S.C. 154(b) by 868 days.

(21) Appl. No.: 17/027,856

(22) Filed: Sep. 22, 2020

(65) Prior Publication Data

US 2021/0101995 A1    Apr. 8, 2021

Related U.S. Application Data

(63) Continuation of application No. PCT/CN2019/107030, filed on Sep. 20, 2019.

(30) Foreign Application Priority Data

Aug. 6, 2019  (CN) .......................... 201910720495.8

(51) Int. Cl.
  *C07K 16/32*  (2006.01)
  *C07K 16/28*  (2006.01)
  *C07K 16/30*  (2006.01)

(52) U.S. Cl.
  CPC .......... *C07K 16/32* (2013.01); *C07K 16/2803* (2013.01); *C07K 16/303* (2013.01); *C07K 2317/53* (2013.01); *C07K 2317/622* (2013.01)

(58) Field of Classification Search
  CPC .. C07K 16/32; C07K 16/2803; C07K 16/303; C07K 2317/53; C07K 2317/622; A61K 39/0011; A61P 35/00
  See application file for complete search history.

(56) References Cited

U.S. PATENT DOCUMENTS 8,669,350 B2    3/2014  Chou et al.

FOREIGN PATENT DOCUMENTS

| CN | 106459206 A | 2/2017 |
|---|---|---|
| CN | 107849112 A | 3/2018 |
| CN | 108017717 A | 5/2018 |
| CN | 108239144 A | 7/2018 |
| CN | 108271377 A | 7/2018 |
| CN | 108602887 A | 9/2018 |
| CN | 109562126 A | 4/2019 |
| CN | 110078817 A | 8/2019 |
| WO | WO-2019133969 A2 | 7/2019 |
| WO | WO-2019140127 A2 | 7/2019 |

OTHER PUBLICATIONS

Richter, C., Differential responsiveness of Tumour Necrosis Factor Receptors (TNFR) type 1 and 2—the critical role of the TNFR stalk region PhD Thesis, New Castle University, dated Jul. 31, 2011.

*Primary Examiner* — Nelson B Moseley, II
*Assistant Examiner* — Alyssa Rae Stonebraker
(74) *Attorney, Agent, or Firm* — Harness, Dickey & Pierce, P.L.C.

(57) ABSTRACT

The present invention provides a general sequence of chimeric antigen receptor (CAR) and an application thereof, The hinge domain in the general sequence includes hinge domain V-5, hinge domain V-4-5, hinge domain V-3-4-5, hinge domain V-2-3-4-5 or hinge domain V-1-2-3-4-5. The CAR constructed by using the general sequence of the chimeric antigen receptor of the present invention can significantly improve the antigen-specific immune response of CAR-T cells, enhance the sensitivity of CAR-T cells and resist exhaustion, so as to enhance the therapeutic effect of CAR-T cells and enhance the therapeutic effect of antitumor agents. At the same time, the CAR containing the general sequence of the present invention is suitable for transfection of immune cells such as T cells and NK cells, and can be broadly applied to tumor therapy.

3 Claims, 27 Drawing Sheets

Specification includes a Sequence Listing.

GENERAL SEQUENCE OF CHIMERIC ANTIGEN RECEPTOR, CHIMERIC ANTIGEN RECEPTOR AND AN APPLICATION THEREOF

CROSS REFERENCE TO RELATED APPLICATIONS

This application is a continuation of International Application PCT/CN2019/107030, filed Sep. 20, 2019 which claims the priority of Chinese Patent Application No. 201910720495.8, entitled "Five hinge domains and chimeric antigen receptors thereof and immune cells", filed with China National Intellectual Property Administration on Aug. 6, 2019, which is incorporated herein by reference in its entirety.

FIELD

The invention relates to the field of biomedical technology, in particular to a hinge domain-optimized general sequence of chimeric antigen receptor (CAR), chimeric antigen receptor and an application thereof.

BACKGROUND

The preparation processing of Chimeric Antigen Receptor (CAR) is an editing method that using genetic engineering to connect scFv, which is non-MHC restricted to recognize target antigen, with hinge domain (hinge), transmembrane domain (TM) and T cell activation related motif. Immune cells such as T cells or NK cells are genetically modified to express CARs via electroporation, viral infection, etc., so that they have the ability to recognize and kill tumor cells. T cells modified with CARs have achieved positive effects in the treatment of hematological tumors. In 2017, two CAR-T cell products targeting CD19 were approved in the United States for the treatment of relapsed or refractory children and young adults with acute lymphoblastic leukemia. However, the development of the preparation of CAR is slow. T cells modified by CARs were first used to cure ovarian tumors in 1993. Over the past 20 years, CAR has developed from the first generation to the third generation, and in recent years, a series of technical optimization based on the second and third generation CARs has limited the overall effect. In the treatment of non-solid tumors, there are still difficulties such as treatment resistance or repeated recurrence; the significant and effective reports on solid tumor treatment are even seldom published. Therefore, it is urgent to develop a new generation CARs to improve the overall effect of tumor treatment.

At present, the widely used CAR mainly consists of four parts: 1. an outermost monoclonal single chain antibody sequence, which mainly recognizes antigens and determines the targeting of CAR-T cells; 2. a hinge domain, which connects the monoclonal antibody sequence and transmembrane sequence; 3. a transmembrane sequence, which enables CAR to anchor on the membrane of immune cells; and 4. an intracellular signal transmission sequence, which is mainly one or more intracellular segments of costimulatory molecules and CD3ζ chain in series, which provides CAR-T cells with the first and second signals required for activation. Therefore, after a comprehensive analysis of the above four parts of structure and function, recent studies have focused on the sequence optimization of scFv and intracellular signal segments in order to enhance the killing ability of CAR-T cells in vivo. However, up to now, there are no reports that CAR-T cells can significantly improve the curative effect. Although the hinge domain is an important part of CAR, there is no research on the function of the hinge domain in CAR-T cells because the hinge domain is traditionally considered to only connect the monoclonal antibody sequence and transmembrane sequence.

SUMMARY

The invention aims to provide a general sequence of a chimeric antigen receptor and a chimeric antigen receptor and an application thereof, so as to enhance the antigen-specific immune response of immune cells.

In order to realize the purpose of the application, the following technical schemes are provided:

The application provides a general sequence of chimeric antigen receptor, wherein the hinge domain includes hinge domain V-5, hinge domain V-4-5, hinge domain V-3-4-5, hinge domain V-2-3-4-5 or hinge domain V-1-2-3-4-5.

The nucleotide sequence of the hinge domain V-5 is set forth in SEQ ID NO.1.

The nucleotide sequence of the hinge domain V-4-5 is set forth in SEQ ID NO.2.

The nucleotide sequence of the hinge domain V-3-4-5 is set forth in SEQ ID NO.3.

The nucleotide sequence of the hinge domain V-2-3-4-5 is set forth in SEQ ID NO.4.

The nucleotide sequence of the hinge domain V-1-2-3-4-5 is set forth in SEQ ID NO.5.

The nucleotide sequence of a general sequence including hinge domain V-5 is set forth in SEQ ID NO.6.

The nucleotide sequence of a general sequence including hinge domain V-4-5 is set forth in SEQ ID NO.7.

The nucleotide sequence of a general sequence including the hinge domain V-3-4-5 is set forth in SEQ ID NO.8.

The nucleotide sequence of a general sequence including the hinge domain V-2-3-4-5 is set forth in SEQ ID NO.9.

The nucleotide sequence of a general sequence including the hinge domain V-1-2-3-4-5 is set forth in SEQ ID NO.10.

The application also provides a chimeric antigen receptor including the general sequences of the above schemes, the chimeric antigen receptor is obtained by connecting a single chain antibody and the general sequence in series; the single chain antibody includes HER2, CD19 or GPC3.

In the case that the single chain antibody is HER2, the chimeric antigen receptors includes HER2-V 5, HER2-V 4-5, HER2-V 3-4-5, HER2-V 2-3-4-5 and HER2-V 1-2-3-4-5.

The nucleotide sequence of HER2-V 5 is set forth in SEQ ID NO.11.

The nucleotide sequence of HER2-V 4-5 is set forth in SEQ ID NO.12.

The nucleotide sequence of HER2-V 3-4-5 is set forth in SEQ ID NO.13.

The nucleotide sequence of HER2-V 2-3-4-5 is set forth in SEQ ID NO.14.

The nucleotide sequence of HER2-V 1-2-3-4-5 is set forth in SEQ ID NO.15.

In the case that the single chain antibody is CD19, the chimeric antigen receptors includes CD19-V 5, CD19-V 4-5, CD19-V 3-4-5, CD19-V 2-3-4-5 and CD19-V 1-2-3-4-5.

The nucleotide sequence of CD19-V 5 is set forth in SEQ ID NO.16.

The nucleotide sequence of CD19-V 4-5 is set forth in SEQ ID NO.17.

The nucleotide sequence of CD19-V 3-4-5 is set forth in SEQ ID NO.18.

The nucleotide sequence of CD19-V 2-3-4-5 is set forth in SEQ ID NO.19.

The nucleotide sequence of CD19-V 1-2-3-4-5 is set forth in SEQ ID NO.20.

In the case that the single chain antibody is GPC3, the chimeric antigen receptors includes GPC3-V 5, GPC3-V 4-5, GPC3-V 3-4-5, GPC3-V 2-3-4-5 and GPC3-V 1-2-3-4-5.

The nucleotide sequence of GPC3-V 5 is set forth in SEQ ID NO.21.

The nucleotide sequence of GPC3-V 4-5 is set forth in SEQ ID NO.22.

The nucleotide sequence of GPC3-V 3-4-5 is set forth in SEQ ID NO.23.

The nucleotide sequence of GPC3-V 2-3-4-5 is set forth in SEQ ID NO.24.

The nucleotide sequence of GPC3-V 1-2-3-4-5 is set forth in SEQ ID NO.25.

The application further provides a drug that improves the antigen-specific immune response and promotes an anti-tumor effect, wherein the active components of the drug include the general sequences of the chimeric antigen receptor of the above schemes.

Beneficial effect of the application: the application provides a general sequence of chimeric antigen receptors comprising a hinge domain selected from the group consisting of hinge domain V-5, hinge domain V-4-5, hinge domain V-3-4-5, hinge domain V-2-3-4-5 and hinge domain V-1-2-3-4-5.

The nucleotide sequence of the hinge domain V-5 is set forth in SEQ ID NO.1; the nucleotide sequence of the hinge domain V-4-5 is set forth in SEQ ID NO.2; the nucleotide sequence of the hinge domain V-3-4-5 is set forth in SEQ ID NO.3; the nucleotide sequence of the hinge domain V-2-3-4-5 is set forth in SEQ ID NO.4; the nucleotide sequence of the hinge domain V-1-2-3-4-5 is set forth in SEQ ID NO.5. Compared with the chimeric antigen receptors using a traditional hinge domain, the chimeric antigen receptor (CAR) constructed by using the hinge domain-optimized general sequences of the chimeric antigen receptor of the present application can significantly improve the antigen-specific immune response of CAR-T cells, enhance the sensitivity of CAR-T cells and resist exhaustion, so as to enhance the therapeutic effect of CAR-T cells and enhance the therapeutic effect of anti-tumor agent. At the same time, the chimeric antigen receptor including the general sequences of the present application is suitable for transfection of immune cells such as T cells and NK cells, and can be broadly applied to tumor therapy.

DRAWINGS

Figure 15:
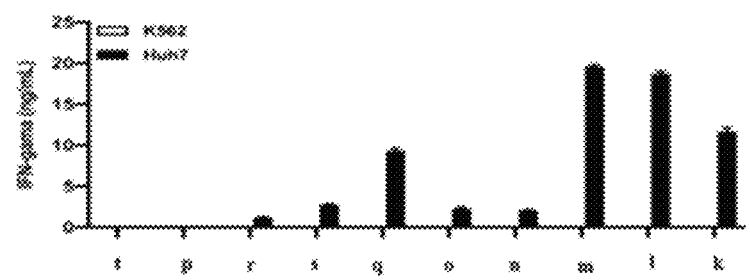
Figure 14A:
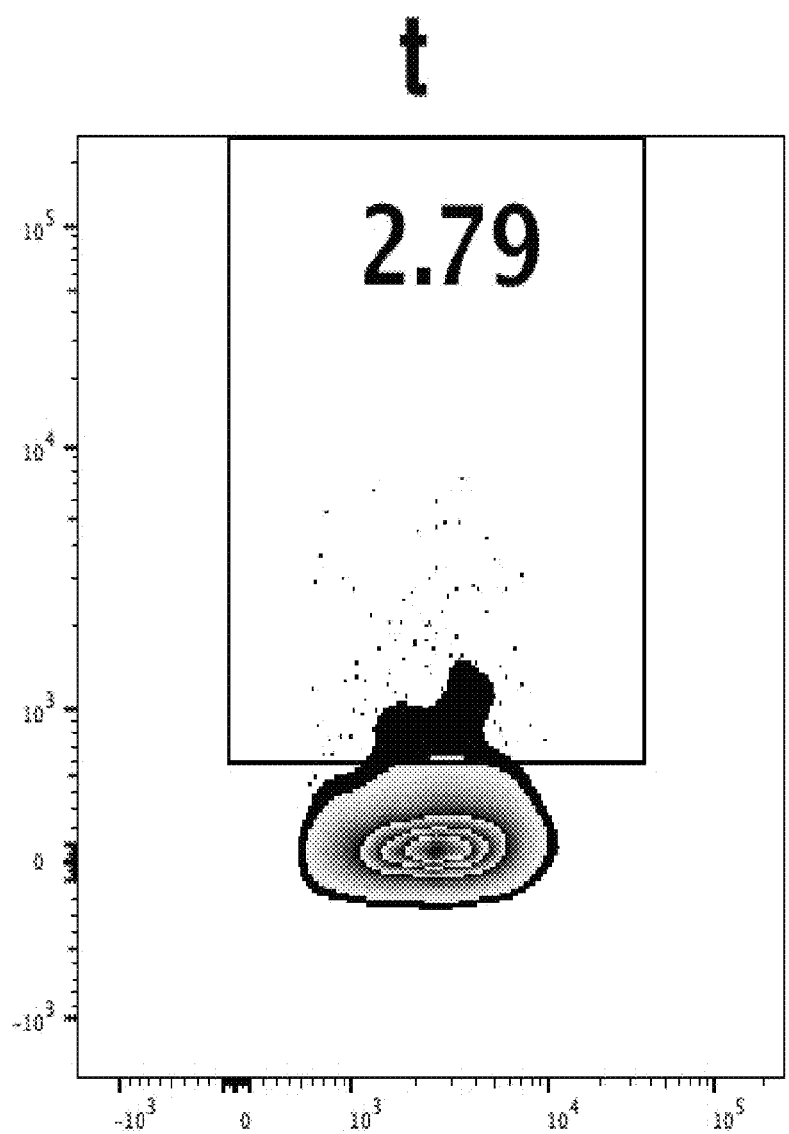
Figure 14B:
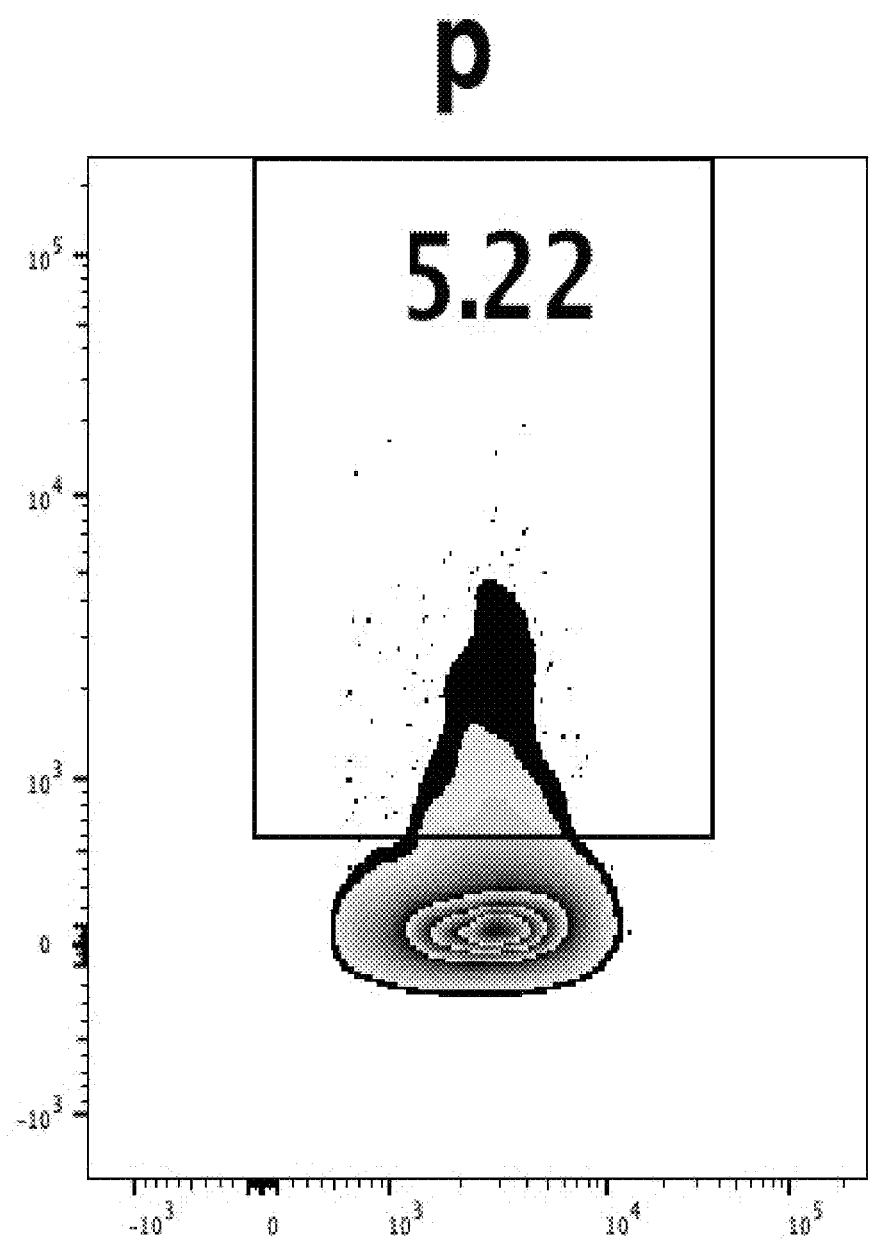
Figure 14C:
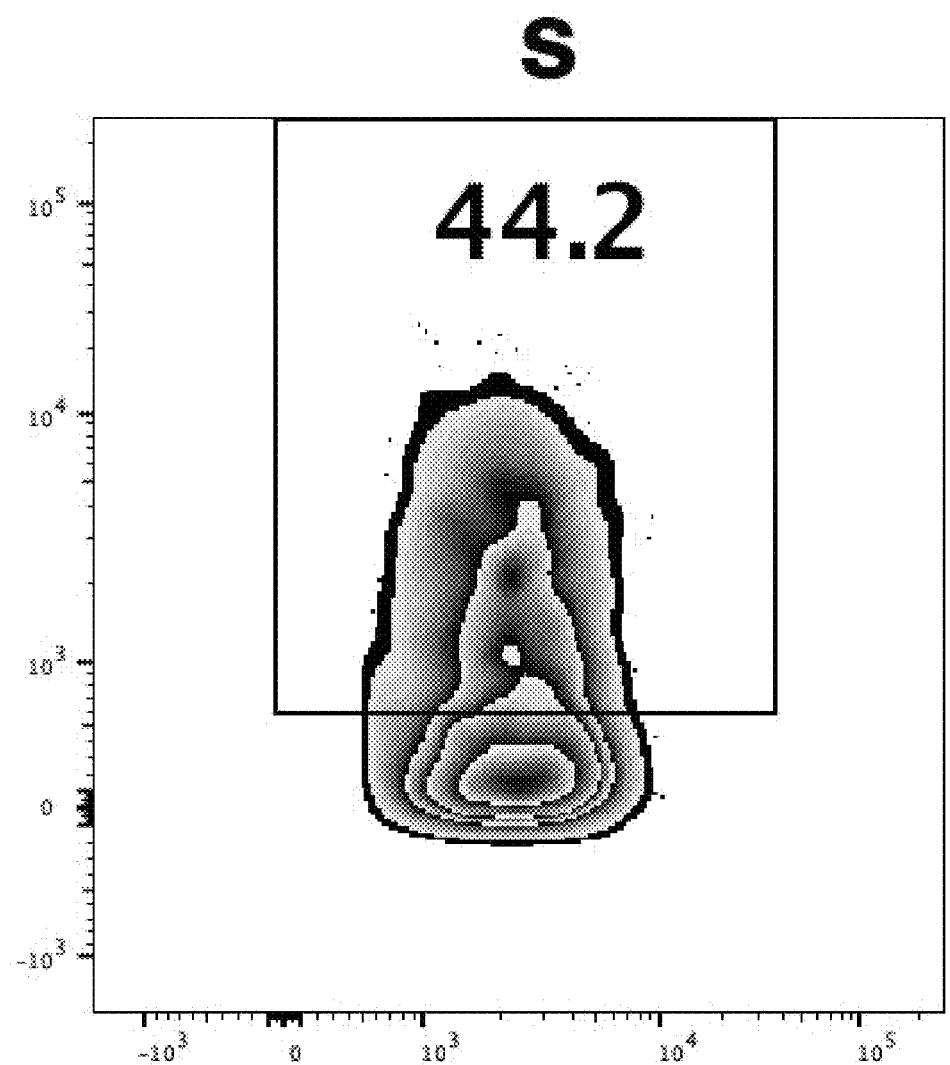
Figure 14D:
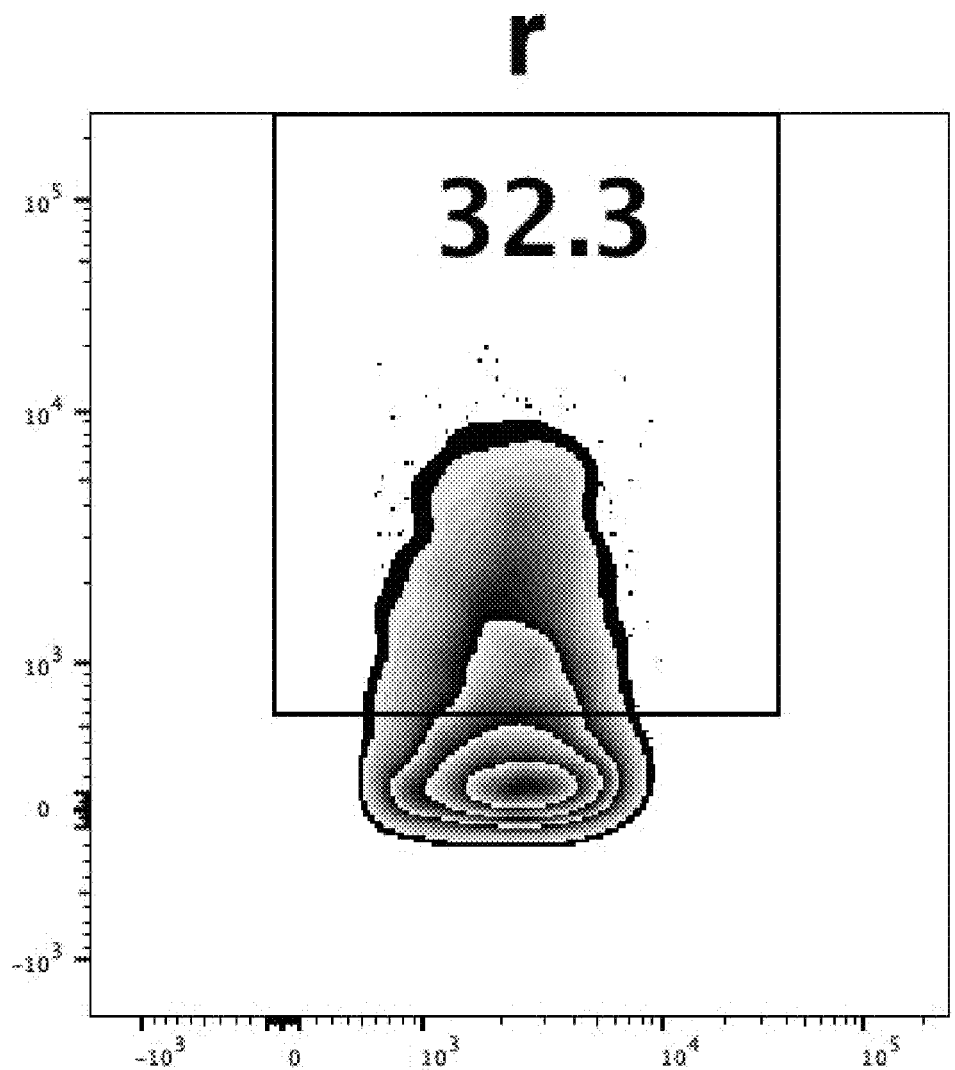
Figure 14E:
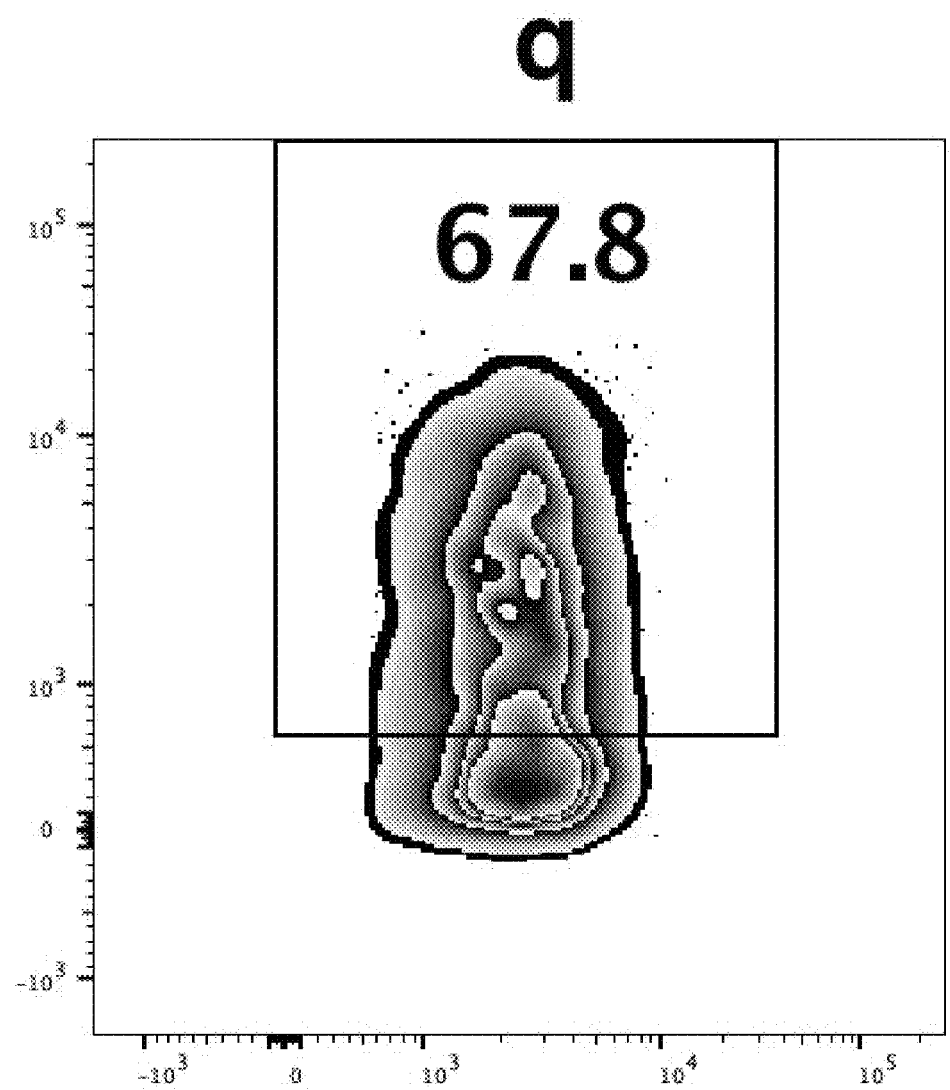
Figure 14F:
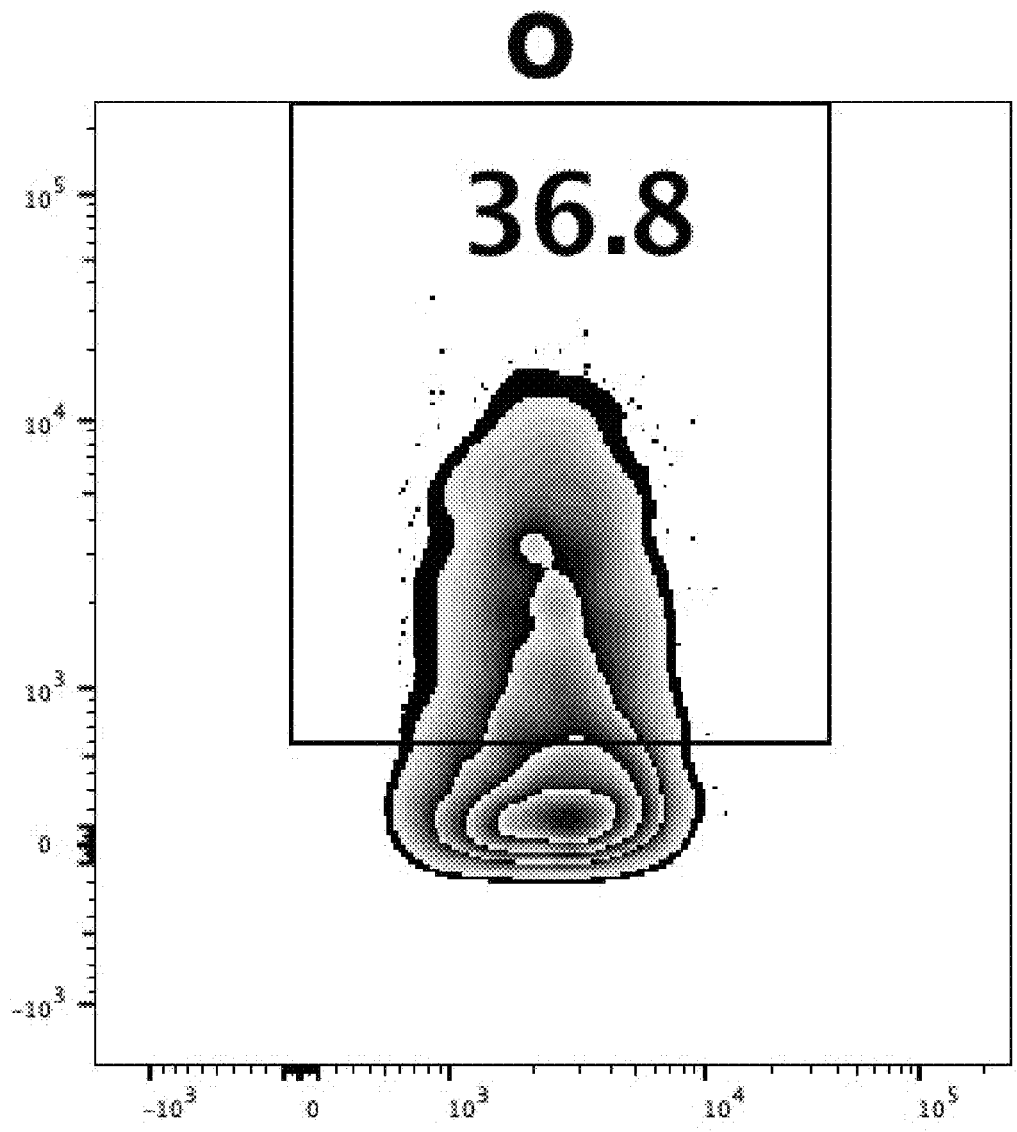
Figure 14G:
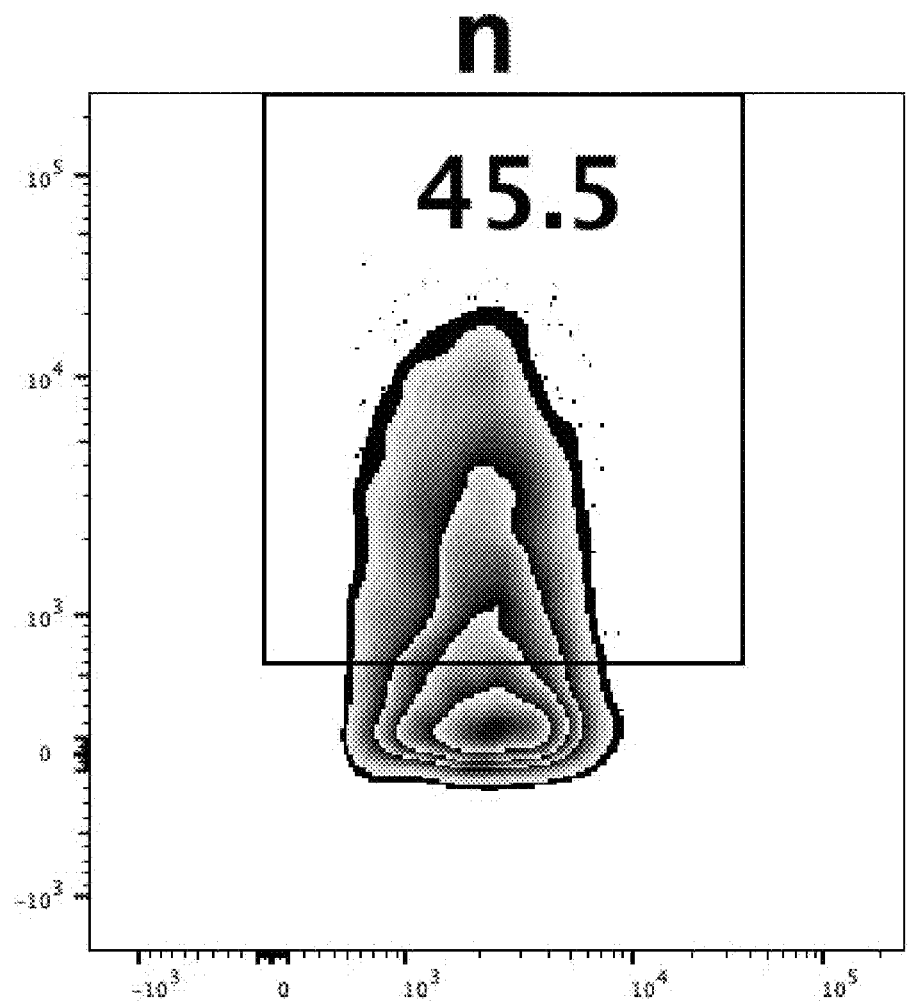
Figure 14H:
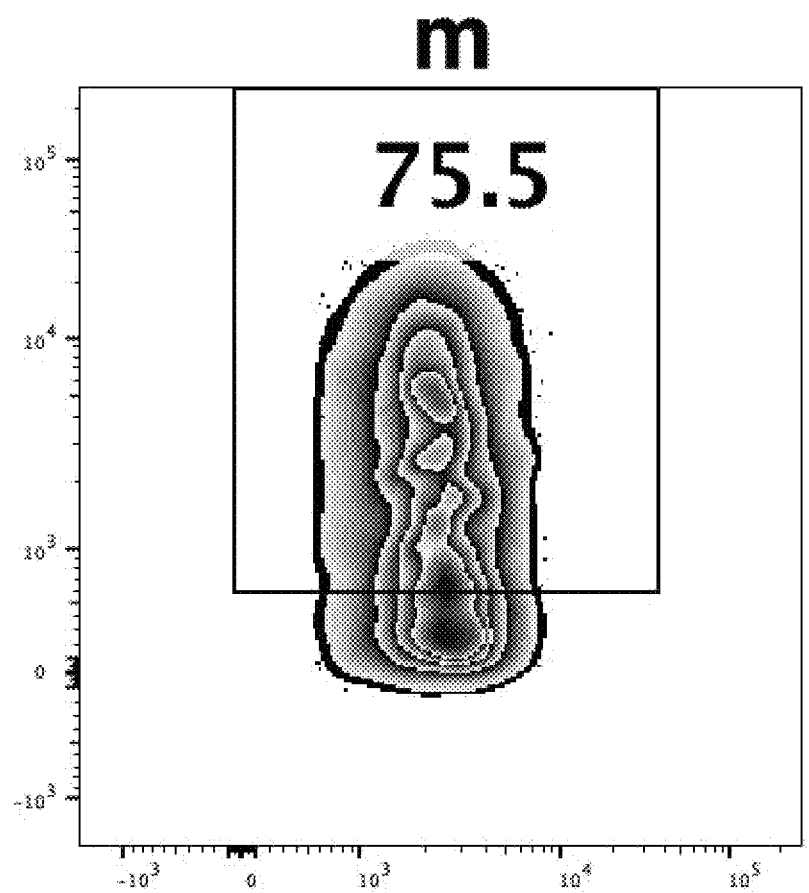
Figure 14I:
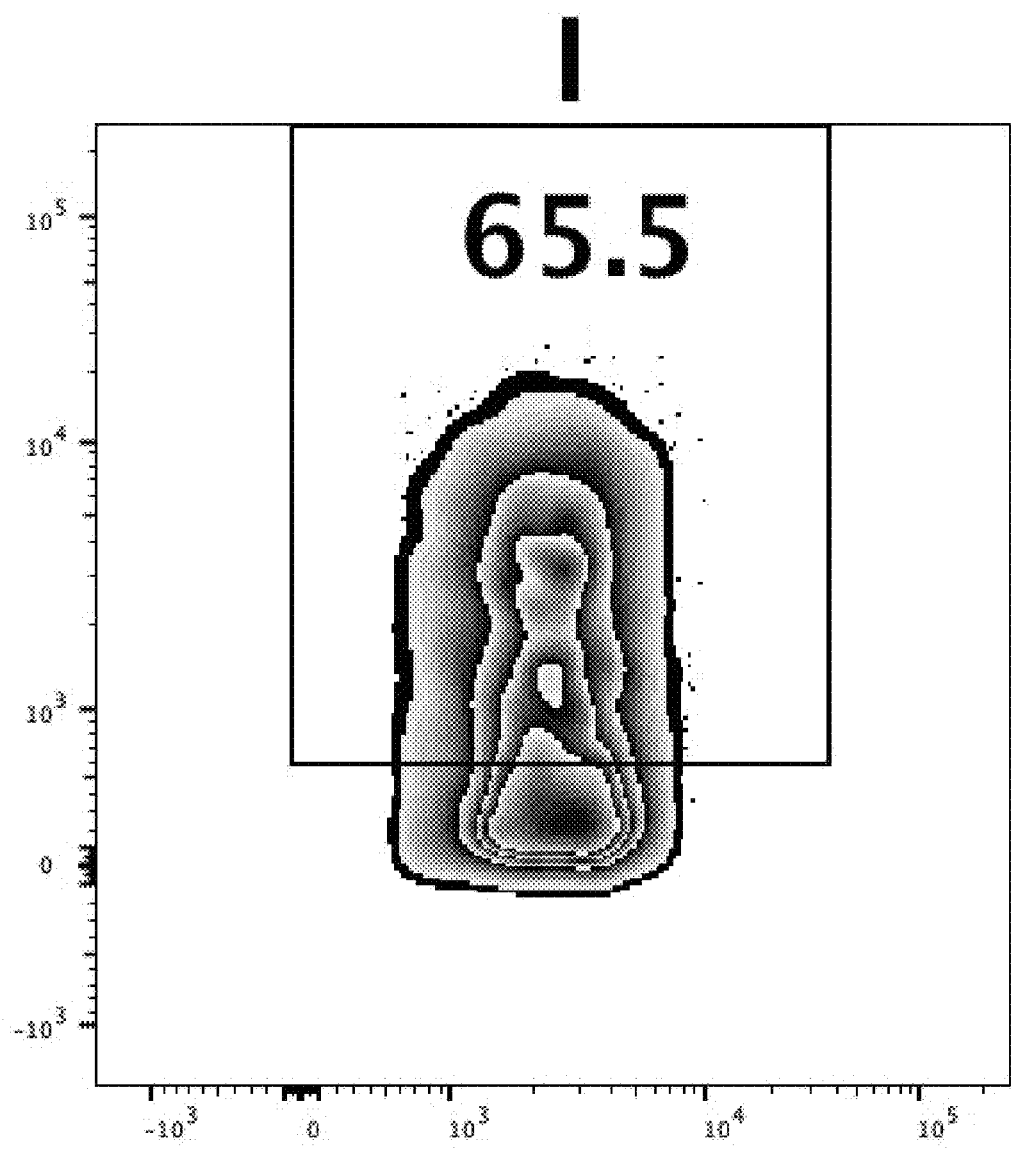
Figure 14J:
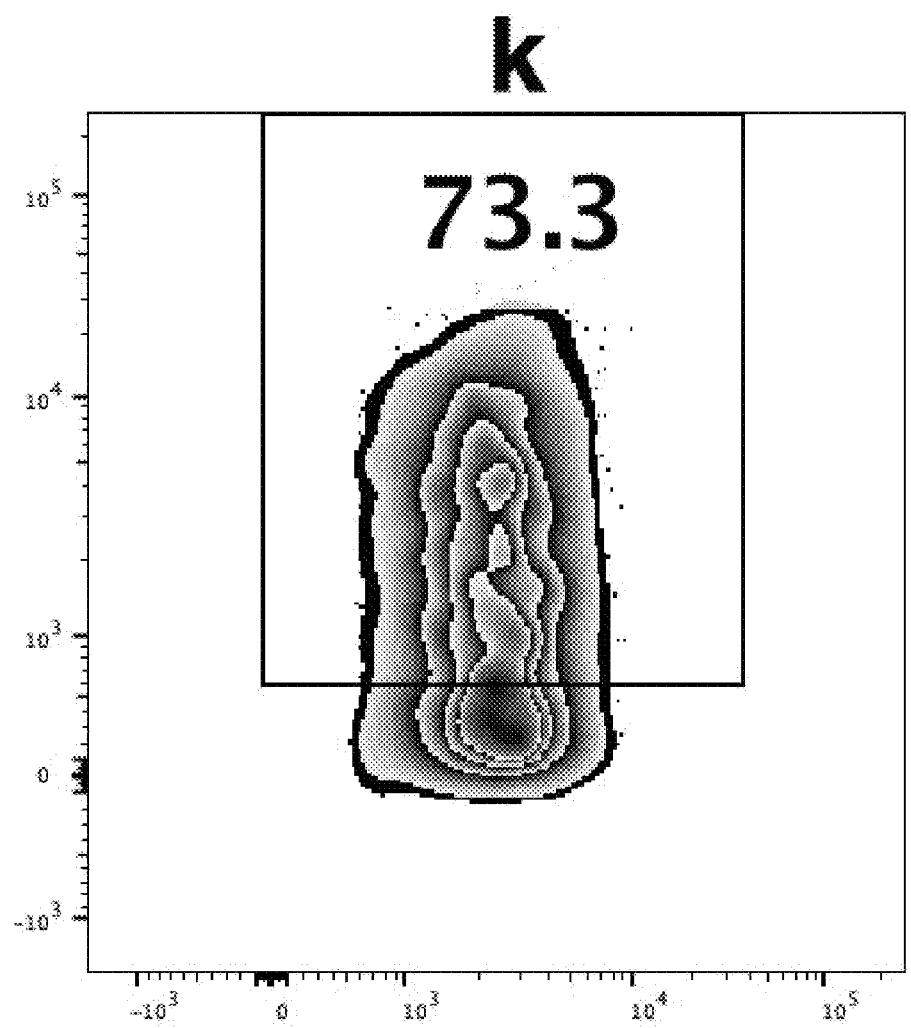
Figure 16:
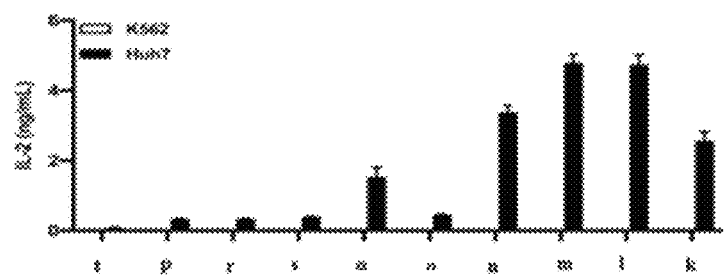
Figure 18:
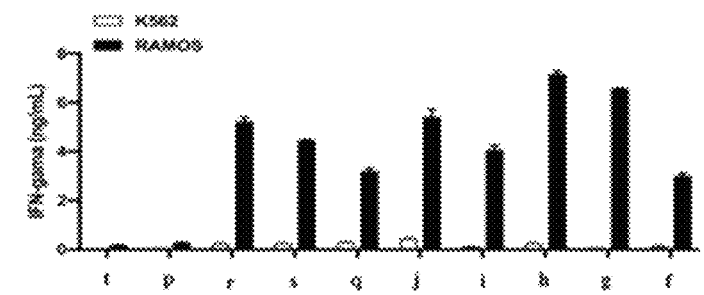
Figure 19:
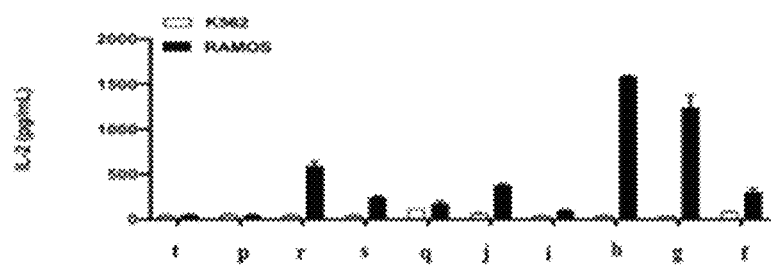
Figure 17A:
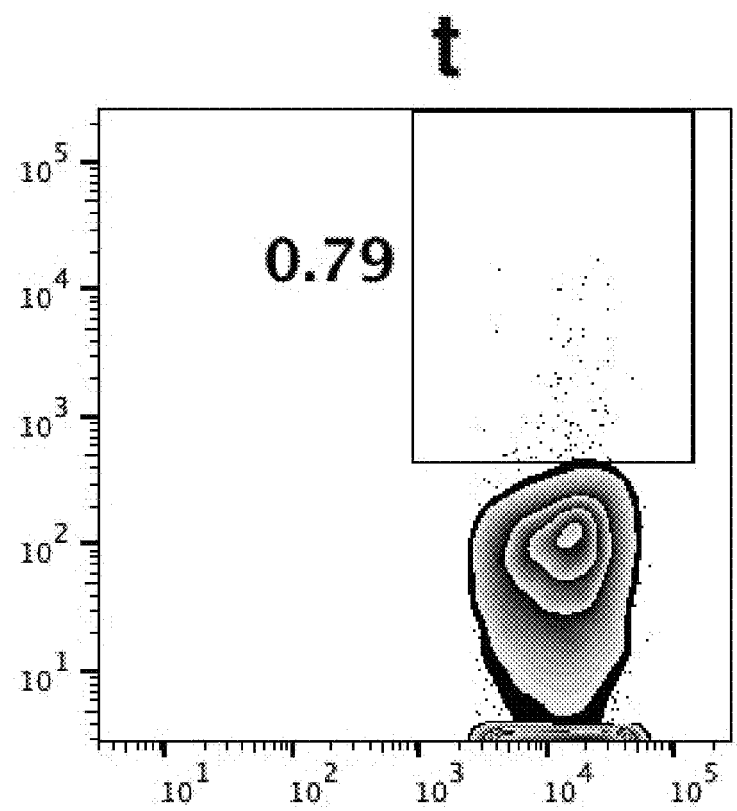
Figure 17B:
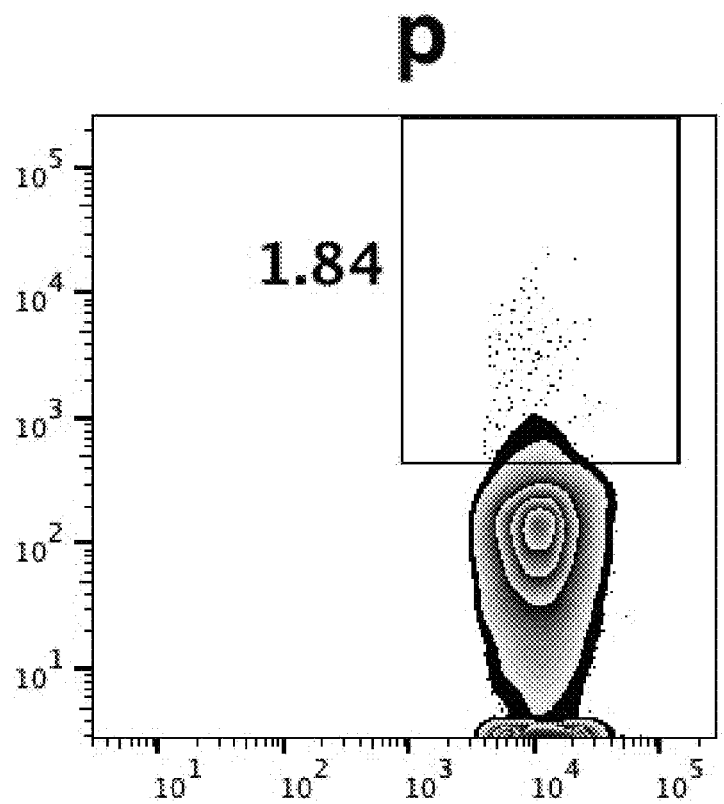
Figure 17C:
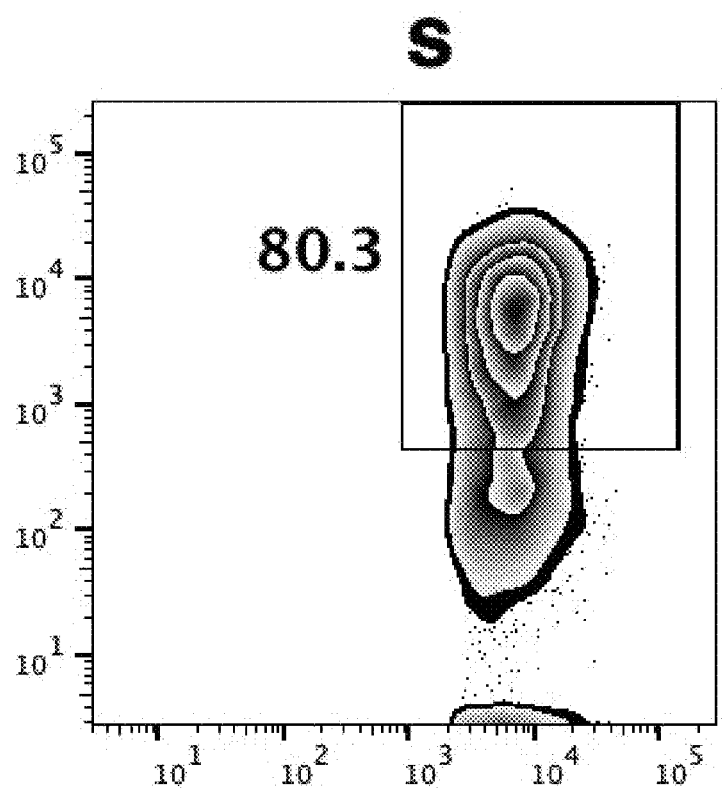
Figure 17D:
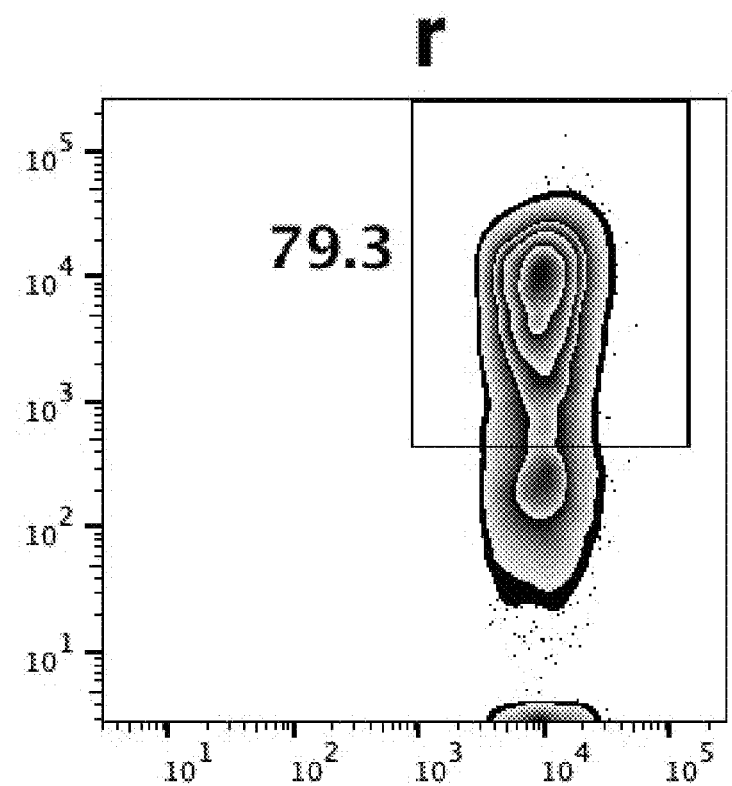
Figure 17E:
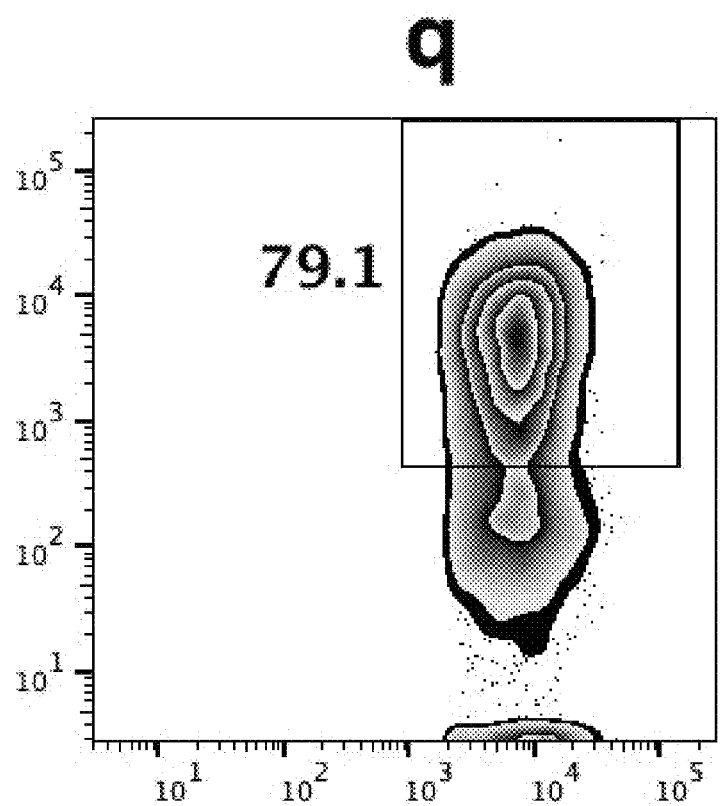
Figure 17F:
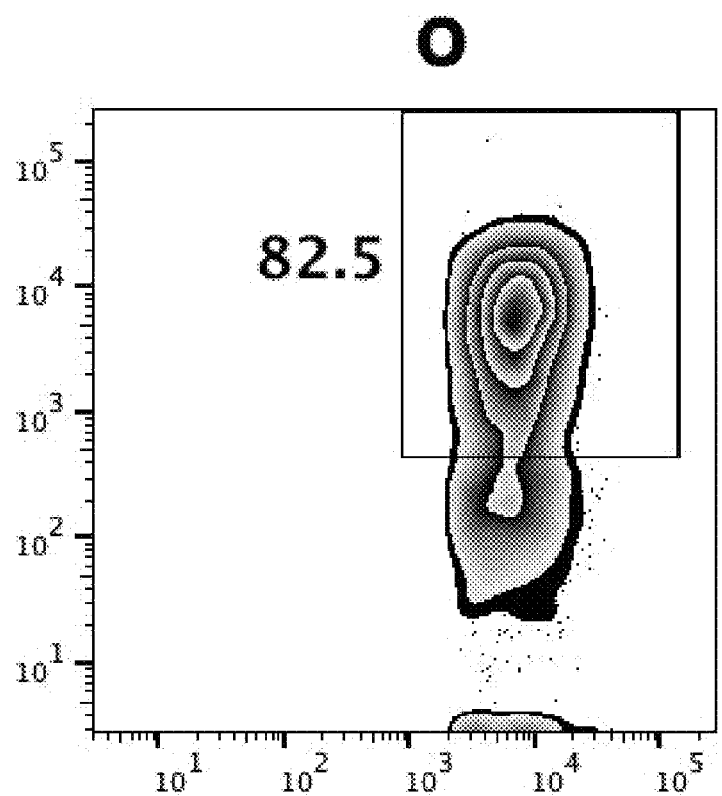
Figure 17G:
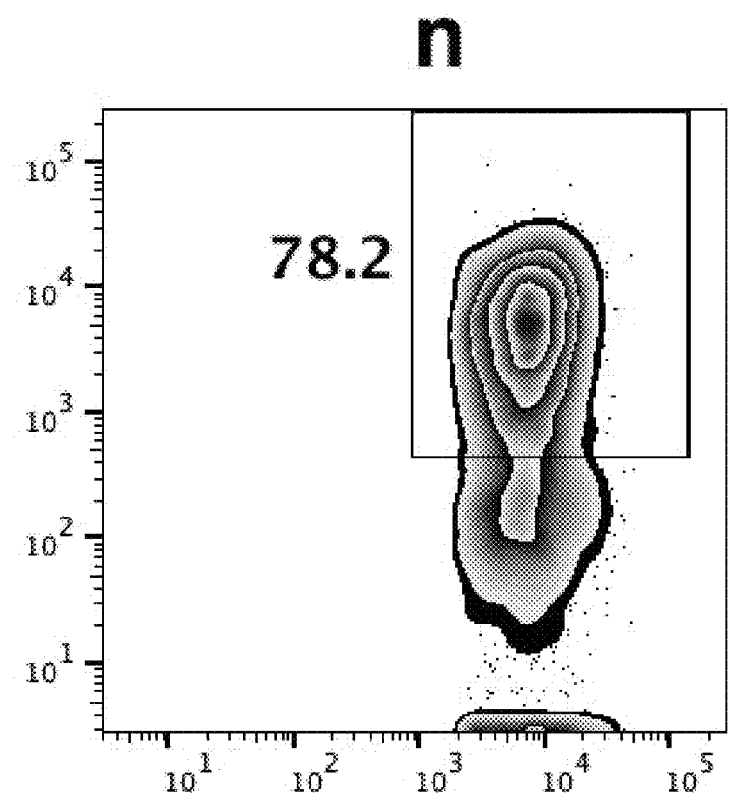
Figure 17H:
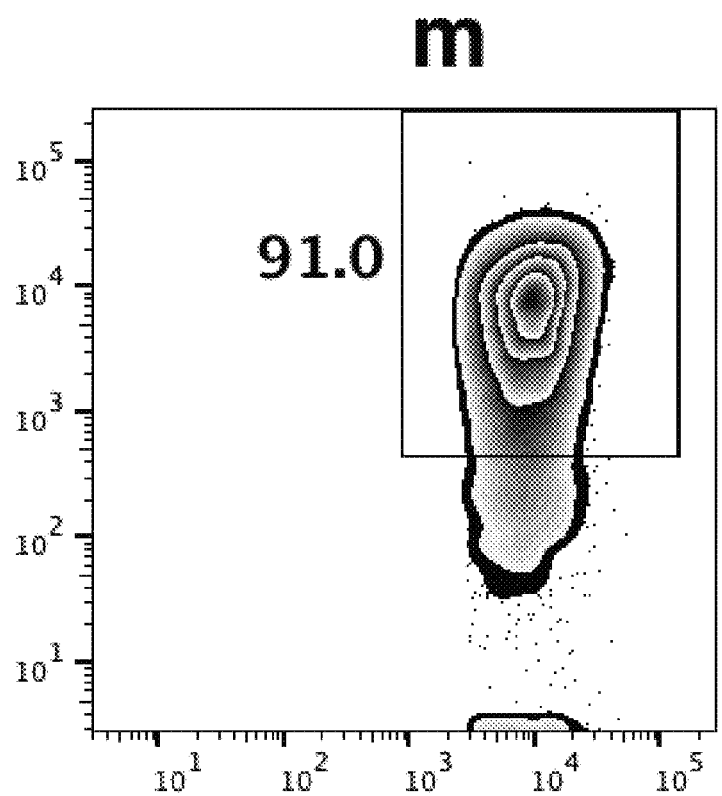
Figure 17I:
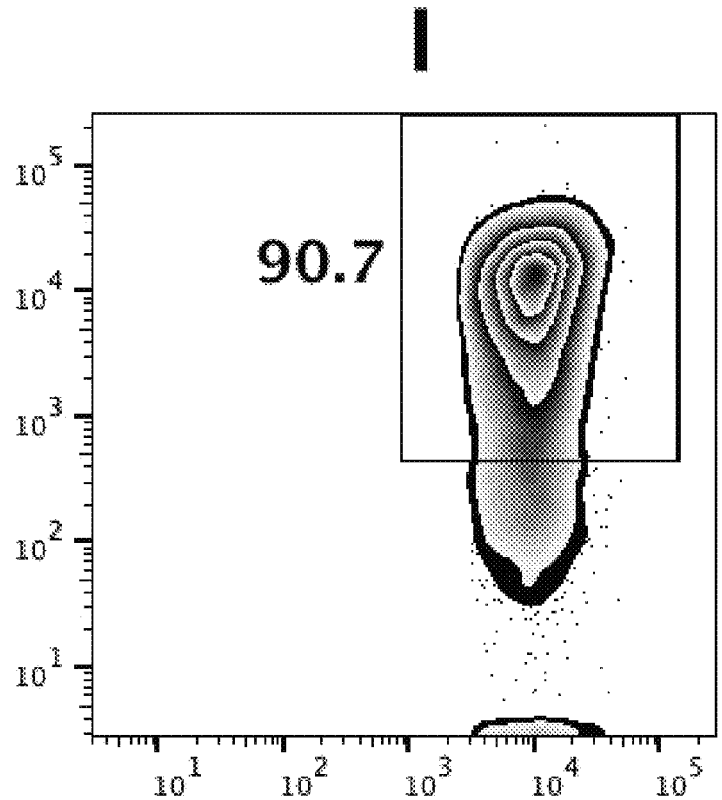
Figure 17J:
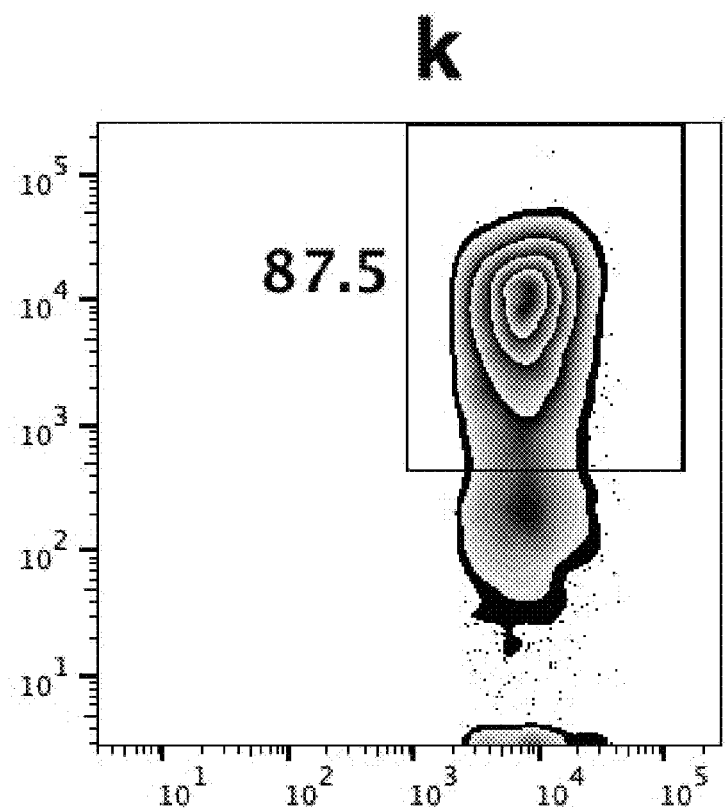
Figure 20:
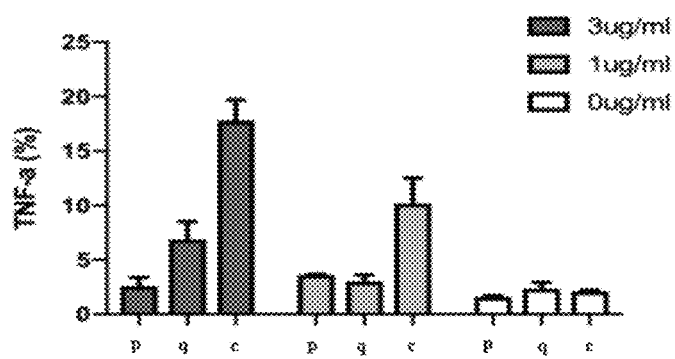
Figure 21:
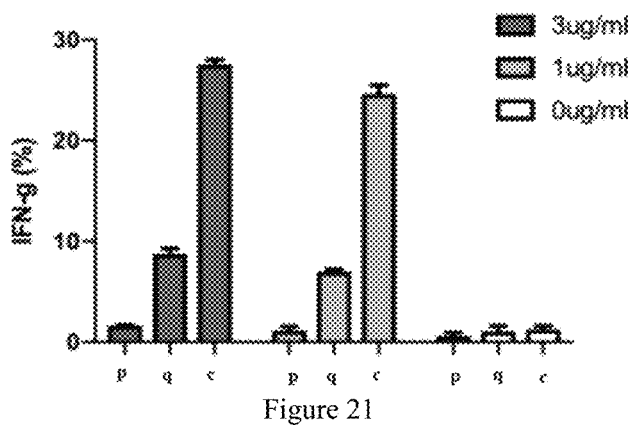
Figure 22:
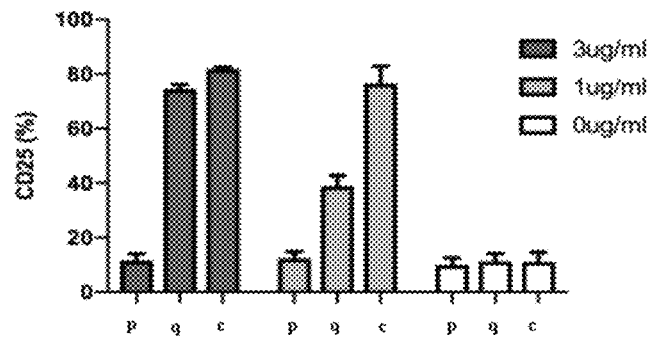
Figure 23:
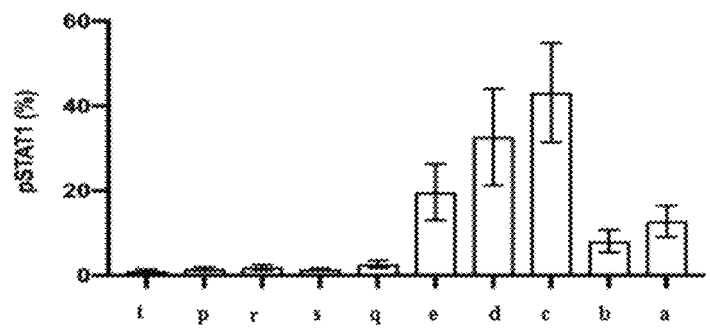
Figure 24:
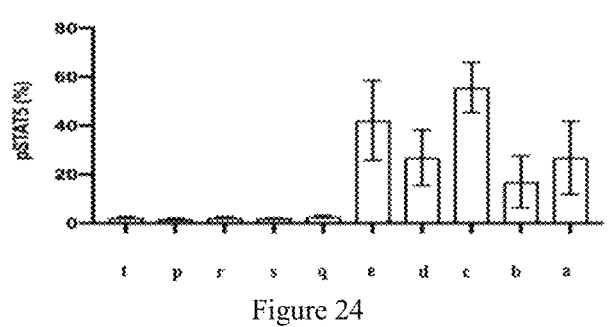
Figure 25:
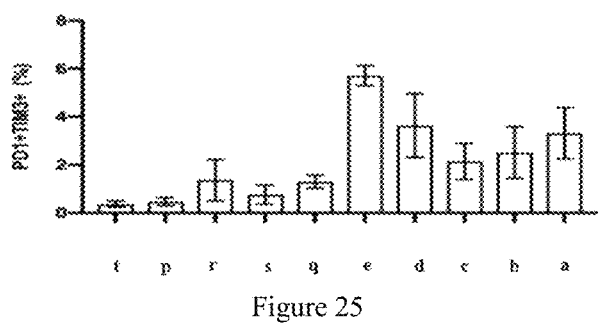

FIGS. 14A-J show the CD107a membrane translocation level of GPC3-CAR-T cells;

FIG. 15 shows the IFN-γ secretion of GPC3-CAR-T cells;

FIG. 16 shows the IL-2 secretion of GPC3-CAR-T cells;

FIGS. 17A-J show the CD107a membrane translocation level of CD19-CAR-T cells;

FIG. 18 shows the IFN-γ secretion of CD19-CAR-T cells;

FIG. 19 shows the IL-2 secretion of CD19-CAR-T cells;

FIG. 20 shows the TNF-α secretion of CAR-T cells stimulated by different concentrations of antigens;

FIG. 21 shows the IFN-γ secretion of CAR-T cells stimulated by different concentrations of antigens;

FIG. 22 shows the difference of activation level, as measured by CD25 expression, of CAR-T cells stimulated by different concentrations of antigens;

FIG. 23 shows the downstream signal transduction, as measured by phosphorylation of STAT1, after CAR-T cells activation;

FIG. 24 shows the downstream signal transduction, as measured by phosphorylation of STATS, after CAR-T cells activation;

FIG. 25 shows the expression level of exhaustion markers (PD-1 and TIM3) on the surface of CAR-T cells.

DETAILED DESCRIPTION

The invention provides a general sequence of chimeric antigen receptor, wherein the hinge domain includes hinge domain V-5, hinge domain V-4-5, hinge domain V-3-4-5, hinge domain V-2-3-4-5 or hinge domain V-1-2-3-4-5.

The nucleotide sequence of the hinge domain V-5 is set forth in SEQ ID NO.1, in particular:

ccatctccag ccgacctctc tccgggagca tcctctgtga ccccgcctgc ccctgcgaga gagccaggac actctccgca g.

The nucleotide sequence of the hinge domain V-4-5 is set forth in SEQ ID NO.2, in particular: gactgttgct ttgggacatt taacgatcag aaacgtggca tctgtcgacc ctggacaaac tgttctttgg atggaaagtc tgtgcttgtg aatgggacga aggagaggga cgtggtctgt ggaccatctc cagccgacct ctctccggga gcatcctctg tgaccccgcc tgccccctgcg agagagccag gacactctcc gcag.

The nucleotide sequence of the hinge domain V-3-4-5 is set forth in SEQ ID NO.3, in particular: gactgcactc cagggtttca ctgcctgggg gcaggatgca gcatgtgtga acaggattgt aaacaaggtc aagaactgac aaaaaaaggt tgtaaagact gttgctttgg gacatttaac gatcagaaac gtggcatctg tcgaccctgg acaaactgtt ctttggatgg aaagtctgtg cttgtgaatg ggacgaagga gagggacgtg gtctgtggac catctccagc cgacctctct ccgggagcat cctctgtgac cccgcctgcc cctgcgagag agccaggaca ctctccgcag.

The nucleotide sequence of the hinge domain V-2-3-4-5 is set forth in SEQ ID NO.4, in particular: agtccctgtc ctccaaatag tttctccagc gcaggtggac aaaggacctg tgacatatgc aggcagtgta aaggtgtttt caggaccagg aaggagtgtt cctccaccag caatgcagag tgtgactgca ctccagggtt tcactgcctg ggggcaggat gcagcatgtg tgaacaggat tgtaaacaag gtcaagaact gacaaaaaaa ggttgtaaag actgttgctt tgggacattt aacgatcaga aacgtggcat ctgtcgaccc tggacaaact gttctttgga tggaaagtct gtgcttgtga atgggacgaa ggagagggac gtggtctgtg gaccatctcc agccgacctc tctccgggag catcctctgt gaccccgcct gcccctgcga gagagccagg acactctccg cag.

The nucleotide sequence of the hinge domain V-1-2-3-4-5 is set forth in SEQ ID NO.5, in particular: ttgcaggatc cttgtagtaa ctgcccagct ggtacattct gtgataataa caggaatcag atttgcagtc cctgtcctcc aaatagtttc tccagcgcag gtggacaaag gacctgtgac atatgcaggc agtgtaaagg tgttttcagg accaggaagg agtgttcctc caccagcaat gcagagtgtg actgcactcc agggtttcac tgcctggggg caggatgcag catgtgtgaa caggattgta aacaaggtca agaactgaca aaaaaaggtt gtaaagactg ttgctttggg acatttaacg atcagaaacg tggcatctgt cgaccctgga caaactgttc tttggatgga aagtctgtgc ttgtgaatgg gacgaaggag agggacgtgg tctgtggacc atctccagcc gacctctctc cgggagcatc ctctgtgacc ccgcctgccc ctgcgagaga gccaggacac tctccgcag.

Figure 1:
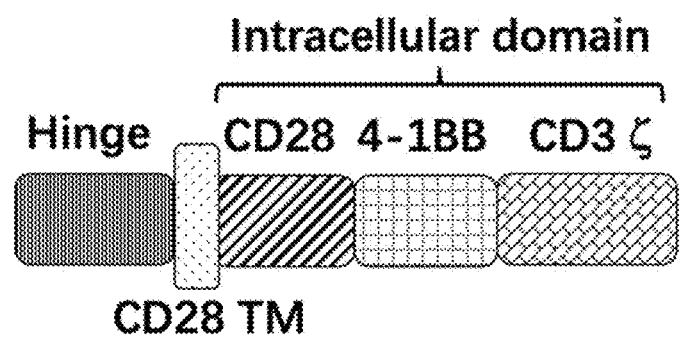
FIG. 1 shows the structural diagram of a general sequence of chimeric antigen receptor of the present application.

In an embodiment, the general sequence of the chimeric antigen receptor is obtained by successively connecting the hinge domain (hinge), the transmembrane domain (TM) and the T cell activation related motif, The structural diagram of the chimeric antigen receptor is shown in FIG. 1. The hinge domain connects the monoclonal antibody sequence and transmembrane sequence, i.e. hinge in FIG. 1. The transmembrane domain enables CAR to be anchored on the cell membrane of immune cells, i.e. CD28 TM in FIG. 1. The intracellular signal transduction sequence, mainly one or more intracellular segments of costimulatory molecules and CD3ζ chains in series, provides CAR-T cells with the first and second signals required for activation, i.e. CD28, 4-1BB and CD3ζ in FIG. 1.

In an embodiment, the nucleotide sequence of the general sequence including the hinge domain V-5 is set forth in SEQ ID NO.6, in particular:

(V-5 hinge)
ccatctccagccgacctctctccgggagcatcctctgtgaccccgcctgc ccctgcgagagagccaggacactctccgcag.

(CD28 TM)
ttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagcccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccctgcccctcgctaa.

In an embodiment, the nucleotide sequence of the general sequence including the hinge domain v-4-5 is set forth in SEQ ID NO.7, in particular:

(V-4-5 hinge)
gactgttgattgggacatttaacgatcagaaacgtggcatctgtcgaccc tggacaaactgttctttggatggaaagtctgtgcttgtgaatgggacgaa ggagagggacgtggtctgtggaccatctccagccgacctctctccgggag catcctctgtgaccccgcctgcccctgcgagagagccaggacactctccg cag.

(CD28 TM)
ttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagcccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccctgcccctcgctaa.

In an embodiment, the nucleotide sequence of the general sequence including the hinge domain v-3-4-5 is set forth in SEQ ID NO.8, in particular:

(V-3-4-5 hinge)
gactgcactccagggtttcactgcctgggggcaggatgcagcatgtgtga acaggattgtaaacaaggtcaagaactgacaaaaaaaggttgtaaagact gttgctttgggacatttaacgatcagaaacgtggcatctgtcgaccctgg acaaactgttctttggatggaaagtctgtgcttgtgaatgggacgaagga gagggacgtggtctgtggaccatctccagccgacctctctccgggagcat cctctgtgaccccgcctgcccctgcgagagagccaggacactctccgca g.

(CD28 TM)
ttttgggtgctggtggtggttggtggagtcctggcttgctatagcttgc tagtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatga gaccagtacaaactactcaagaggaagatggctgtagctgccgatttcc agaagaagaagaaggaggatgtgaactg.

(CD3 ζ)
agagtgaagttcagcaggagcgcagagcccccgcgtaccagcagggcc agaaccagctctataacgagctcaatctaggacgaagagaggagtacga tgttttggacaagagacgtggccgggaccctgagatgggggaaagccg agaaggaagaaccctcaggaaggcctgtacaatgaactgcagaaagata agatggcggaggcctacagtgagattgggatgaaaggcgagcgccggag gggcaaggggcacgatggcctttaccagggtctcagtacagccaccaag gacacctacgacgcccttcacatgcaggccctgccccctcgctaa.

In an embodiment, the nucleotide sequence of the general sequence including the hinge domain v-2-3-4-5 is set forth in SEQ ID NO.9, in particular:

(V-2-3-4-5 hinge)
agtccctgtcctccaaatagtttctccagcgcaggtggacaaaggacct gtgacatatgcaggcagtgtaaaggtgttttcaggaccaggaaggagtg ttcctccaccagcaatgcagagtgtgactgcactccaggg tttcactgc ctgggggcaggatgcagcatgtgtgaacaggattgtaaacaaggtcaag aactgacaaaaaaaggttgtaaagactgttgctttgggacatttaacga tcagaaacgtggcatctgtcgaccctggacaaactgttctttggatgga aagtctgtgcttgtgaatgggacgaaggagagggacgtggtctgtggac catctccagccgacctctctccgggagcatcctctgtgacccc gcctgc ccctgcgagagagccaggacactctccgcag.

(CD28 TM)
ttttgggtgctggtggtggttggtggagtcctggcttgctatagcttgc tagtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatg agaccagtacaaactactcaagaggaagatggctgtagctgccgatttc cagaagaagaagaaggaggatgtgaactg.

(CD3 ζ)
agagtgaagttcagcaggagcgcagagcccccgcgtaccagcagggc cagaaccagctctataacgagctcaatctaggacgaagagaggagtac gatgttttggacaagagacgtggccgggaccctgagatgggggaaag ccgagaaggaagaaccctcaggaaggcctgtacaatgaactgcagaaa gataagatggcggaggcctacagtgagattgggatgaaaggcgagcgc cggaggggcaaggggcacgatggcctttaccagggtctcagtacagcc accaaggacacctacgacgccatcacatgcaggccctgcccctcgct aa.

In an embodiment, the nucleotide sequence of the general sequence including the hinge domain v-1-2-3-4-5 is set forth in SEQ ID NO.10, in particular:

(V-1-2-3-4-5 hinge)
ttgcaggatccttgtagtaactgcccagctggtacattctgtgataataa caggaatcagatttgcagtccctgtcctccaaatagtttctccagcgcag gtggacaaaggacctgtgacatatgcaggcagtgtaaaggtgttttcagg accaggaaggagtgttcctccaccagcaatgcagagtgtgactgcactcc agggtttcactgcctgggggcaggatgcagcatgtgtgaacaggattgta aacaaggtcaagaactgacaaaaaaaggttgtaaagactgttgctttggg acatttaacgatcagaaacgtggcatctgtcgaccctggacaaactgttc tttggatggaaagtctgtgcttgtgaatgggacgaaggagagggacgtgg tctgtggaccatctccagccgacctctctccgggagcatcctctgtgacc ccgcctgccc ctgcgagagagccaggacactctccgcag.

(CD28 TM)
ttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatga gaccagtacaaactactcaagaggaagatggctgtagctgccgatttcc agaagaagaagaaggaggatgtgaactg.

(CD3 ζ)
agagtgaagttcagcaggagcgcagagcccccgcgtaccagcagggcc agaaccagctctataacgagctcaatctaggacgaagagaggagtacga tgttttggacaagagacgtggccgggaccctgagatgggggaaagccg agaaggaagaaccctcaggaaggcctgtacaatgaactgcagaaagata agatggcggaggcctacagtgagattgggatgaaaggcgagcgccggag gggcaaggggcacgatggcctttaccagggtctcagtacagccaccaag gacacctacgacgcccttcacatgcaggccctgccccctcgctaa.

In an embodiment, the chimeric antigen receptor, including the general sequences above, is obtained by connecting a single chain antibody and the general sequence in series, wherein the single chain antibody includes HER2, CD19 or GPC3. HER2 is derived from the humanized antibody 4D5. The nucleotide sequence of the HER2 is set forth in SEQ ID NO.26, in particular:

atggattttcaggtgcagattttcagcttcctgctaatcagtgcctcagt cataatgtccagaggagatatccagatgacccagtccccgagctccctgt ccgcctctgtgggcgatagggtcaccatcacctgccgtgccagtcaggat gtgaatactgctgtagcctggtatcaacagaaaccaggaaaagctccgaa actactgatttactcggcatccttcctttattctggagtcccttctcgct tctctggatctagatctgggacggatttcactctgaccatcagcagtctg cagccggaagacttcgcaacttattactgtcagcaacattatactactcc tcccacgttcggacagggtaccaaggtggagatcaaaggtggtggtggtt ctggcggcggcggctccgaggttcagctggtggagtctggcggtggcctg gtgcagccaggggctcactccgtttgtcctgtgcagcttctggcttcaa cattaaagacacctatatacactgggcgtcaggccccgggtaagggcc tggaatgggttgcaaggatttatcctacgaatggttatactagatatgcc gatagcgtcaagggccgtttcactataagcgcagacacatccaaaaacac agcctacctgcagatgaacagcctgcgtgctgaggacactgccgtctatt attgttctagatggggaggggacggcttctatgctatggacgtgtgggt caaggaaccctggtcaccgtctcctcg.

The GPC3 is from the monoclonal antibody GC33. The nucleotide sequence of GPC3 is set forth in SEQ ID NO.27, in particular: atggattttc aggtgcagat tttcagcttc ctgctaatca gtgcctcagt cataatgtcc agaggagatg ttgtgatgac tcagtctcca ctctccctgc ccgtcacccc tggagagccg gcctcctctc ctgcagatct agtcagagcc ttgtacacag taatgccaac acctatttac attggtacct gcagaagcca gggcagtctc cacagctcct gatctataaa gtttccaacc gattttctgg ggtccctgac aggttcagtg gcagtggatc aggcacagat ttta- cactga aaatcagcag agtggaggct gaggatgttg gggtttatta ctgctct- caa aatacacatg ttcctcctac gttggccag gggaccaagc tggagatcaa acgtgtggag gcggttcaggcggaggtggc tctcaggtgc agctggtgca gtctggagct gaggtgaaga agcctggggc tcagtgaag gtctcctgca aggcttctgg atacaccttc accgactatg aaatgcactg ggtgcgacag gcccctggac aagggcttga gtggatggga gctcttgatc ctaaaactggtga- tactgcc tacagtcaga agttcaaggg cagagtcacg ctgaccgcgg acgaatccac gagcacagcc tacatggagc tgagcagcct gagatctgag gacacggccg tgtattactg tacaagattc tactcctata cttactgggg ccagg- gaacc ctggtcaccg tctcctca.

The CD19 is from the monoclonal antibody FMC63. The nucleotide sequence of the CD19 is set forth in SEQ ID NO.28, in particular: atggattttc aggtgcagat tttcagcttc ctgctaatca gtgcctcagt cataatgtcc agaggagaca tccagatgac aca- gactaca tcctccctgt ctgcctctct gggagacagagtcaccatca gttgcagggc aagtcaggac attagtaaat atttaaattg gtatcagcag aaaccagatg gaactgttaa actcctgatc taccatacat caagattaca ctcag- gagtc ccatcaaggt tcagtggcag tgggtctgga acagattatt ctctcaccat tagcaacctg gagcaagaag atattgccac ttactttgc caacagggta atacgcttcc gtacacgttc ggaggggga ccaagctgga gatcacaggt ggcggtggct cggcggtgg tgggtcgggt ggcggcggat ctgaggtgaa actgcaggag tcaggacctg gcctggtggc ccctcacag agcctgtccg tcacatgcac tgtctcaggg gtctcattac ccgactatgg tgtaagctgg attcgccagc ctccacgaaa gggtctggag tggctgggag taatatgggg tagtgaaacc acatactata attcagctct caaatccaga ctgaccatca tcaaggacaa ctccaagagccaagttttct taaaaatgaa cagtctgcaa act- gatgaca cagccattta ctactgtgcc aaacattatt actacggtgg tagc- tatgct atggactact ggggccaagg aacctcagtcaccgtctcctca.

Figure 2:
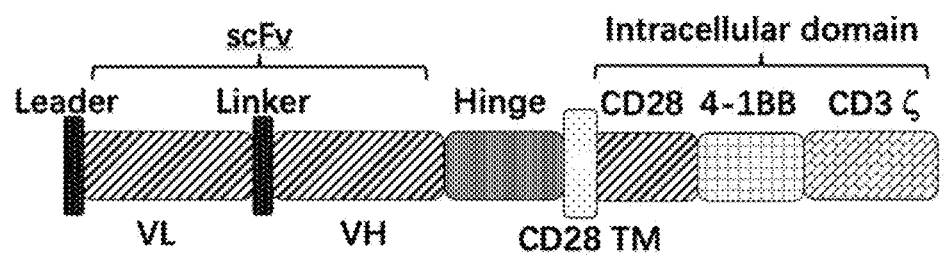
FIG. 2 shows the structural diagram of a chimeric antigen receptor of the application.

In an embodiment, the chimeric antigen receptor is obtained by successively connecting single chain Fv (scFv) which is non-MHC restricted to recognize target antigen, with hinge domain (hinge), transmembrane domain (TM) and T cell activation related motif in series, i.e., it is obtained by connecting the single chain Fv (scFv) which is non-MHC restricted to recognize target antigen with the general sequence of chimeric antigen receptor, the structural diagram is shown in FIG. 2. scFv is a monoclonal single chain antibody sequence at the outer end, which mainly recognizes antigens and determines the targeting of CAR-T cells. scFv includes a leader, a VL, a VH and a linker.

In an embodiment, when the single chain antibody is HER2, the chimeric antigen receptor includes HER2-V 5, HER2-V 4-5, HER2-V 3-4-5, HER2-V 2-3-4-5 and HER2-V 1-2-3-4-5.

In an embodiment, the HER2-V 5 is obtained by connecting the HER2 and the general sequence including the hinge domain V-5 in series; the nucleotide sequence of the HER2-V 5 is set forth in SEQ ID NO.11, in particular:

(HER2 scFv)
atggattttcaggtgcagattttcagcttcctgctaatcagtgcctcag tcataatgtccagaggagatatccagatgacccagtccccgagctccct gtccgcctctgtgggcgatagggtcaccatcacctgccgtgccagtcag gatgtgaatactgctgtagcctggtatcaacagaaaccaggaaaagctc cgaaactactgatttactcggcatccttcctttattctggagtcccttc tcgcttctctggatctagatctgggacggatttcactctgaccatcagc agtctgcagccggaagacttcgcaacttattactgtcagcaacattata ctactcctcccacgttcggacagggtaccaaggtggagatcaaaggtgg tggtggttctggcggcggcggctccgaggttcagctggtggagtctggc ggtggcctggtgcagccaggggctcactccgtttgtcctgtgcagatc tggcttcaacattaaagacacctatatacactgggcgtcaggccccg ggtaagggcctggaatgggttgcaaggatttatcctacgaatggttata ctagatatgccgatagcgtcaagggccgtttcactataagcgcagacac atccaaaaacacagcctacctgcagatgaacagcctgcgtgctgaggac actgccgtctattattgttctagatggggaggggacggcttctatgcta tggacgtgtgggtcaaggaaccctggtcaccgtctcctcg.

(V-5 hinge)
ccatctccagccgacctctctccgggagcatcctctgtgaccccgcctg cccctgcgagagagccaggacactctccgcag.

(CD28 TM)
ttttgggtgctggtggtggttggtggagtcctggcttgctatagcttgc tagtaacagtggcctttattattttctgggtg.

(CD28)
aggagtaagag gagcaggctc ctgcacagtg actacatgaa catgactccc cgccgcccg ggcccacccg caagcattac cagccctatg ccccaccacg cgacttcgca gcctatcgct cc.

(4-1BB)
aaacggggcagaaagaaactcctgtatatattcaaacaaccatttatga gaccagtacaaactactcaagaggaagatggctgtagctgccgatttcc agaagaagaagaaggaggatgtgaactg.

(CD3 ζ)
agagtgaagttcagcaggagcgcagagccccccgcgtaccagcagggcc agaaccagctctataacgagctcaatctaggacgaagagaggagtacga tgttttggacaagagacgtggccgggaccctgagatgggggaaagccg agaaggaagaaccctcaggaaggcctgtacaatgaactgcagaaagata agatggcggaggcctacagtgagattgggatgaaaggcgagcgccggag gggcaaggggcacgatggcctttaccagggtctcagtacagccaccaag gacacctacgacgccatcacatgcaggccctgccccctcgctaa.

In an embodiment, the HER2-V 4-5 is obtained by connecting the HER2 and the general sequence including the hinge domain V-4-5 in series; the nucleotide sequence of the HER2-V 4-5 is set forth in SEQ ID NO.12, in particular:

(HER2 scFv)
atggattttcaggtgcagattttcagatcctgctaatcagtgcctcagt cataatgtccagaggagatatccagatgacccagtccccgagctccctg tccgcctctgtgggcgatagggtcaccatcacctgccgtgccagtcagg atgtgaatactgctgtagcctggtatcaacagaaaccaggaaaagctcc gaaactactgatttactcggcatccttcctttattctggagtcccttct cgcttctctggatctagatctgggacggatttcactctgaccatcagca gtctgcagccggaagacttcgcaacttattactgtcagcaacattatac tactcctcccacgttcggacagggtaccaaggtggagatcaaaggtggt ggtggttctggcggcggcggctccgaggttcagctggtggagtctggcg gtggcctggtgcagccaggggggctcactccgtttgtcctgtgcagatct ggcttcaacattaaagacacctatatacactgggtgcgtcaggccccgg gtaagggcctggaatggggttgcaaggatttatcctacgaatggttatac tagatatgccgatagcgtcaagggccgtttcactataagcgcagacaca tccaaaaacacagcctacctgcagatgaacagcctgcgtgctgaggaca ctgccgtctattattgttctagatggggagggggacggcttctatgctat ggacgtgtgggtcaaggaaccctggtcaccgtctcctcg.

(V-4-5 hinge)
gactgttgattgggacatttaacgatcagaaacgtggcatctgtcgacc ctggacaaactgttattggatggaaagtctgtgatgtgaatgggacgaa ggagagggacgtggtctgtggaccatctccagccgacctctctccggga gcatcctctgtgaccccgcctgcccctgcgagagagccaggacactctc cgcag.

(CD28 TM)
ttttgggtgctggtggtggttggtggagtcctggcttgctatagcttgc tagtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatg agaccagtacaaactactcaagaggaagatggctgtagctgccgattt ccagaagaagaagaaggaggatgtgaactg.

(CD3 ζ)
agagtgaagttcagcaggagcgcagagccccccgcgtaccagcagggc cagaaccagctctataacgagctcaatctaggacgaagagaggagtac gatgttttggacaagagacgtggccgggaccctgagatgggggaaag ccgagaaggaagaaccctcaggaaggcctgtacaatgaactgcagaaa gataagatggcggaggcctacagtgagattgggatgaaaggcgagcgc cggaggggcaaggggcacgatggcctttaccagggtctcagtacagcc accaaggacacctacgacgcccttcacatgcaggccctgccccctcgc taa.

In an embodiment, the HER2-V 3-4-5 is obtained by connecting the HER2 and the general sequence including the hinge domain V-3-4-5 in series; the nucleotide sequence of the HER2-V 3-4-5 is set forth in SEQ ID NO.13, in particular:

(HER2 scFv)
atggattttcaggtgcagattttcagcttcctgctaatcagtgcctca gtcataatgtccagaggagatatccagatgacccagtccccgagctcc ctgtccgcctctgtgggcgatagggtcaccatcacctgccgtgccagt caggatgtgaatactgctgtagcctggtatcaacagaaaccaggaaaa gctccgaaactactgatttactcggcatccttcctttattctggagtc ccttctcgcttctctggatctagatctgggacggatttcactctgacc atcagcagtctgcagccggaagacttcgcaacttattactgtcagcaa cattatactactcctcccacgttcggacagggtaccaaggtggagatc aaaggtggtggtggttctggcggcggcggctccgaggttcagctggtg gagtctggcggtggcctggtgcagccaggggggctcactccgtttgtcc tgtgcagcttctgcttcaacattaaagacacctatatacactgggtg cgtcaggccccgggtaagggcctggaatggggttgcaaggatttatcct acgaatggttatactagatatgccgatagcgtcaagggccgtttcact ataagcgcagacacatccaaaaacacagcctacctgcagatgaacagc ctgcgtgctgaggacactgccgtctattattgttctagatgggggaggg gacggcttctatgctatggacgtgtggggtcaaggaaccctggtcacc gtctcctcg.

(V-3-4-5 hinge)
gactgcactccagggtttcactgcctgggggcaggatgcagcatgtgt gaacaggattgtaaacaaggtcaagaactgacaaaaaaaggttgtaaa gactgttgattgggacatttaacgatcagaaacgtggcatctgtcgac cctggacaaactgttcttggatggaaagtctgtgcttgtgaatggga cgaaggagagggacgtggtctgtggaccatctccagccgacctctctc -continued cgggagcatcctctgtgaccccgcctgcccctgcgagagagccaggac actctccgcag.

(CD28)
ttttgggtgctggtggtggttggtggagtcctggcttgctatagcttg ctagtaacagtggcctttattattttctgggtgaggagtaaga g gagcaggctc ctgcacagtg actacatgaa catgactccc cgccgcccg ggcccacccg caagcattac cagccctatg ccccaccacg cgacttcgca gcctatcgct cc.

(4-1BB)
aaacggggcagaaagaaactcctgtatatattcaaacaaccatttat gagaccagtacaaactactcaagaggaagatggctgtagctgccgat ttccagaagaagaaggaggatgtgaactg.

(CD3 ζ)
agagtgaagttcagcaggagcgcagagcccccgcgtaccagcaggg ccagaaccagctctataacgagctcaatctaggacgaagagaggagt acgatgttttggacaagagacgtggccgggaccctgagatgggggga aagccgagaaggaagaaccctcaggaaggcctgtacaatgaactgca gaaagataagatggcggaggcctacagtgagattgggatgaaggcg agcgccggaggggcaaggggcacgatggcctttaccagggtctcagt acagccaccaaggacacctacgacgcccttcacatgcaggccctgcc ccctcgctaa.

In an embodiment, the HER2-V 2-3-4-5 is obtained by connecting the HER2 and the general sequence including the hinge domain V-2-3-4-5 in series; the nucleotide sequence of the HER2-V 2-3-4-5 is set forth in SEQ ID NO.14, in particular:

(HER2 scFv)
atggattttcaggtgcagattttcagcttcctgctaatcagtgcctcagt cataatgtccagaggagatatccagatgacccagtccccgagctccctgt ccgcctctgtgggcgatagggtcaccatcacctgccgtgccagtcaggat gtgaatactgctgtagcctggtatcaacagaaaccaggaaaagctccgaa actactgatttactcggcatccttcctttattctggagtcccttctcgct tctctggatctagatctgggacggatttcactctgaccatcagcagtctg cagccggaagacttcgcaacttattactgtcagcaacattatactactcc tcccacgttcggacagggtaccaaggtggagatcaaggtggtggtggtt ctggcggcggcggctccgaggttcagctggtggagtctggcggtggcctg gtgcagccaggggctcactccgtttgtcctgtgcagatctggcttcaac attaaagacacctatatacactgggtgcgtcaggcccgggtaagggcct ggaatggtcgcaaggattatcctacgaatggttatactagatatgccg atagcgtcaaggccgtttcactataagcgcagacacatccaaaacaca gcctacctgcagatgaacagcctgcgtgctgaggacactgccgtctatta ttgttctagatggggagggacggcttctatgctatggacgtgtgggtc aaggaaccctggtcaccgtctcctcg.

(V-2-3-4-5 hinge)
agtccctgtcctccaaatagtttctccagcgcaggtggacaaaggacctg tgacatatgcaggcagtgtaaaggtgttttcaggaccaggaaggagtgtt cctccaccagcaatgcagagtgtgactgcactccagggtttcactgcctg ggggcaggatgcagcatgtgtgaacaggattgtaaacaaggtcaagaact gacaaaaaaaggttgtaaagactgttgattgggacatttaacgatcagaa acgtggcatctgtcgaccctggacaaactgttattggatggaaagtctgt gatgtgaatgggacgaaggagagggacgtggtctgtggaccatctccagc cgacctctctccgggagcatcctctgtgaccccgcctgccctgcgagag agccaggacactctccgcag.

(CD28 TM)
ttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgcccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaaggaggatgtgaactg.

(CD ζ3)
agagtgaagttcagcaggagcgcagagcccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaggcgagcgccggaggggca aggggcacgatggcctttaccagggtctcagtacagccaccaaggacacc tacgacgcccttcacatgcaggccctgccccctcgctaa.

In an embodiment, the HER2-V 1-2-3-4-5 is obtained by connecting the HER2 and the general sequence including the hinge domain V-1-2-3-4-5 in series; the nucleotide sequence of the HER2-V 1-2-3-4-5 is set forth in SEQ ID NO.15, in particular:

(HER2 scFv)
atggattttcaggtgcagattttcagcttcctgctaatcagtgcctcagt cataatgtccagaggagatatccagatgacccagtccccgagctccctgt ccgcctctgtgggcgatagggtcaccatcacctgccgtgccagtcaggat gtgaatactgctgtagcctggtatcaacagaaaccaggaaaagctccgaa actactgatttactcggcatccttcctttattctggagtcccttctcgct tctctggatctagatctgggacggatttcactctgaccatcagcagtctg cagccggaagacttcgcaacttattactgtcagcaacattatactactcc tcccacgttcggacagggtaccaaggtggagatcaaggtggtggtggtt ctggcggcggcggctccgaggttcagctggtggagtctggcggtggcctg

```
gtgcagccagggggctcactccgtttgtcctgtgcagatctggcttcaac attaaagacacctatatacactgggtgcgtcaggccccgggtaagggcct ggaatgggttgcaaggatttatcctacgaatggttatactagatatgccg atagcgtcaaggccgtttcactataagcgcagacacatccaaaaacaca gcctacctgcagatgaacagcctgcgtgctgaggacactgccgtctatta ttgttctagatggggaggggacggcttctatgctatggacgtgtggggtc aaggaaccctggtcaccgtctcctcg.

(V-1-2-3-4-5 hinge)
ttgcaggatccttgtagtaactgcccagctggtacattctgtgataataa caggaatcagatttgcagtccctgtcctccaaatagtttctccagcgcag gtggacaaaggacctgtgacatatgcaggcagtgtaaaggtgttttcagg accaggaaggagtgttcctccaccagcaatgcagagtgtgactgcactcc agggtttcactgcctggggcaggatgcagcatgtgtgaacaggattgta aacaaggtcaagaactgacaaaaaaaggttgtaaagactgttgattggga catttaacgatcagaaacgtggcatctgtcgaccctggacaaactgttct ttggatggaaagtctgtgatgtgaatgggacgaaggagagggacgtggtc tgtgaccatctccagccgacctctctccgggagcatcctctgtgacccc gcctgccctgcgagagagccaggacactctccgcag.

(CD28 TM)
ttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagcccccgcgtaccagcagggcca gaaccagactataacgagctcaatctaggacgaagagaggagtacgatgt tttggacaagagacgtggccgggaccagagatggggggaaagccgagaag gaagaaccctcaggaaggcctgtacaatgaactgcagaaagataagatgg cggaggcctacagtgagattgggatgaaaggcgagcgccggaggggcaag gggcacgatggcctttaccagggtctcagtacagccaccaaggacaccta cgacgcccttcacatgcaggcagcccctcgctaa.
```

In an embodiment, the CD19-V 5 is obtained by connecting the CD19 and the general sequence including the hinge domain V-5 in series; the nucleotide sequence of the CD19-V 5 is set forth in SEQ ID NO.16, in particular:

```
(CD19 scFv)
atggattttcaggtgcagattttcagcttcctgctaatcagtgcctcagt cataatgtccagaggagacatccagatgacacagactacatcctccctgt ctgcctctctgggagacagagtcaccatcagttgcagggcaagtcaggac attagtaaatatttaaattggtatcagcagaaaccagatggaactgttaa actcctgatctaccatacatcaagattacactcaggagtcccatcaaggt tcagtggcagtgggtctgaacagattattctctcaccattagcaacctg gagcaagaagatattgccacttacttttgccaacagggtaatacgcttcc gtacacgttcggaggggggaccaagctggagatcacaggtggcggtggct cgggcggtggtgggtcgggtggcggcggatctgaggtgaaactgcaggag tcaggacctggcctggtggcgccctcacagagcctgtccgtcacatgcac tgtctcagggg tctcattacccgactatggtgtaagctggattcgccagc ctccacgaaagggtctggagtggctgggagtaatatggggtagtgaaacc acatactataattcagctctcaaatccagactgaccatcatcaaggacaa ctccaagagccaagttttcttaaaaatgaacagtctgcaaactgatgaca cagccatttactactgtgccaaacattattactacggtggtagctatgct atggactactggggccaaggaacctcagtcaccgtctcctca.

(V-5 hinge)
ccatctccagccgacctctctccgggagcatcctctgtgacccccgcctgc ccctgcgagagagccaggacactctccgcag.

(CD28 TM)
ttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagcccccgcgtaccagcagggcca gaaccagctctataacgagctcaatctaggacgaagagaggagtacgatg ttttggacaagagacgtggccgggaccctgagatggggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccctgccccctcgctaa.
```

In an embodiment, the CD19-V 4-5 is obtained by connecting the CD19 and the general sequence including the hinge domain V-4-5 in series; the nucleotide sequence of the CD19-V 4-5 is set forth in SEQ ID NO.17, in particular:

```
(CD19 scFv)
atggattttcaggtgcagattttcagcttcctgctaatcagtgcctcagt cataatgtccagaggagacatccagatgacacagactacatcctccctgt ctgcctctctgggagacagagtcaccatcagttgcagggcaagtcaggac
```

-continued attagtaaatatttaaattggtatcagcagaaaccagatggaactgttaa actcctgatctaccatacatcaagattacactcaggagtcccatcaaggt tcagtggcagtgggtctggaacagattattctctcaccattagcaacctg gagcaagaagatattgccacttacttttgccaacagggtaatacgcttcc gtacacgttcggaggggggaccaagctggagatcacaggtggcggtggct cgggcggtggtgggtcgggtggcggcggatctgaggtgaaactgcaggag tcaggacctggcctggtggcgccctcacagagcctgtccgtcacatgcac tgtctcaggggtctcattacccgactatggtgtaagctggattcgccagc ctccacgaaagggtctggagtggctgggagtaatatggggtagtgaaacc acatactataattcagctctcaaatccagactgaccatcatcaaggacaa ctccaagagccaagttttcttaaaaatgaacagtctgcaaactgatgaca cagccatttactactgtgccaaacattattactacggtggtagctatgct atggactactgggccaaggaacctcagtcaccgtctcctca.

(V-4-5 hinge)
gactgttgattgggacatttaacgatcagaaacgtggcatctgtcgaccc tggacaaactgttctttggatggaaagtctgtgcttgtgaatgggacgaa ggagagggacgtggtctgtggaccatctccagccgacctctctccgggag catcctctgtgaccccgcctgcccctgcgagagagccaggacactctccg cag.

(CD28 TM)
tttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagccccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgccatcacatgcaggccctgccccctcgctaa.

In an embodiment, the CD19-V 3-4-5 is obtained by connecting the CD19 and the general sequence including the hinge domain V-3-4-5 in series; the nucleotide sequence of the CD19-V 3-4-5 is set forth in SEQ ID NO.18, in particular:

(CD19 scFv)
atggattttcaggtgcagattttcagcttcctgctaatcagtgcctcagt cataatgtccagaggagacatccagatgacacagactacatcctccctgt ctgcctctctgggagacagagtcaccatcagttgcagggcaagtcaggac attagtaaatatttaaattggtatcagcagaaaccagatggaactgttaa actcctgatctaccatacatcaagattacactcaggagtcccatcaaggt tcagtggcagtgggtctggaacagattattctctcaccattagcaacctg gagcaagaagatattgccacttacttttgccaacagggtaatacgcttcc gtacacgttcggaggggggaccaagctggagatcacaggtggcggtggct cgggcggtggtgggtcgggtggcggcggatctgaggtgaaactgcaggag tcaggacctggcctggtggcgccctcacagagcctgtccgtcacatgcac tgtctcaggggtctcattacccgactatggtgtaagctggattcgccagc ctccacgaaagggtctggagtggctgggagtaatatggggtagtgaaacc acatactataattcagctctcaaatccagactgaccatcatcaaggacaa ctccaagagccaagttttcttaaaaatgaacagtctgcaaactgatgaca cagccatttactactgtgccaaacattattactacggtggtagctatgct atggactactgggccaaggaacctcagtcaccgtctcctca.

(V-3-4-5 hinge)
gactgcactccagggtttcactgcctgggggcaggatgcagcatgtgtga acaggattgtaaacaaggtcaagaactgacaaaaaaaggttgtaaagact gttgattgggacatttaacgatcagaaacgtggcatctgtcgaccctgga caaactgttctttggatggaaagtctgtgcttgtgaatgggacgaaggag agggacgtggtctgtggaccatctccagccgacctctctccgggagcatc ctctgtgaccccgcctgcccctgcgagagagccaggacactctccgcag.

(CD28TM)
tttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagccccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccctgccccctcgctaa.

In an embodiment, the CD19-V 2-3-4-5 is obtained by connecting the CD19 and the general sequence including the hinge domain V-2-3-4-5; the nucleotide sequence of the CD19-V 2-3-4-5 is set forth in SEQ ID NO.19, in particular:

(CD19 scFv)
atggattttcaggtgcagattttcagcttcctgctaatcagtgcctcagt cataatgtccagaggagacatccagatgacacagactacatcctccctgt ctgcctctctgggagacagagtcaccatcagttgcagggcaagtcaggac attagtaaatatttaaattggtatcagcagaaaccagatggaactgttaa actcctgatctaccatacatcaagattacactcaggagtcccatcaaggt tcagtggcagtgggtctggaacagattattctctcaccattagcaacctg gagcaagaagatattgccacttacttttgccaacagggtaatacgcttcc gtacacgttcggaggggggaccaagctggagatcacaggtggcggtggct cgggcggtggtgggtcgggtggcggcggatctgaggtgaaactgcaggag tcaggacctggcctggtggcgccctcacagagcctgtccgtcacatgcac tgtctcaggggtctcattacccgactatggtgtaagctggattcgccagc ctccacgaaagggtctggagtggctgggagtaatatggggtagtgaaacc acatactataattcagctctcaaatccagactgaccatcatcaaggacaa ctccaagagccaagttttcttaaaaatgaacagtctgcaaactgatgaca cagccatttactactgtgccaaacattattactacggtggtagctatgct atggactactggggccaaggaacctcagtcaccgtctcctca.

(V-2-3-4-5 hinge)
agtccctgtcctccaaatagtttctccagcgcaggtggacaaaggacctg tgacatatgcaggcagtgtaaaggtgttttcaggaccaggaaggagtgtt cctccaccagcaatgcagagtgtgactgcactccagggtttcactgcctg ggggcaggatgcagcatgtgtgaacaggattgtaaacaaggtcaagaact gacaaaaaaggttgtaaagactgttgattgggacatttaacgatcagaa acgtggcatctgtcgaccctggacaaactgttattggatggaaagtctgt gatgtgaatgggacgaaggagagggacgtggtctgtggaccatctccagc cgacctctctccgggagcatcctctgtgacccgcctgcccctgcgagag agccaggacactctccgcag.

(CD28TM)
ttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg cccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagccccccgcgtaccagcagggcca gaaccagctctataacgagctcaatctaggacgaagagaggagtacgatg ttttggacaagagacgtggccgggaccctgagatgggggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccctgccccctcgctaa.

In an embodiment, the CD19-V 1-2-3-4-5 is obtained by connecting the CD19 and the general sequence including the hinge domain V-1-2-3-4-5; the nucleotide sequence of the CD19-V 1-2-3-4-5 is set forth in SEQ ID NO.20, in particular:

(CD19 scFv)
atggattttcaggtgcagattttcagcttcctgctaatcagtgcctcagt cataatgtccagaggagacatccagatgacacagactacatcctccctgt ctgcctctctgggagacagagtcaccatcagttgcagggcaagtcaggac attagtaaatatttaaattggtatcagcagaaaccagatggaactgttaa actcctgatctaccatacatcaagattacactcaggagtcccatcaaggt tcagtggcagtgggtctggaacagattattctctcaccattagcaacctg gagcaagaagatattgccacttacttttgccaacagggtaatacgcttcc gtacacgttcggaggggggaccaagctggagatcacaggtggcggtggct cgggcggtggtgggtcgggtggcggcggatctgaggtgaaactgcaggag tcaggacctggcctggtggcgccctcacagagcctgtccgtcacatgcac tgtctcaggggtctcattacccgactatggtgtaagctggattcgccagc ctccacgaaagggtctggagtggctgggagtaatatggggtagtgaaacc acatactataattcagctctcaaatccagactgaccatcatcaaggacaa ctccaagagccaagttttcttaaaaatgaacagtctgcaaactgatgaca cagccatttactactgtgccaaacattattactacggtggtagctatgct atggactactggggccaaggaacctcagtcaccgtctcctca.

(V-1-2-3-4-5 hinge)
ttgcaggatccttgtagtaactgcccagctggtacattctgtgataataa caggaatcagatttgcagtccctgtcctccaaatagtttctccagcgcag gtggacaaaggacctgtgacatatgcaggcagtgtaaaggtgttttcagg accaggaaggagtgttcctccaccagcaatgcagagtgtgactgcactcc agggtttcactgcctgggggcaggatgcagcatgtgtgaacaggattgta aacaaggtcaagaactgacaaaaaaggttgtaaagactgttgattggga catttaacgatcagaaacgtggcatctgtcgaccctggacaaactgttct ttggatggaaagtctgtgatgtgaatgggacgaaggagagggacgtggtc tgtggaccatctccagccgacctctctccgggagcatcctctgtgacccc gcctgcccctgcgagagagccaggacactctccgcag.

(CD28TM)
ttttgggtgctggtggtggttggtggagtcctggcttgctatagcttgct agtaacagtggcctttattattttctgggtg.

-continued (CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagcccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccagcccctcgctaa.

In an embodiment, in the case that the single chain antibody is GPC3, the chimeric antigen receptors includes GPC3-V 5, GPC3-V 4-5, GPC3-V 3-4-5, GPC3-V 2-3-4-5 and GPC3-V 1-2-3-4-5.

In the application, the GPC3-V 5 is obtained by connecting the GPC3 and the general sequence including the hinge domain V-5 in series; the nucleotide sequence of the GPC3-V 5 is set forth in SEQ ID NO.21, in particular:

(GPC3 scFv)
atggattttcaggtgcagattttcagcttcctgctaatcagtgcctcagt cataatgtccagaggagatgttgtgatgactcagtctccactctccctgc ccgtcacccctggagagccggcctccAtctcctgcagatctagtcagagc cttgtacacagtaatgccaacacctatttacattggtacctgcagaagcc agggcagtctccacagctcctgatctataaagtttccaaccgattttctg gggtccctgacaggttcagtggcagtggatcaggcacagattttacactg aaaatcagcagagtggaggctgaggatgttggggtttattactgctctca aaatacacatgttcctcctacgtttggccaggggaccaagctggagatca aacgtGgtggaggcggttcaggcggaggtggctctcaggtgcagctggtg cagtctggagctgaggtgaagaagcctggggcctcagtgaaggtctcctg caaggcttctggatacaccttcaccgactatgaaatgcactgggtgcgac aggcccctggacaagggcttgagtggatgggagctcttgatcctaaaact ggtgatactgcctacagtcagaagttcaagggcagagtcacgctgaccgc ggacgaatccacgagcacagcctacatggagctgagcagcctgagatctg aggacacggccgtgtattactgtacaagattctactcctatacttactgg ggccagggaaccctggtcaccgtctcctca.

(V-5 hinge)
ccatctccagccgacctctctccgggagcatcctctgtgaccccgcctgc ccctgcgagagagccaggacactctccgcag.

-continued (CD28 TM)
ttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagcccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgccatcacatgcaggccctgcccctcgctaa.

In an embodiment, the GPC3-V 4-5 is obtained by connecting the GPC3 and the general sequence including the hinge domain V-4-5 in series; the nucleotide sequence of the GPC3-V 4-5 is set forth in SEQ ID NO.22, in particular:

(GPC3 scFv)
atggattttcaggtgcagattttcagcttcctgctaatcagtgcctcagt cataatgtccagaggagatgttgtgatgactcagtctccactctccctgc ccgtcacccctggagagccggcctccAtctcctgcagatctagtcagagc cttgtacacagtaatgccaacacctatttacattggtacctgcagaagcc agggcagtctccacagctcctgatctataaagtttccaaccgattttctg gggtccctgacaggttcagtggcagtggatcaggcacagattttacactg aaaatcagcagagtggaggctgaggatgttggggtttattactgctctca aaatacacatgttcctcctacgtttggccaggggaccaagctggagatca aacgtGgtggaggcggttcaggcggaggtggctctcaggtgcagctggtg cagtctggagctgaggtgaagaagcctggggcctcagtgaaggtctcctg caaggcttctggatacaccttcaccgactatgaaatgcactgggtgcgac aggcccctggacaagggcttgagtggatgggagctcttgatcctaaaact ggtgatactgcctacagtcagaagttcaagggcagagtcacgctgaccgc ggacgaatccacgagcacagcctacatggagctgagcagcctgagatctg aggacacggccgtgtattactgtacaagattctactcctatacttactgg ggccagggaaccctggtcaccgtctcctca.

(V-4-5 hinge)
gactgttgattgggacatttaacgatcagaaacgtggcatctgtcgaccc tggacaaactgttctttggatggaaagtctgtgcttgtgaatgggacgaa ggagagggacgtggtctgtggaccatctccagccgacctctctccgggag -continued

```
catcctctgtgaccccgcctgccctgcgagagagccaggacactctccg cag.

(CD28 TM)
tttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagccccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgccatcacatgcaggccctgccccctcgctaa.
```

In an embodiment, the GPC3-V 3-4-5 is obtained by connecting the GPC3 and the general sequence including the hinge domain V-3-4-5 in series; the nucleotide sequence of the GPC3-V 3-4-5 is set forth in SEQ ID NO.23, in particular:

```
(GPC3 scFv)
atggattttcaggtgcagattttcagcttcctgctaatcagtgcctcagt cataatgtccagaggagatgttgtgatgactcagtctccactctccctgc ccgtcacccctggagagccggcctccAtctcctgcagatctagtcagagc cttgtacacagtaatgccaacacctatttacattggtacctgcagaagcc agggcagtctccacagctcctgatctataaagtttccaaccgattttctg ggtccctgacaggttcagtggcagtggatcaggcacagattttacactg aaaatcagcagagtggaggctgaggatgttggggtttattactgctctca aaatacacatgttcctcctacgtttggccaggggaccaagctggagatca aacgtGgtggaggcggttcaggcggaggtggctctcaggtgcagctggtg cagtctggagctgaggtgaagaagcctggggcctcagtgaaggtctcctg caaggcttctggatacaccttcaccgactatgaaatgcactgggtgcgac aggcccctggacaagggcttgagtggatgggagctcttgatcctaaaact ggtgatactgcctacagtcagaagttcaagggcagagtcacgctgaccgc ggacgaatccacgagcacagcctacatggagctgagcagcctgagatctg aggacacggccgtgtattactgtacaagattctactcctatacttactgg ggccagggaaccctggtcaccgtctcctca.

(V-3-4-5 hinge)
gactgcactccagggtttcactgcctggggcaggatgcagcatgtgtga acaggattgtaaacaaggtcaagaactgacaaaaaaaggttgtaaagact gttgattgggacatttaacgatcagaaacgtggcatctgtcgaccctgga caaactgttctttggatggaaagtctgtgcttgtgaatgggacgaaggag agggacgtggtctgtggaccatctccagccgacctctctcgggagcatc ctctgtgaccccgcctgcccctgcgagagagccaggacactctccgcag.

(CD28TM)
tttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagccccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgccttcacatgcaggccctgccccctcgctaa.
```

In an embodiment, the GPC3-V 2-3-4-5 is obtained by connecting the GPC3 and the general sequence including the hinge domain V-2-3-4-5 in series; the nucleotide sequence of the GPC3-V 2-3-4-5 is set forth in SEQ ID NO.24, in particular:

```
(GPC3 scFv)
atggattttcaggtgcagattttcagcttcctgctaatcagtgcctcagt cataatgtccagaggagatgttgtgatgactcagtctccactctccctgc ccgtcacccctggagagccggcctccatctcctgcagatctagtcagagc cttgtacacagtaatgccaacacctatttacattggtacctgcagaagcc agggcagtctccacagctcctgatctataaagtttccaaccgattttctg ggtccctgacaggttcagtggcagtggatcaggcacagattttacactg aaaatcagcagagtggaggctgaggatgttggggtttattactgctctca aaatacacatgttcctcctacgtttggccaggggaccaagctggagatca aacgtggtggaggcggttcaggcggaggtggctctcaggtgcagctggtg cagtctggagctgaggtgaagaagcctggggcctcagtgaaggtctcctg caaggcttctggatacaccttcaccgactatgaaatgcactgggtgcgac aggcccctggacaagggcttgagtggatgggagctcttgatcctaaaact
```

-continued
ggtgatactgcctacagtcagaagttcaagggcagagtcacgctgaccgc ggacgaatccacgagcacagcctacatggagctgagcagcctgagatctg aggacacggccgtgtattactgtacaagattctactcctatacttactgg ggccagggaaccctggtcaccgtctcctca.

(V-2-3-4-5 hinge)
agtccctgtcctccaaatagtttctccagcgcaggtggacaaaggacctg tgacatatgcaggcagtgtaaaggtgttttcaggaccaggaaggagtgtt cctccaccagcaatgcagagtgtgactgcactccagggtttcactgcctg ggggcaggatgcagcatgtgtgaacaggattgtaaacaaggtcaagaact gacaaaaaaggttgtaaagactgttgattgggacatttaacgatcagaa acgtggcatctgtcgaccctggacaaactgttattggatggaaagtctgt gatgtgaatgggacgaaggagagggacgtggtctgtggaccatctccagc cgacctctctccgggagcatcctctgtgaccccgcctgcccctgcgagag agccaggacactctccgcag.

(CD28TM)
tttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagccccccgcgtaccagcagggcca gaaccagctctataacgagctcaatctaggacgaagagaggagtacgatg ttttggacaagagacgtggccgggaccctgagatgggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccctgcccctcgctaa.

In an embodiment, the GPC3-V 1-2-3-4-5 is obtained by connecting the GPC3 and the general sequence including the hinge domain V-1-2-3-4-5 in series; the nucleotide sequence of the GPC3-V 1-2-3-4-5 is set forth in SEQ ID NO.25, in particular:

(GPC3 scFv)
atggattttcaggtgcagattttcagcttcctgctaatcagtgcctcagt cataatgtccagaggagatgttgtgatgactcagtctccactctccctgc ccgtcacccctggagagccggcctccatctcctgcagatctagtcagagc cttgtacacagtaatgccaacacctatttacattggtacctgcagaagcc agggcagtctccacagctcctgatctataaagtttccaaccgattttctg gggtccctgacaggttcagtggcagtggatcaggcacagattttacactg aaaatcagcagagtggaggctgaggatgttgggghtttattactgctctca aaatacacatgttcctcctacgtttggccaggggaccaagctggagatca aacgtggtggaggcggttcaggcggaggtggctctcaggtgcagctggtg cagtctggagctgaggtgaagaagcctggggcctcagtgaaggtctcctg caaggcttctggatacaccttcaccgactatgaaatgcactgggtgcgac aggcccctggacaagggcttgagtggatgggagctcttgatcctaaaact ggtgatactgcctacagtcagaagttcaagggcagagtcacgctgaccgc ggacgaatccacgagcacagcctacatggagctgagcagcctgagatctg aggacacggccgtgtattactgtacaagattctactcctatacttactgg ggccagggaaccctggtcaccgtctcctca.

(V-1-2-3-4-5 hinge)
ttgcaggatccttgtagtaactgcccagctggtacattctgtgataataa caggaatcagatttgcagtccctgtcctccaaatagtttctccagcgcag gtggacaaaggacctgtgacatatgcaggcagtgtaaaggtgttttcagg accaggaaggagtgttcctccaccagcaatgcagagtgtgactgcactcc agggtttcactgcctgggggcaggatgcagcatgtgtgaacaggattgta aacaaggtcaagaactgacaaaaaaggttgtaaagactgttgattggga catttaacgatcagaaacgtggcatctgtcgaccctggacaaactgttct tggatggaaagtctgtgatgtgaatgggacgaaggagagggacgtggtc tgtggaccatctccagccgacctctctccgggagcatcctctgtgacccc gcctgcccctgcgagagagccaggacactctccgcag.

(CD28TM)
tttttgggtgctggtggtggttggtggagtcctggcttgctatagcttgct agtaacagtggcctttattattttctgggtg.

(CD28)
aggagtaagag gagcaggctc ctgcacagtg actacatgaa catgactccc cgccgccccg ggcccacccg caagcattac cagccctatg ccccaccacg cgacttcgca gcctatcgct cc.

(4-1BB)
aaacggggcagaaagaaactcctgtatatattcaaacaaccatttatgag accagtacaaactactcaagaggaagatggctgtagctgccgatttccag aagaagaagaaggaggatgtgaactg.

(CD3 ζ)
agagtgaagttcagcaggagcgcagagccccccgcgtaccagcagggcca gaaccagctctataacgagctcaatctaggacgaagagaggagtacgatg ttttggacaagagacgtggccgggaccagagatgggggaaagccgagaa ggaagaaccctcaggaaggcctgtacaatgaactgcagaaagataagatg gcggaggcctacagtgagattgggatgaaaggcgagcgccggaggggcaa ggggcacgatggcctttaccagggtctcagtacagccaccaaggacacct acgacgcccttcacatgcaggccagccccctcgctaa.

The application provides a drug for improving the antigen-specific immune response of immune cells and/or an anti-tumor agent, wherein the active components of the drug include the general sequence of the chimeric antigen receptor of the above schemes.

In the specific implementation of embodiments, the exemplary chimeric antigen receptor and the general sequence thereof are synthesized by Sangon Biotech.

In an embodiment, as compared with the CAR structure having a traditional hinge domain, the CAR structure having the hinge domain of the embodiments can significantly improve the antigen-specific immune response of CAR-T cells, enhance the sensitivity of CAR-T cells and resist exhaustion, so as to enhance the therapeutic effect of CAR-T cells and enhance the therapeutic effect of anti-tumor agent.

The technical solutions provided by the application will be described in detail with reference to examples, but they do not limit the scope of the claimed invention.

Example 1

Figure 3:
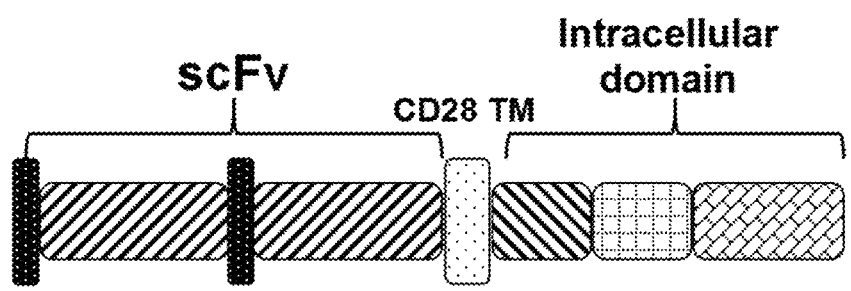
FIG. 3 shows the structural diagram of No-H.
Figure 4:
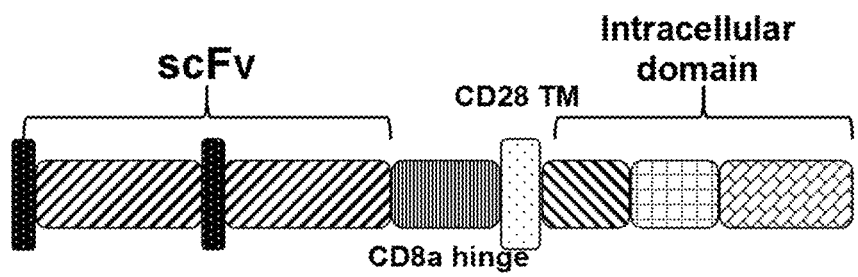
FIG. 4 shows the structural diagram of CD8a-H.
Figure 5:
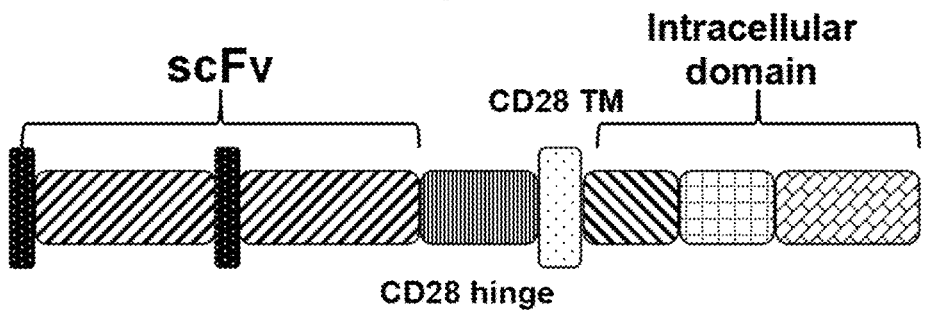
FIG. 5 shows the structural diagram of CD28-H.
Figure 6:
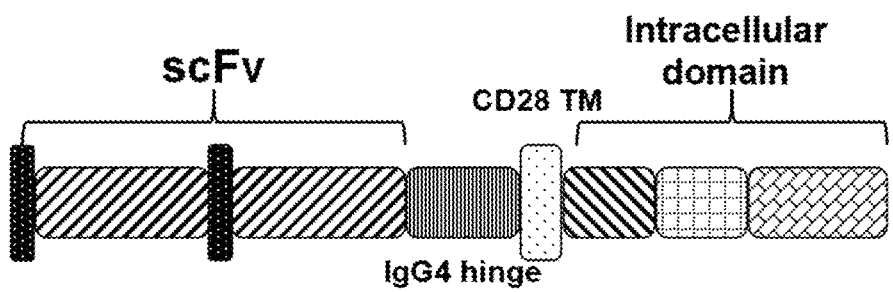
FIG. 6 shows the structural diagram of IgG4-H.

1. The corresponding target genes are synthesized by Shanghai Sangon Biotech according to the nucleic acid sequence. The target genes include:
HER2-CAR, which comprises:
a: HER2-V 5, SEQ ID NO.11;
b: HER2-V 4-5, SEQ ID NO.12;
c: HER2-V 3-4-5, SEQ ID NO.13;
d: HER2-V 2-3-4-5, SEQ ID NO.14; or
e: HER2-V 1-2-3-4-5, SEQ ID NO.15;
CD19-CAR, which comprises:
f: CD19-V 5, SEQ ID NO.16;
g: CD19-V 4-5, SEQ ID NO.17;
h: CD19-V 3-4-5, SEQ ID NO.18;
i: CD19-V 2-3-4-5, SEQ ID NO.19; or
j: CD19-V 1-2-3-4-5, SEQ ID NO.20;
GPC3-CAR, which comprises:
k: GPC3-V 5, SEQ ID NO.21;
l: GPC3-V 4-5, SEQ ID NO.22;
m: GPC3-V 3-4-5, SEQ ID NO.23;
n: GPC3-V 2-3-4-5, SEQ ID NO.24; or
o: GPC3-V 1-2-3-4-5, SEQ ID NO.25;
A control sequence comprising:
p: the structural diagram of No-H is shown in FIG. 3. The hinge domain of the general sequence of the chimeric antigen receptor of the present application was deleted, and other parts were consistent with the general sequence of the present application. In a specific implementation process, the No-H was respectively connected in series with HER2, GPC3 and CD19 single chain antibody sequences according to the structure shown in FIG. 3 to form the corresponding CAR, and a comparison test was conducted;
q: the structural diagram of CD8a-H is shown in FIG. 4. The hinge domain of the general sequence of the chimeric antigen receptor of the present application was replaced with the following hinge domain (SEQ ID NO.29): accacgacgccagcgccgcgaccaccaacaccggcgcc-caccatcgcgtcgcagcccctgtccctgcgcccagaggcgtgccggc-cagcggcggggggcgcagtgcacacgagggggctggacttcgcctgt-gat, and other parts were consistent with the general sequence of the present application. In a specific implementation process, the CD8a-H was respectively connected in series with HER2, GPC3 and CD19 single chain antibody sequences according to the structure shown in FIG. 4 to form the corresponding CAR, and a comparison test was conducted;
r: the structural diagram of CD28-H is shown in FIG. 5. The hinge domain of the general sequence of the chimeric antigen receptor of the present application was replaced with the following hinge domain (SEQ ID NO.30): gatatttacttctgcaaaattgaagttatgtatcctcctcct-tacctagacaatgagaagagcaatggaaccattatccatgtgaaagg-gaaacaccttttgtccaagtcccctatttcccggaccttctaagccc, and other parts were consistent with the general sequence of the present application. In a specific implementation process, the CD28-H was respectively connected in series with HER2, GPC3 and CD19 single chain antibody sequences according to the structure shown in FIG. 5 to form the corresponding CAR, and a comparison test was conducted;
s: the structural diagram of IgG4-H is shown in FIG. 6, The hinge domain of the general sequence of the chimeric antigen receptor of the present application was replaced with the following hinge domain (SEQ ID NO.31): taaagccaaagggcagccccgagaaccacaggtgta-caccctgcccccatcccgggatgagctgaccaagaaccaggtcagcct-gacctgcctggtcaaaggatctatcccagcgacatcgccgtggagtgg-gagagcaatgggcagccggagaacaactacaagaccacgcctccc-gtgctggactccgacggctccttcttcctctacagcaagctcaccgtggaca-agagcaggtggcagcaggggaacgtcttctcatgctccgtgatgcat-gaggctctgcacaaccactacacgcagaagagcctctcc, and other parts were consistent with the general sequence of the present application. In the specific implementation process, the IgG4-H was respectively connected in series with HER2, GPC3 and CD19 single chain antibody sequences according to the structure shown in FIG. 6 to form the corresponding CAR, and a comparison test was conducted;
t: blank control (Non-transduced);

The target gene was ligated into the vector pGEM4Z/GFP/A64 by gene cloning, the GFP gene was cut out with two enzymes, Not I and Hind III of neb, and then the above targets gene were inserted into the vector.

2. Preparation of mRNA: The plasmid was cut with SpeI of neb, overnight. The enzyme digestion product was purified using the QIAquick PCR Purification Kit (QIAGEN), and RNA was prepared using the kit of T7 mScript™ Standard mRNA Production System (CELLSCRIPT™).

3. Preparation of T cells: The concentration of mononuclear cells isolated from peripheral blood of healthy people was adjusted to $1\times10^6$/mL, which was placed in a 24-well plate, 1 mL/well. The culture conditions were: 5 µg/mL anti-hCD3 (pre-coated), 2 µg/mL anti-hCD28. Five days later, the anti-hCD3/28 stimulation was removed, and 40 ng/mL (100 U/mL) maintenance dose of rmIL-2 was given. The medium was supplemented every 2 days according to the cell concentration. When the volume of T cells were reduced to less than 8 µm after 9 to 11 days, the cells were stored frozen for future use.

4. Electrotransfection of RNA into T cells: first, the cells were washed with cold Opti-MEM for three times, and resuspended at the appropriate concentration (20~300×$10^6$/mL); then 100 L cell suspension was mixed with 5~10 µg RNA, and added into 0.2M electrotransfection cuvettes. Electrotransfection conditions: 500 uv 700 us (stimulated T cells), 500 uv 800 us (resting T cells), 500 uv 500 us (tumor cells); The cells after electrotransfection were quickly transferred into the preheated 1640 complete medium.

Figure 7:
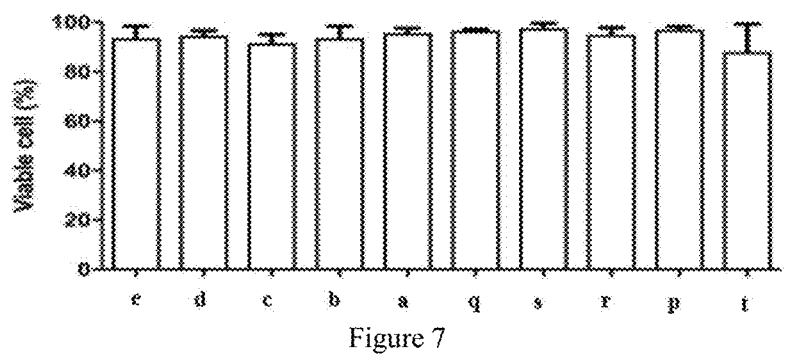
FIG. 7 shows the viability of T cell targeting HER2-CAR after electrotransfection.
Figure 8:
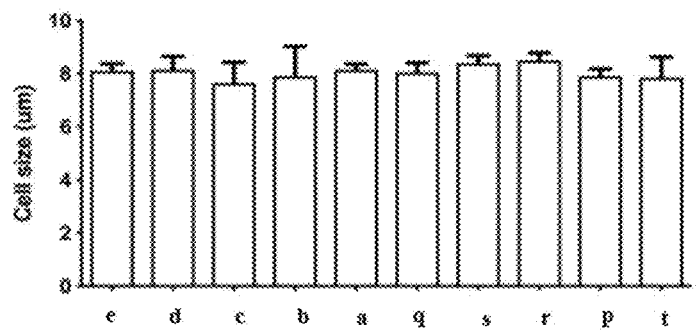
FIG. 8 shows the size of T cell targeting HER2-CAR after electrotransfection.
Figure 9:
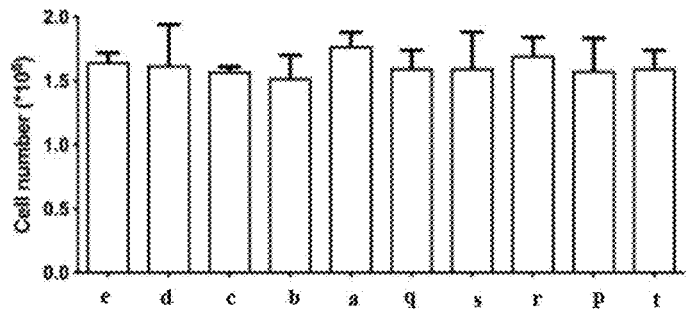
FIG. 9 shows the number of T cells targeting HER2-CAR after electrotransfection.

5. After RNA electrotransfection, functional evaluation were performed.
5.1 HER2-CAR electrotransfection (respectively HER2-V 5, HER2-V 4-5, HER2-V 3-4-5, HER2-V 2-3-4-5, HER2-V 1-2-3-4-5) was conducted for 24 hours, the cell counter from Thermo Fisher was used to measure the viability, size and the number of T cells. The measurement results are shown in FIGS. 7 to 9. FIG. 7 shows the viability of T cells targeting HER2-CAR after electrotransfection; FIG. 8 shows the size of T cell targeting HER2-CAR after electrotransfection. FIG. 9 shows the number of T cells targeting HER2-CAR after electrotransfection. FIGS. 7 to 9 that the electrotransfection targeting HER2-CAR does not affect the viability, diameter and the number of T cells.

Figure 10:
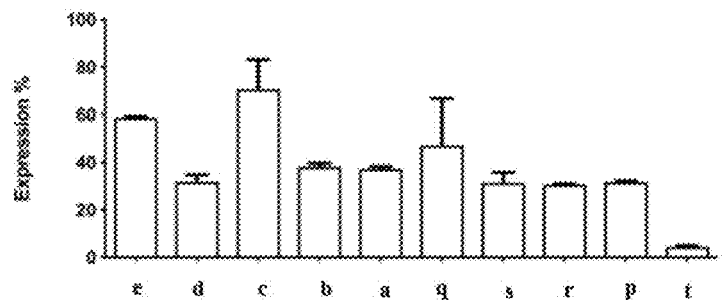
FIG. 10 shows the expression level of T cells targeting HER2-CAR after electrotransfection.

5.2 HER2-CAR electrotransfection (respectively HER2-V 5, HER2-V 4-5, HER2-V 3-4-5, HER2-V 2-3-4-5, HER2-V 1-2-3-4-5) was conducted for 24 hours. The cells were stained with fluorescently labeled antibody and then the expression of HER2-CAR on the surface of T cells in each group was measured with a flow cytometer. FIG. 10 shows the measurement results. It can be seen from FIG. 10 shows that different hinge domains affect the expressions of CAR, with HER2-V 3-4-5 being the highest.

Figure 11:
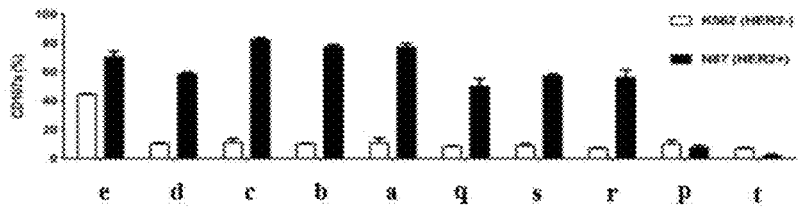
FIG. 11 shows the CD107a membrane translocation level of HER2-CAR-T cells.

5.3 HER2-CAR RNA electrotransfection (respectively HER2-V 5 RNA, HER2-V 4-5 RNA, HER2-V 3-4-5 RNA, HER2-V 2-3-4-5 RNA, HER2-V 1-2-3-4-5 RNA) was conducted for 24 hours T cells in each group were incubated with K562 (HER2 negative) tumor cells and N87 (HER2 positive) tumor cells at a 1:4 ratio for 4 hours to detect the membrane translocation of CD107a on the surface of T cells. FIG. 11 shows the test results. The results showed that except for the HER2-V 1-2-3-4-5 RNA group, when co-incubated with K562 (HER2 negative) tumor cells, only low levels of CD107a membrane translocation were detected on the surface of T cells in each group. However, when co-incubated with N87 (HER2-positive) tumor cells, high levels of CD107a membrane translocation were detected in T cells transfected with HER2 CAR RNA (excluding No-H group) when compared with T cells without RNA transfection, and the No-H group is similar to the T cell group without electrotransfection.

Figure 12:
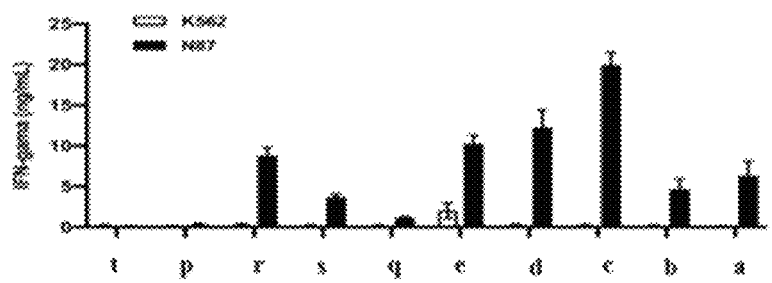
FIG. 12 shows the IFN-γ secretion of HER2-CAR-T cells.
Figure 13:
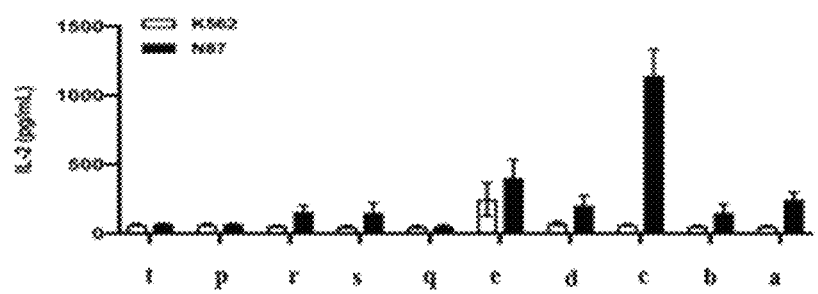
FIG. 13 shows the IL-2 secretion of HER2-CAR-T cells.

5.4 HER2-CAR RNA electrotransfection (respectively HER2-V 5 RNA, HER2-V 4-5 RNA, HER2-V 3-4-5 RNA, HER2-V 2-3-4-5 RNA, HER2-V 1-2-3-4-5 RNA) was conducted for 24 hours. T cells in each group were incubated with K562 (HER2 negative) tumor cells and N87 (HER2 positive) tumor cells at a 1:1 ratio for 24 hours to detect the secretion of IFN-γ and IL-2. FIG. 12 and FIG. 13 show the test results. FIG. 12 shows the IFN-γ secretion of HER2-CAR-T cells; FIG. 13 shows the IL-2 secretion of HER2-CAR-T cells. The results showed that compared with the K562 (HER2 negative) group, T cells in the HER2 CAR RNA group (excluding No-H group) secreted higher IFN-γ, and the HER2-V 3-4-5 RNA group secreted higher IL-2, No-H group is similar to the T cell group without electrotransfection.

5.5 GPC3-CAR RNA electrotransfection (respectively GPC3-V 5 RNA, GPC3-V 4-5 RNA, GPC3-V 3-4-5 RNA, GPC3-V 2-3-4-5 RNA, GPC3-V 1-2-3-4-5 RNA) was conducted for 24 hours. CD107a membrane translocation and cytokine secretion were detected. Huh7 cells were GPC3 positive. K562 cell were GPC3 negative. The results are shown in FIGS. 14 to 16. FIG. 14 shows the CD107a membrane translocation level of GPC3-CAR-T cells. FIG. 15 shows the IFN-γ secretion of GPC3-CAR-T cells. FIG. 16 shows the IL-2 secretion of GPC3-CAR-T cells. As can be seen from FIG. 14 to FIG. 16, all GPC3-CAR-T have good specificity, recognizing the GPC3-positive tumor of Huh7. The activation level of GPC3-V 3-4-5 RNA containing the hinge domain V-3-4-5 is higher, with high secretion of cytokines (IL-2, IFN-γ) and the optimal killing effect (CD107a membrane translocation).

Figure 17:
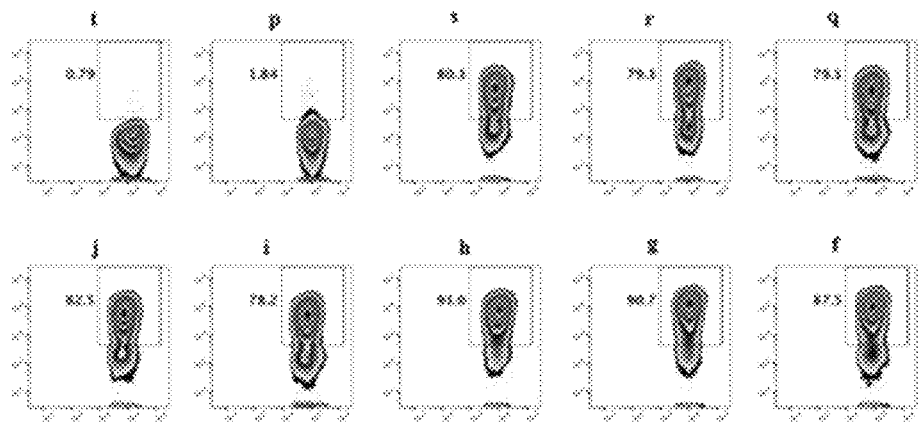

5.6 CD19-CAR RNA electrotransfection (respectively CD19-V 5 RNA, CD19-V 4-5 RNA, CD19-V 3-4-5 RNA, CD19-V 2-3-4-5 RNA, CD19-V 1-2-3-4-5 RNA) was conducted for 24 hours. CD107a membrane translocation and cytokine secretion were detected. Ramos cells were CD19 positive, and K562 cells were CD19 negative. The results are shown in FIGS. 17~19. wherein FIG. 17 shows the CD107a membrane translocation level of CD19-CAR-T cells. FIG. 18 shows the IFN-γ secretion of CD19-CAR-T cells. FIG. 19 shows the IL-2 secretion of CD19-CAR-T cells. It can be seen from FIGS. 20~22 that, consistent with the results of HER2-CAR and GPC3-CAR, hinge domain V-3-4-5 renders CD19-CAR-T cells a higher activation level and killing effect.

5.7 After electrotransfection of HER2-V 3-4-5 RNA, it was stimulated by different doses of purified HER2 antigen, and the sensitivity of the optimized hinge domain (v-3-4-5) to antigenic stimulation was tested. The most widely used conventional hinge domain (CD8-H) and No-H (hinge domain removed) were set as controls. The results are shown in FIG. 20, FIG. 21, and FIG. 22. FIG. 20 shows the cytokine TNF-α secretion of CAR-T cells stimulated by different concentrations of antigens (3 g/mL, 1 g/mL and 0 g/mL). FIG. 21 shows the cytokine IFN-γ secretion of CAR-T cells stimulated by different concentrations of antigens. FIG. 22 shows the difference of activation level of CAR-T cells stimulated by different concentrations of antigens (CD25 expression). The results confirmed that HER2-V 3-4-5 RNA as one in hinge group maintained a high level of immunoreactivity under low-dose antigen stimulation, suggesting that the new hinge domain significantly enhanced the sensitivity of CAR-T cells to antigen responses.

5.8 HER2-CAR RNA electrotransfection (respectively HER2-V 5 RNA, HER2-V 4-5 RNA, HER2-V 3-4-5 RNA, HER2-V 2-3-4-5 RNA, HER2-V 1-2-3-4-5 RNA) was conducted, co-cultured with antigen-positive tumor cells for 48 h, and then the downstream signaling (pSTAT1, pSTAT5) and surface exhaustion markers (PD-1, TIM3) after CAR-T activation were detected. The effects of different hinge domains on the exhaustion of CAR-T cells were compared. The results are shown in FIGS. 23 to 25. FIG. 23 shows the downstream signal transduction (pSTAT1) after CAR-T cell activation. FIG. 24 shows the downstream signal transduction (pSTAT5) after CAR-T cell activation. FIG. 25 shows the expression level of exhaustion markers (PD-1, TIM3) on the surface of CAR-T cells. The results confirmed that the hinge domain in HER2-V 3-4-5 RNA, not only effectively enhances the activation of CAR-T cells, but also maintains its persistence showing a relatively low level of exhaustion marker expression.

The above is only the preferred embodiment of the present invention. It should be pointed out that for those of ordinary skill in the art, without departing from the principles of the present invention, several improvements and retouches can be made. These improvements and retouches should be regarded as the protection scope of the present invention.

What is claimed is:

1. A general sequence of chimeric antigen receptor, wherein a hinge domain comprises a general sequence selected from the group consisting of a hinge domain V-5, a hinge domain V-4-5, a hinge domain V-3-4-5, a hinge domain V-2-3-4-5 or a hinge domain V-1-2-3-4-5; wherein
the nucleotide sequence of the hinge domain V-5 is set forth in SEQ ID NO.1;
the nucleotide sequence of the hinge domain V-4-5 is set forth in SEQ ID NO.2;
the nucleotide sequence of the hinge domain V-3-4-5 is set forth in SEQ ID NO.3;
the nucleotide sequence of the hinge domain V-2-3-4-5 is set forth in SEQ ID NO.4;
the nucleotide sequence of the hinge domain V-1-2-3-4-5 is set forth in SEQ ID NO.5;
the nucleotide sequence of the general sequence comprising the hinge domain V-5 is set forth in SEQ ID NO.6;
the nucleotide sequence of the general sequence comprising the hinge domain V-4-5 is set forth in SEQ ID NO.7;
the nucleotide sequence of the general sequence comprising the hinge domain V-3-4-5 is set forth in SEQ ID NO.8;
the nucleotide sequence of the general sequence comprising the hinge domain V-2-3-4-5 is set forth in SEQ ID N0.9; and
the nucleotide sequence of the general sequence comprising the hinge domain V-1-2-3-4-5 is set forth in SEQ ID NO.10.

2. A chimeric antigen receptor comprising the general sequence of claim 1, wherein the chimeric antigen receptor is obtained by connecting a single chain antibody and the general sequence in series; wherein the single chain antibody is selected from the group consisting of HER2, CD19, and GPC;

wherein the single chain antibody is HER2, and the chimeric antigen receptors are selected from the group consisting of HER2-V-5, HER2-V-4-5, HER2 V-3-4-5, HER2-2-3-4-5 and HER2-V-1-2-3-4-5; wherein
the nucleotide sequence of HER2-V-5 is set forth in SEQ ID NO:11;
the nucleotide sequence of HER2-V-4-5 is set forth in SEQ ID NO:12;
the nucleotide sequence of HER2-V-3-4-5 is set forth in SEQ ID NO:13;
the nucleotide sequence of HER2-V-2-3-4-5 is set forth in SEQ ID NO:14;
the nucleotide sequence of HER2-V-1-2-3-4-5 is set forth in SEQ ID NO:15;
wherein the single chain antibody is CD19, and the chimeric antigen receptors are selected from the group consisting of CD19-V-5, CD19-V-4-5, CD19 V-3-4-5, CD19-2-3-4-5 and CD19-V-1-2-3-4-5; wherein
the nucleotide sequence of CD19-V-5 is set forth in SEQ ID NO:16;
the nucleotide sequence of CD19-V-4-5 is set forth in SEQ ID NO:17;
the nucleotide sequence of CD19-V-3-4-5 is set forth in SEQ ID NO:18;
the nucleotide sequence of CD19-V-2-3-4-5 is set forth in SEQ ID NO:19;
the nucleotide sequence of CD19-V-1-2-3-4-5 is set forth in SEQ ID NO: 20; or
wherein the single chain antibody is GPC3, and the chimeric antigen receptors are selected from the group consisting of GPC3-V-5, GPC3-V-4-5, GPC3 V-3-4-5, GPC3-2-3-4-5 and GPC3-V-1-2-3-4-5; wherein
the nucleotide sequence of GPC3-V-5 is set forth in SEQ ID NO:21;
the nucleotide sequence of GPC3-V-4-5 is set forth in SEQ ID NO:22;

the nucleotide sequence of GPC3-V-3-4-5 is set forth in SEQ ID NO:23;

the nucleotide sequence of GPC3-V-2-3-4-5 is set forth in SEQ ID NO:24;

the nucleotide sequence of GPC3-V-1-2-3-4-5 is set forth in SEQ ID NO:25.

3. A drug for improving the antigen-specific immune response of immune cells and promoting an anti-tumor effect, wherein the active components of the drug comprise the general sequence of the chimeric antigen receptor of claim 1.

* * * * *

SEQUENCE LISTING

<160> NUMBER OF SEQ ID NOS: 31

<210> SEQ ID NO 1
<211> LENGTH: 81
<212> TYPE: DNA
<213> ORGANISM: Artificial Sequence
<220> FEATURE:
<223> OTHER INFORMATION: hinge domain V-5

<400> SEQUENCE: 1

```
ccatctccag ccgacctctc tccgggagca tcctctgtga ccccgcctgc ccctgcgaga    60
gagccaggac actctccgca g                                              81
```

<210> SEQ ID NO 2
<211> LENGTH: 204
<212> TYPE: DNA
<213> ORGANISM: Artificial Sequence
<220> FEATURE:
<223> OTHER INFORMATION: hinge domain V-4-5

<400> SEQUENCE: 2

```
gactgttgct ttgggacatt taacgatcag aaacgtggca tctgtcgacc ctggacaaac    60
tgttctttgg atggaaagtc tgtgcttgtg aatgggacga aggagaggga cgtggtctgt   120
ggaccatctc cagccgacct ctctccggga gcatcctctg tgaccccgcc tgcccctgcg   180
agagagccag gacactctcc gcag                                          204
```

<210> SEQ ID NO 3
<211> LENGTH: 300
<212> TYPE: DNA
<213> ORGANISM: Artificial Sequence
<220> FEATURE:
<223> OTHER INFORMATION: hinge domain V-3-4-5

<400> SEQUENCE: 3

```
gactgcactc cagggtttca ctgcctgggg gcaggatgca gcatgtgtga acaggattgt    60
aaacaaggtc aagaactgac aaaaaaaggt tgtaaagact gttgctttgg gacatttaac   120
gatcagaaac gtggcatctg tcgaccctgg acaaactgtt ctttggatgg aaagtctgtg   180
cttgtgaatg ggacgaagga gagggacgtg gtctgtggac catctccagc cgacctctct   240
ccgggagcat cctctgtgac cccgcctgcc cctgcgagag agccaggaca ctctccgcag   300
```

<210> SEQ ID NO 4
<211> LENGTH: 423
<212> TYPE: DNA
<213> ORGANISM: Artificial Sequence
<220> FEATURE:
<223> OTHER INFORMATION: hinge domain V-2-3-4-5

<400> SEQUENCE: 4

```
agtccctgtc ctccaaatag tttctccagc gcaggtggac aaaggacctg tgacatatgc    60
aggcagtgta aggtgttttt caggaccagg aaggagtgtt cctccaccag caatgcagag   120
tgtgactgca ctccagggtt tcactgcctg ggggcaggat gcagcatgtg tgaacaggat   180
tgtaaacaag gtcaagaact gacaaaaaaa ggttgtaaag actgttgctt tgggacattt   240
aacgatcaga aacgtggcat ctgtcgaccc tggacaaact gttctttgga tggaaagtct   300
gtgcttgtga atgggacgaa ggagagggac gtggtctgtg gaccatctcc agccgacctc   360
tctccgggag catcctctgt gaccccgcct gcccctgcga gagagccagg acactctccg   420
cag                                                                 423
```

<210> SEQ ID NO 5
<211> LENGTH: 489
<212> TYPE: DNA
<213> ORGANISM: Artificial Sequence
<220> FEATURE:
<223> OTHER INFORMATION: hinge domain V-1-2-3-4-5

<400> SEQUENCE: 5

| | | | | | |
|---|---|---|---|---|---|
| ttgcaggatc | cttgtagtaa | ctgcccagct | ggtacattct | gtgataataa | caggaatcag | 60 |
| atttgcagtc | cctgtcctcc | aaatagtttc | tccagcgcag | gtggacaaag | gacctgtgac | 120 |
| atatgcaggc | agtgtaaagg | tgttttcagg | accaggaagg | agtgttcctc | caccagcaat | 180 |
| gcagagtgtg | actgcactcc | agggtttcac | tgcctggggg | caggatgcag | catgtgtgaa | 240 |
| caggattgta | acaaggtca | agaactgaca | aaaaaggtt | gtaaagactg | ttgctttggg | 300 |
| acatttaacg | atcagaaacg | tggcatctgt | cgaccctgga | caaactgttc | tttggatgga | 360 |
| aagtctgtgc | ttgtgaatgg | gacgaaggag | agggacgtgg | tctgtggacc | atctccagcc | 420 |
| gacctctctc | cgggagcatc | ctctgtgacc | ccgcctgccc | ctgcgagaga | gccaggacac | 480 |
| tctccgcag | | | | | | 489 |

<210> SEQ ID NO 6
<211> LENGTH: 750
<212> TYPE: DNA
<213> ORGANISM: Artificial Sequence
<220> FEATURE:
<223> OTHER INFORMATION: hinge domain V-5

<400> SEQUENCE: 6

| | | | | | |
|---|---|---|---|---|---|
| ccatctccag | ccgacctctc | tccgggagca | tcctctgtga | ccccgcctgc | ccctgcgaga | 60 |
| gagccaggac | actctccgca | gttttgggtg | ctggtggtgg | ttggtggagt | cctggcttgc | 120 |
| tatagcttgc | tagtaacagt | ggcctttatt | attttctggg | tgaggagtaa | gaggagcagg | 180 |
| ctcctgcaca | gtgactacat | gaacatgact | ccccgccgcc | ccgggcccac | ccgcaagcat | 240 |
| taccagccct | atgccccacc | acgcgacttc | gcagcctatc | gctccaaacg | ggcagaaaag | 300 |
| aaactcctgt | atatattcaa | acaaccattt | atgagaccag | tacaaactac | tcaagaggaa | 360 |
| gatggctgta | gctgccgatt | tccagaagaa | gaagaaggag | gatgtgaact | gagagtgaag | 420 |
| ttcagcagga | gcgcagagcc | ccccgcgtac | cagcagggcc | agaaccagct | ctataacgag | 480 |
| ctcaatctag | gacgaagaga | ggagtacgat | gttttggaca | agagacgtgg | ccgggaccct | 540 |
| gagatggggg | gaaagccgag | aaggaagaac | cctcaggaag | gcctgtacaa | tgaactgcag | 600 |
| aaagataaga | tggcggaggc | ctacagtgag | attgggatga | aggcgagcg | ccggaggggc | 660 |
| aaggggcacg | atggccttta | ccagggtctc | agtacagcca | ccaaggacac | ctacgacgcc | 720 |
| cttcacatgc | aggccctgcc | ccctcgctaa | | | | 750 |

<210> SEQ ID NO 7
<211> LENGTH: 873
<212> TYPE: DNA
<213> ORGANISM: Artificial Sequence
<220> FEATURE:
<223> OTHER INFORMATION: hinge domain V-4-5

<400> SEQUENCE: 7

| | | | | | |
|---|---|---|---|---|---|
| gactgttgct | ttgggacatt | taacgatcag | aaacgtggca | tctgtcgacc | ctggacaaac | 60 |
| tgttctttgg | atggaaagtc | tgtgcttgtg | aatgggacga | aggagaggga | cgtggtctgt | 120 |

| | |
|---|---|
| ggaccatctc cagccgacct ctctccggga gcatcctctg tgaccccgcc tgcccctgcg | 180 |
| agagagccag gacactctcc gcagttttgg gtgctggtgg tggttggtgg agtcctggct | 240 |
| tgctatagct tgctagtaac agtggccttt attattttct gggtgaggag taagaggagc | 300 |
| aggctcctgc acagtgacta catgaacatg actccccgcc gccccgggcc cacccgcaag | 360 |
| cattaccagc cctatgcccc accacgcgac ttcgcagcct atcgctccaa acggggcaga | 420 |
| aagaaactcc tgtatatatt caaacaacca tttatgagac cagtacaaac tactcaagag | 480 |
| gaagatggct gtagctgccg atttccagaa gaagaagaag gaggatgtga actgagagtg | 540 |
| aagttcagca ggagcgcaga gccccccgcg taccagcagg ccagaaccag gctctataac | 600 |
| gagctcaatc taggacgaag agaggagtac gatgttttgg acaagagacg tggccgggac | 660 |
| cctgagatgg ggggaaagcc gagaaggaag aaccctcagg aaggcctgta caatgaactg | 720 |
| cagaaagata agatggcgga ggcctacagt gagattggga tgaaaggcga gcgccggagg | 780 |
| ggcaaggggc acgatggcct ttaccagggt ctcagtacag ccaccaagga cacctacgac | 840 |
| gcccttcaca tgcaggccct gccccctcgc taa | 873 |

<210> SEQ ID NO 8
<211> LENGTH: 969
<212> TYPE: DNA
<213> ORGANISM: Artificial Sequence
<220> FEATURE:
<223> OTHER INFORMATION: hinge domain V-3-4-5

<400> SEQUENCE: 8

| | |
|---|---|
| gactgcactc cagggtttca ctgcctgggg gcaggatgca gcatgtgtga acaggattgt | 60 |
| aaacaaggtc aagaactgac aaaaaaaggt tgtaaagact gttgctttgg gacatttaac | 120 |
| gatcagaaac gtggcatctg tcgaccctgg acaaactgtt cttttggatgg aaagtctgtg | 180 |
| cttgtgaatg ggacgaagga gagggacgtg gtctgtggac catctccagc cgacctctct | 240 |
| ccgggagcat cctctgtgac cccgcctgcc cctgcgagag agccaggaca ctctccgcag | 300 |
| ttttgggtgc tggtggtggt tggtggagtc ctggcttgct atagcttgct agtaacagtg | 360 |
| gcctttatta ttttctgggt gaggagtaag aggagcaggc tcctgcacag tgactacatg | 420 |
| aacatgactc cccgccgccc gggcccacc cgcaagcatt accagcccta tgccccacca | 480 |
| cgcgacttcg cagcctatcg ctccaaacgg gcagaaaga actcctgta tatattcaaa | 540 |
| caaccattta tgagaccagt acaaactact caagaggaag atggctgtag ctgccgattt | 600 |
| ccagaagaag aagaaggagg atgtgaactg agagtgaagt tcagcaggag cgcagagccc | 660 |
| cccgcgtacc agcagggcca gaaccagctc tataacgagc tcaatctagg acgaagagag | 720 |
| gagtacgatg ttttggacaa gagacgtggc cgggaccctg agatgggggg aaagccgaga | 780 |
| aggaagaacc ctcaggaagg cctgtacaat gaactgcaga agataagat ggcggaggcc | 840 |
| tacagtgaga ttgggatgaa aggcgagcgc cggaggggca aggggcacga tggcctttac | 900 |
| cagggtctca gtacagccac caaggacacc tacgacgccc ttcacatgca ggccctgccc | 960 |
| cctcgctaa | 969 |

<210> SEQ ID NO 9
<211> LENGTH: 1092
<212> TYPE: DNA
<213> ORGANISM: Artificial Sequence
<220> FEATURE:
<223> OTHER INFORMATION: hinge domain V-2-3-4-5

<400> SEQUENCE: 9

```
agtccctgtc ctccaaatag tttctccagc gcaggtggac aaaggacctg tgacatatgc    60
aggcagtgta aaggtgtttt caggaccagg aaggagtgtt cctccaccag caatgcagag   120
tgtgactgca ctccagggtt tcactgcctg ggggcaggat gcagcatgtg tgaacaggat   180
tgtaaacaag gtcaagaact gacaaaaaaa ggttgtaaag actgttgctt tgggacattt   240
aacgatcaga aacgtggcat ctgtcgaccc tggacaaact gttctttgga tggaaagtct   300
gtgcttgtga atgggacgaa ggagagggac gtggtctgtg gaccatctcc agccgacctc   360
tctccgggag catcctctgt gaccccgcct gcccctgcga gagagccagg acactctccg   420
cagttttggg tgctggtggt ggttggtgga gtcctggctt gctatagctt gctagtaaca   480
gtggccttta ttattttctg ggtgaggagt aagaggagca ggctcctgca cagtgactac   540
atgaacatga ctccccgccg ccccgggccc acccgcaagc attaccagcc ctatgcccca   600
ccacgcgact cgcagcctat cgctccaaa cggggcagaa agaaactcct gtatatattc   660
aaacaaccat ttatgagacc agtacaaact actcaagagg aagatggctg tagctgccga   720
tttccagaag aagaagaagg aggatgtgaa ctgagagtga agttcagcag gagcgcagag   780
ccccccgcgt accagcaggg ccagaaccag ctctataacg agctcaatct aggacgaaga   840
gaggagtacg atgttttgga caagagacgt ggccgggacc ctgagatggg gggaaagccg   900
agaaggaaga accctcagga aggcctgtac aatgaactgc agaaagataa gatggcggag   960
gcctacagtg agattgggat gaaaggcgag cgccggaggg caaggggca cgatggcctt  1020 taccagggtc tcagtacagc caccaaggac acctacgacg cccttcacat gcaggccctg  1080
ccccctcgct aa                                                      1092

<210> SEQ ID NO 10
<211> LENGTH: 1158
<212> TYPE: DNA
<213> ORGANISM: Artificial Sequence
<220> FEATURE:
<223> OTHER INFORMATION: hinge domain V-1-2-3-4-5

<400> SEQUENCE: 10
ttgcaggatc cttgtagtaa ctgcccagct ggtacattct gtgataataa caggaatcag    60
atttgcagtc cctgtcctcc aaatagtttc tccagcgcag gtggacaaag gacctgtgac   120
atatgcaggc agtgtaaagg tgttttcagg accaggaagg agtgttcctc caccagcaat   180
gcagagtgtg actgcactcc agggtttcac tgcctggggg caggatgcag catgtgtgaa   240
caggattgta acaaggtcaa gaactgacaa aaaaaggttg taaagactgt tgctttggga   300 catttaacg atcagaaacg tggcatctgt cgaccctgga caaactgttc tttggatgga   360
aagtctgtgc ttgtgaatgg gacgaaggag agggacgtgg tctgtggacc atctccagcc   420
gacctctctc cgggagcatc ctctgtgacc ccgcctgccc ctgcgagaga gccaggacac   480
tctccgcagt tttgggtgct ggtggtggtt ggtggagtcc tggcttgcta tagcttgcta   540
gtaacagtgg ccttttattat tttctgggtg aggagtaaga ggagcaggct cctgcacagt   600
gactacatga acatgactcc ccgccgcccc gggcccaccc gcaagcatta ccagccctat   660
gccccaccac gcgacttcgc agcctatcgc tccaaacggg gcagaaagaa actcctgtat   720
atattcaaac aaccatttat gagaccagta caaactactc aagaggaaga tggctgtagc   780
tgccgatttc cagaagaaga agaaggagga tgtgaactga gagtgaagtt cagcaggagc   840
gcagagcccc ccgcgtacca gcagggccag aaccagctct ataacgagct caatctagga   900
```

| cgaagagagg agtacgatgt tttggacaag agacgtggcc gggaccctga gatgggggga | 960 |
| aagccgagaa ggaagaaccc tcaggaaggc ctgtacaatg aactgcagaa agataagatg | 1020 |
| gcggaggcct acagtgagat tgggatgaaa ggcgagcgcc ggaggggcaa ggggcacgat | 1080 |
| ggcctttacc agggtctcag tacagccacc aaggacacct cgacgccct tcacatgcag | 1140 |
| gccctgcccc ctcgctaa | 1158 |

<210> SEQ ID NO 11
<211> LENGTH: 1527
<212> TYPE: DNA
<213> ORGANISM: Artificial Sequence
<220> FEATURE:
<223> OTHER INFORMATION: HER2-V 5

<400> SEQUENCE: 11

| atggattttc aggtgcagat tttcagcttc ctgctaatca gtgcctcagt cataatgtcc | 60 |
| agaggagata tccagatgac ccagtccccg agctccctgt ccgcctctgt gggcgatagg | 120 |
| gtcaccatca cctgccgtgc cagtcaggat gtgaatactg ctgtagcctg gtatcaacag | 180 |
| aaaccaggaa aagctccgaa actactgatt tactcggcat ccttccttta ttctggagtc | 240 |
| ccttctcgct tctctggatc tagatctggg acggatttca ctctgaccat cagcagtctg | 300 |
| cagccggaag acttcgcaac ttattactgt cagcaacatt atactactcc tcccacgttc | 360 |
| ggacagggta ccaaggtgga gatcaaaggt ggtggtggt ctggcggcgg cggctccgag | 420 |
| gttcagctgg tggagtctgg cggtggcctg gtgcagccag gggctcact ccgtttgtcc | 480 |
| tgtgcagctt ctggcttcaa cattaaagac acctatatac actgggtgcg tcaggccccg | 540 |
| ggtaagggcc tggaatgggt tgcaaggatt tatcctacga atggttatac tagatatgcc | 600 |
| gatagcgtca agggccgttt cactataagc gcagacacat ccaaaaacac agcctacctg | 660 |
| cagatgaaca gcctgcgtgc tgaggacact gccgtctatt attgttctag atggggaggg | 720 |
| gacggcttct atgctatgga cgtgtgggt caaggaaccc tggtcaccgt ctcctcgcca | 780 |
| tctccagccg acctctctcc gggagcatcc tctgtgaccc cgcctgcccc tgcgagagag | 840 |
| ccaggacact ctccgcagtt tgggtgctg gtggtggttg gtggagtcct ggcttgctat | 900 |
| agcttgctag taacagtggc ctttattatt ttctgggtga ggagtaagag gagcaggctc | 960 |
| ctgcacagtg actacatgaa catgactccc cgccgcccg ggcccacccg caagcattac | 1020 |
| cagccctatg ccccaccacg cgacttcgca gcctatcgct ccaaacgggg cagaaagaaa | 1080 |
| ctcctgtata tattcaaaca accatttatg agaccagtac aaactactca agaggaagat | 1140 |
| ggctgtagct gccgatttcc agaagaagaa gaaggaggat gtgaactgag agtgaagttc | 1200 |
| agcaggagcg cagagccccc cgcgtaccag cagggccaga accagctcta taacgagctc | 1260 |
| aatctaggac gaagagagga gtacgatgtt tttggacaaga gacgtggccg ggaccctgag | 1320 |
| atgggggggaa agccgagaag gaagaaccct caggaaggcc tgtacaatga actgcagaaa | 1380 |
| gataagatgg cggaggccta cagtgagatt gggatgaaag gcgagcgccg gagggcaag | 1440 |
| gggcacgatg gcctttacca gggtctcagt acagccacca aggacaccta cgacgccctt | 1500 |
| cacatgcagg ccctgccccc tcgctaa | 1527 |

<210> SEQ ID NO 12
<211> LENGTH: 1650
<212> TYPE: DNA
<213> ORGANISM: Artificial Sequence
<220> FEATURE:
<223> OTHER INFORMATION: HER2-V 4-5

<400> SEQUENCE: 12

```
atggattttc aggtgcagat tttcagcttc ctgctaatca gtgcctcagt cataatgtcc    60
agaggagata tccagatgac ccagtccccg agctccctgt ccgcctctgt gggcgatagg   120
gtcaccatca cctgccgtgc cagtcaggat gtgaatactg ctgtagcctg gtatcaacag   180
aaaccaggaa aagctccgaa actactgatt tactcggcat ccttccttta ttctggagtc   240
ccttctcgct ctctggatc tagatctggg acggatttca ctctgaccat cagcagtctg   300
cagccggaag acttcgcaac ttattactgt cagcaacatt atactactcc tcccacgttc   360
ggacagggta ccaaggtgga gatcaaaggt ggtggtggt ctggcggcgg cggctccgag   420
gttcagctgg tggagtctgg cggtggcctg gtgcagccag ggggctcact ccgtttgtcc   480
tgtgcagctt ctggcttcaa cattaaagac acctatatac actgggtgcg tcaggccccg   540
ggtaagggcc tggaatgggt tgcaaggatt tatcctacga atggttatac tagatatgcc   600
gatagcgtca agggccgttt cactataagc gcagacacat ccaaaaacac agcctacctg   660
cagatgaaca gcctgcgtgc tgaggacact gccgtctatt attgttctag atggggaggg   720
gacggcttct atgctatgga cgtgtggggt caaggaaccc tggtcaccgt ctcctcggac   780
tgttgctttg gacatttaa cgatcagaaa cgtggcatct gtcgaccctg acaaactgt   840
tctttggatg aaagtctgt gcttgtgaat gggacgaagg agaggacgt ggtctgtgga   900
ccatctccag ccgacctctc tccgggagca tcctctgtga ccccgcctgc cctgcgaga   960
gagccaggac actctccgca gttttgggtg ctggtggtgg ttggtggagt cctggcttgc  1020
tatagcttgc tagtaacagt ggcctttatt attttctggg tgaggagtaa gaggagcagg  1080
ctcctgcaca gtgactacat gaacatgact ccccgccgcc ccgggcccac ccgcaagcat  1140
taccagccct atgccccacc acgcgacttc gcagcctatc gctccaaacg gggcagaaag  1200
aaactcctgt atatattcaa caaccatttt atgagaccag tacaaactac tcaagaggaa  1260
gatggctgta gctgccgatt ccagaagaa gaagaaggag gatgtgaact gagagtgaag  1320
ttcagcagga cgcagagcc ccccgcgtac cagcagggcc agaaccagct ctataacgag  1380
ctcaatctag acgaagaga ggagtacgat gttttggaca gagacgtgg ccgggaccct  1440
gagatggggg gaaagccgag aaggaagaac cctcaggaag gcctgtacaa tgaactgcag  1500
aaagataaga tggcggaggc ctacagtgag attgggatga aggcgagcg ccggagggc  1560
aaggggcacg atggccttta ccagggtctc agtacagcca ccaaggacac ctacgacgcc  1620
cttcacatgc aggccctgcc ccctcgctaa                                  1650
```

<210> SEQ ID NO 13
<211> LENGTH: 1746
<212> TYPE: DNA
<213> ORGANISM: Artificial Sequence
<220> FEATURE:
<223> OTHER INFORMATION: HER2-V 3-4-5

<400> SEQUENCE: 13

```
atggattttc aggtgcagat tttcagcttc ctgctaatca gtgcctcagt cataatgtcc    60
agaggagata tccagatgac ccagtccccg agctccctgt ccgcctctgt gggcgatagg   120
gtcaccatca cctgccgtgc cagtcaggat gtgaatactg ctgtagcctg gtatcaacag   180
aaaccaggaa aagctccgaa actactgatt tactcggcat ccttccttta ttctggagtc   240
ccttctcgct ctctggatc tagatctggg acggatttca ctctgaccat cagcagtctg   300
```

| | |
|---|---|
| cagccggaag acttcgcaac ttattactgt cagcaacatt atactactcc tcccacgttc | 360 |
| ggacagggta ccaaggtgga gatcaaaggt ggtggtggtt ctggcggcgg cggctccgag | 420 |
| gttcagctgg tggagtctgg cggtggcctg gtgcagccag ggggctcact ccgtttgtcc | 480 |
| tgtgcagctt ctggcttcaa cattaaagac acctatatac actgggtgcg tcaggccccg | 540 |
| ggtaagggcc tggaatgggt tgcaaggatt tatcctacga atggttatac tagatatgcc | 600 |
| gatagcgtca agggccgttt cactataagc gcagacacat ccaaaaacac agcctacctg | 660 |
| cagatgaaca gcctgcgtgc tgaggacact gccgtctatt attgttctag atggggaggg | 720 |
| gacggcttct atgctatgga cgtgtggggt caaggaaccc tggtcaccgt ctcctcggac | 780 |
| tgcactccag ggtttcactg cctgggggca ggatgcagca tgtgtgaaca ggattgtaaa | 840 |
| caaggtcaag aactgacaaa aaaaggttgt aaagactgtt gctttgggac atttaacgat | 900 |
| cagaaacgtg gcatctgtcg accctggaca aactgttctt tggatggaaa gtctgtgctt | 960 |
| gtgaatggga cgaaggagag ggacgtggtc tgtggaccat ctccagccga cctctctccg | 1020 |
| ggagcatcct ctgtgacccc gcctgcccct gcgagagagc caggacactc tccgcagttt | 1080 |
| tgggtgctgg tggtggttgg tggagtcctg gcttgctata gcttgctagt aacagtggcc | 1140 |
| tttattattt tctgggtgag gagtaagagg agcaggctcc tgcacagtga ctacatgaac | 1200 |
| atgactcccc gccgccccgg gcccacccgc aagcattacc agccctatgc cccaccacgc | 1260 |
| gacttcgcag cctatcgctc caaacggggc agaaagaaac tcctgtatat attcaaacaa | 1320 |
| ccatttatga gaccagtaca aactactcaa gaggaagatg gctgtagctg ccgatttcca | 1380 |
| gaagaagaag aaggaggatg tgaactgaga gtgaagttca gcaggagcgc agagcccccc | 1440 |
| gcgtaccagc agggccagaa ccagctctat aacgagctca atctaggacg aagagaggag | 1500 |
| tacgatgttt tggacaagag acgtggccgg accctgaga tggggggaaa gccgagaagg | 1560 |
| aagaaccctc aggaaggcct gtacaatgaa ctgcagaaag ataagatggc ggaggcctac | 1620 |
| agtgagattg ggatgaaagg cgagcgccgg aggggcaagg gcacgatgg cctttaccag | 1680 |
| ggtctcagta cagccaccaa ggacacctac gacgcccttc acatgcaggc cctgcccct | 1740 |
| cgctaa | 1746 |

<210> SEQ ID NO 14
<211> LENGTH: 1869
<212> TYPE: DNA
<213> ORGANISM: Artificial Sequence
<220> FEATURE:
<223> OTHER INFORMATION: HER2-V 2-3-4-5

<400> SEQUENCE: 14

| | |
|---|---|
| atggattttc aggtgcagat tttcagcttc ctgctaatca gtgcctcagt cataatgtcc | 60 |
| agaggagata tccagatgac ccagtccccg agctccctgt ccgcctctgt gggcgatagg | 120 |
| gtcaccatca cctgccgtgc cagtcaggat gtgaatactg ctgtagcctg gtatcaacag | 180 |
| aaaccaggaa aagctccgaa actactgatt tactcggcat ccttccttta ttctggagtc | 240 |
| ccttctcgct tctctggatc tagatctggg acggatttca ctctgaccat cagcagtctg | 300 |
| cagccggaag acttcgcaac ttattactgt cagcaacatt atactactcc tcccacgttc | 360 |
| ggacagggta ccaaggtgga gatcaaaggt ggtggtggtt ctggcggcgg cggctccgag | 420 |
| gttcagctgg tggagtctgg cggtggcctg gtgcagccag ggggctcact ccgtttgtcc | 480 |
| tgtgcagctt ctggcttcaa cattaaagac acctatatac actgggtgcg tcaggccccg | 540 |
| ggtaagggcc tggaatgggt tgcaaggatt tatcctacga atggttatac tagatatgcc | 600 |

```
gatagcgtca agggccgttt cactataagc gcagacacat ccaaaaacac agcctacctg    660
cagatgaaca gcctgcgtgc tgaggacact gccgtctatt attgttctag atggggaggg    720
gacggcttct atgctatgga cgtgtggggt caaggaaccc tggtcaccgt ctcctcgagt    780
ccctgtcctc caaatagttt ctccagcgca ggtggacaaa ggacctgtga catatgcagg    840
cagtgtaaag gtgttttcag gaccaggaag gagtgttcct ccaccagcaa tgcagagtgt    900
gactgcactc cagggtttca ctgcctgggg gcaggatgca gcatgtgtga acaggattgt    960
aaacaaggtc aagaactgac aaaaaaaggt tgtaaagact gttgctttgg gacatttaac   1020
gatcagaaac gtggcatctg tcgaccctgg acaaactgtt ctttggatgg aaagtctgtg   1080
cttgtgaatg ggacgaagga gagggacgtg gtctgtggac catctccagc cgacctctct   1140
ccgggagcat cctctgtgac cccgcctgcc cctgcgagag agccaggaca ctctccgcag   1200 tttttgggtgc tggtggtggt tggtggagtc ctggcttgct atagcttgct agtaacagtg   1260
gcctttatta ttttctgggt gaggagtaag aggagcaggc tcctgcacag tgactacatg   1320
aacatgactc cccgccgccc cgggcccacc cgcaagcatt accagcccta tgccccacca   1380
cgcgacttcg cagcctatcg ctccaaacgg ggcagaaaga aactcctgta tatattcaaa   1440
caaccattta tgagaccagt acaaactact caagaggaag atggctgtag ctgccgattt   1500
ccagaagaag aagaaggagg atgtgaactg agagtgaagt tcagcaggag cgcagagccc   1560
cccgcgtacc agcagggcca gaaccagctc tataacgagc tcaatctagg acgaagagag   1620
gagtacgatg ttttggacaa gagacgtggc cgggaccctg agatgggggg aaagccgaga   1680
aggaagaacc ctcaggaagg cctgtacaat gaactgcaga agataagat ggcggaggcc    1740 tacagtgaga ttgggatgaa aggcgagcgc cggaggggca aggggcacga tggcctttac   1800
cagggtctca gtacagccac caaggacacc tacgacgccc ttcacatgca ggccctgccc   1860
cctcgctaa                                                          1869
```

<210> SEQ ID NO 15
<211> LENGTH: 1935
<212> TYPE: DNA
<213> ORGANISM: Artificial Sequence
<220> FEATURE:
<223> OTHER INFORMATION: HER2-V 1-2-3-4-5

<400> SEQUENCE: 15

```
atggattttc aggtgcagat tttcagcttc ctgctaatca gtgcctcagt cataatgtcc     60
agaggagata tccagatgac ccagtccccg agctccctgt ccgcctctgt gggcgatagg    120
gtcaccatca cctgccgtgc cagtcaggat gtgaatactg ctgtagcctg gtatcaacag    180
aaaccaggaa aagctccgaa actactgatt tactcggcat ccttccttta ttctggagtc    240
ccttctcgct tctctggatc tagatctggg acggatttca ctctgaccat cagcagtctg    300
cagccggaag acttcgcaac ttattactgt cagcaacatt atactactcc tcccacgttc    360
ggacagggta ccaaggtgga gatcaaaggt ggtggtggtt ctggcggcgg cggctccgag    420
gttcagctgg tggagtctgg cggtggcctg gtgcagccag gggctcact ccgtttgtcc     480 tgtgcagctt ctggcttcaa cattaaagac acctatatac actgggtgcg tcaggccccg    540
ggtaagggcc tggaatgggt tgcaaggatt tatcctacga atggttatac tagatatgcc    600
gatagcgtca agggccgttt cactataagc gcagacacat ccaaaaacac agcctacctg    660
cagatgaaca gcctgcgtgc tgaggacact gccgtctatt attgttctag atggggaggg    720
```

-continued

```
gacggcttct atgctatgga cgtgtggggt caaggaaccc tggtcaccgt ctcctcgttg      780
caggatcctt gtagtaactg cccagctggt acattctgtg ataataacag gaatcagatt      840
tgcagtccct gtcctccaaa tagtttctcc agcgcaggtg acaaaggac ctgtgacata       900 tgcaggcagt gtaaaggtgt tttcaggacc aggaaggagt gttcctccac cagcaatgca     960
gagtgtgact gcactccagg gtttcactgc ctgggggcag gatgcagcat gtgtgaacag    1020
gattgtaaac aaggtcaaga actgacaaaa aaaggttgta aagactgttg ctttgggaca    1080
tttaacgatc agaaacgtgg catctgtcga ccctggacaa actgttcttt ggatggaaag    1140
tctgtgcttg tgaatgggac gaaggagagg gacgtggtct gtggaccatc tccagccgac    1200
ctctctccgg gagcatcctc tgtgaccccg cctgcccctg cgagagagcc aggacactct    1260
ccgcagtttt gggtgctggt ggtggttggt ggagtcctgg cttgctatag cttgctagta    1320
acagtggcct ttattatttt ctgggtgagg agtaagagga gcaggctcct gcacagtgac    1380
tacatgaaca tgactccccg ccgcccgggg cccacccgca agcattacca gccctatgcc    1440
ccaccacgcg acttcgcagc ctatcgctcc aaacggggca gaaagaaact cctgtatata    1500
ttcaaacaac catttatgag accagtacaa actactcaag aggaagatgg ctgtagctgc    1560
cgatttccag aagaagaaga aggaggatgt gaactgagag tgaagttcag caggagcgca    1620
gagccccccg cgtaccagca gggccagaac cagctctata cgagctcaa tctaggacga     1680 agagaggagt acgatgtttt ggacaagaga cgtggccggg accctgagat ggggggaaag   1740
ccgagaagga gaaccctca ggaaggcctg tacaatgaac tgcagaaaga taagatggcg     1800
gaggcctaca gtgagattgg gatgaaaggc gagcgccgga ggggcaaggg gcacgatggc   1860
ctttaccagg gtctcagtac agccaccaag gacacctacg acgcccttca catgcaggcc   1920
ctgccccctc gctaa                                                    1935
```

<210> SEQ ID NO 16
<211> LENGTH: 1542
<212> TYPE: DNA
<213> ORGANISM: Artificial Sequence
<220> FEATURE:
<223> OTHER INFORMATION: CD19-V 5

<400> SEQUENCE: 16

```
atggattttc aggtgcagat tttcagcttc ctgctaatca gtgcctcagt cataatgtcc       60
agaggagaca tccagatgac acagactaca tcctcctgt ctgcctctct gggagacaga      120
gtcaccatca gttgcagggc aagtcaggac attagtaaat atttaaattg gtatcagcag     180
aaaccagatg gaactgttaa actcctgatc taccatacat caagattaca ctcaggagtc     240
ccatcaaggt tcagtggcag tgggtctgga acagattatt ctctcaccat tagcaacctg     300
gagcaagaag atattgccac ttacttttgc caacagggta atacgcttcc gtacacgttc     360
ggagggggga ccaagctgga gatcacaggt ggcggtggct cggcggtgg tgggtcgggt     420 ggcggcggat ctgaggtgaa actgcaggag tcaggacctg gcctggtggc gcctcacag     480 agcctgtccg tcacatgcac tgtctcaggg gtctcattac ccgactatgg tgtaagctgg    540
attcgccagc ctccacgaaa gggtctggag tggctgggaa taatatgggg tagtgaaacc   600
acatactata attcagctct caaatccaga ctgaccatca tcaaggacaa ctccaagagc   660
caagttttct aaaaatgaa cagtctgcaa actgatgaca cagccattta ctactgtgcc   720
aaacattatt actacggtgg tagctatgct atggactact gggggcaagg aacctcagtc   780
accgtctcct caccatctcc agccgacctc tctccgggag catcctctgt gacccccgcct   840
```

```
gcccctgcga gagagccagg acactctccg cagttttggg tgctggtggt ggttggtgga    900
gtcctggctt gctatagctt gctagtaaca gtggccttta ttattttctg ggtgaggagt    960
aagaggagca ggctcctgca cagtgactac atgaacatga ctccccgccg ccccgggccc   1020
acccgcaagc attaccagcc ctatgcccca ccacgcgact tcgcagccta tcgctccaaa   1080
cggggcagaa agaaactcct gtatatattc aaacaaccat ttatgagacc agtacaaact   1140
actcaagagg aagatggctg tagctgccga tttccagaag aagaagaagg aggatgtgaa   1200
ctgagagtga agttcagcag gagcgcagag ccccccgcgt accagcaggg ccagaaccag   1260
ctctataacg agctcaatct aggacgaaga gaggagtacg atgttttgga caagagacgt   1320
ggccgggacc ctgagatggg gggaaagccg agaaggaaga accctcagga aggcctgtac   1380
aatgaactgc agaaagataa gatggcggag gcctacagtg agattgggat gaaaggcgag   1440
cgccggaggg gcaaggggca cgatggcctt tacccagggtc tcagtacagc caccaaggac   1500
acctacgacg cccttcacat gcaggccctg cccctcgct aa                       1542
```

<210> SEQ ID NO 17
<211> LENGTH: 1665
<212> TYPE: DNA
<213> ORGANISM: Artificial Sequence
<220> FEATURE:
<223> OTHER INFORMATION: CD19-V 4-5

<400> SEQUENCE: 17

```
atggattttc aggtgcagat tttcagcttc ctgctaatca gtgcctcagt cataatgtcc     60
agaggagaca tccagatgac acagactaca tcctccctgt ctgcctctct gggagacaga    120
gtcaccatca gttgcagggc aagtcaggac attagtaaat atttaaattg gtatcagcag    180
aaaccagatg gaactgttaa actcctgatc taccatacat caagattaca ctcaggagtc    240
ccatcaaggt tcagtggcag tgggtctgga acagattatt ctctcaccat tagcaacctg    300
gagcaagaag atattgccac ttacttttgc caacagggta tacgcttcc gtacacgttc    360 ggaggggga ccaagctgga gatcacaggt ggcggtggct cgggcggtgg tgggtcgggt    420
ggcggcggat ctgaggtgaa actgcaggag tcaggacctg gcctggtggc gccctcacag    480
agcctgtccg tcacatgcac tgtctcaggg gtctcattac ccgactatgg tgtaagctgg    540
attcgccagc ctccacgaaa gggtctggag tggctgggag taatatgggg tagtgaaacc    600
acatactata attcagctct caaatccaga ctgaccatca tcaaggacaa ctccaagagc    660
caagttttct taaaaatgaa cagtctgcaa actgatgaca cagccattta ctactgtgcc    720
aaacattatt actacggtgg tagctatgct atggactact ggggccaagg aacctcagtc    780
accgtctcct cagactgttg ctttgggaca tttaacgatc agaaacgtgg catctgtcga    840
ccctggacaa actgttcttt ggatggaaag tctgtgcttg tgaatgggac gaaggagagg    900
gacgtggtct gtgaccatc tccagccgac ctctctccgg agcatcctc tgtgaccccg    960 cctgccctg cgagagagcc aggacactct ccgcagtttt gggtgctggt ggtggttggt   1020
ggagtcctgg cttgctatag cttgctagta acagtggcct ttattatttt ctgggtgagg   1080
agtaagagga gcaggctcct gcacagtgac tacatgaaca tgactccccg ccgcccggg   1140 cccacccgca agcattacca gccctatgcc ccaccacgcg acttcgcagc ctatcgctcc   1200
aaacggggca gaaagaaact cctgtatata ttcaaacaac catttatgag accagtacaa   1260
actactcaag aggaagatgg ctgtagctgc cgatttccag aagaagaaga aggaggatgt   1320
```

| | | |
|---|---|---|
| gaactgagag tgaagttcag caggagcgca gagcccccg cgtaccagca gggccagaac | 1380 |
| cagctctata cgagctcaa tctaggacga agagaggagt acgatgtttt ggacaagaga | 1440 |
| cgtggccggg accctgagat ggggggaaag ccgagaagga agaaccctca ggaaggcctg | 1500 |
| tacaatgaac tgcagaaaga taagatggcg gaggcctaca gtgagattgg gatgaaaggc | 1560 |
| gagcgccgga ggggcaaggg gcacgatggc ctttaccagg gtctcagtac agccaccaag | 1620 |
| gacacctacg acgcccttca catgcaggcc ctgccccctc gctaa | 1665 |

<210> SEQ ID NO 18
<211> LENGTH: 1761
<212> TYPE: DNA
<213> ORGANISM: Artificial Sequence
<220> FEATURE:
<223> OTHER INFORMATION: CD19-V 3-4-5

<400> SEQUENCE: 18

| | | |
|---|---|---|
| atggattttc aggtgcagat tttcagcttc ctgctaatca gtgcctcagt cataatgtcc | 60 |
| agaggagaca tccagatgac acagactaca tcctccctgt ctgcctctct gggagacaga | 120 |
| gtcaccatca gttgcagggc aagtcaggac attagtaaat atttaaattg gtatcagcag | 180 |
| aaaccagatg gaactgttaa actcctgatc taccatacat caagattaca ctcaggagtc | 240 |
| ccatcaaggt tcagtggcag tgggtctgga acagattatt ctctcaccat tagcaacctg | 300 |
| gagcaagaag atattgccac ttacttttgc caacagggta tacgcttcc gtacacgttc | 360 |
| ggagggggga ccaagctgga gatcacaggt ggcggtggct cgggcggtgg tgggtcgggt | 420 |
| ggcggcggat ctgaggtgaa actgcaggag tcaggacctg gcctggtggc gccctcacag | 480 |
| agcctgtccg tcacatgcac tgtctcaggg gtctcattac ccgactatgg tgtaagctgg | 540 |
| attcgccagc ctccacgaaa gggtctggag tggctgggag taatatgggg tagtgaaacc | 600 |
| acatactata attcagctct caaatccaga ctgaccatca tcaaggacaa ctccaagagc | 660 |
| caagttttct taaaaatgaa cagtctgcaa actgatgaca cagccattta ctactgtgcc | 720 |
| aaacattatt actacggtgg tagctatgct atggactact ggggccaagg aacctcagtc | 780 |
| accgtctcct cagactgcac tccagggttt cactgcctgg gggcaggatg cagcatgtgt | 840 |
| gaacaggatt gtaaacaagg tcaagaactg acaaaaaaag gttgtaaaga ctgttgcttt | 900 |
| gggacattta cgatcagaa acgtggcatc tgtcgaccct ggacaaactg ttctttggat | 960 |
| ggaaagtctg tgcttgtgaa tgggacgaag agagggacg tggtctgtgg accatctcca | 1020 |
| gccgacctct ctccgggagc atccctctgt acccgcctg cccctgcgag agagccagga | 1080 |
| cactctccgc agttttgggt gctggtggtg gttggtggag tcctggcttg ctatagcttg | 1140 |
| ctagtaacag tggccttat tattttctgg gtgaggagta agaggagcag gctcctgcac | 1200 |
| agtgactaca tgaacatgac tccccgccgc cccgggccca ccgcaagca ttaccagccc | 1260 |
| tatgccccac cacgcgactt cgcagcctat cgctccaaac ggggcagaaa gaaactcctg | 1320 |
| tatatattca acaaccatt tatgagacca gtacaaacta ctcaagagga gatggctgt | 1380 |
| agctgccgat ttccagaaga agaagaagga ggatgtgaac tgagagtgaa gttcagcagg | 1440 |
| agcgcagagc cccccgcgta ccagcagggc cagaaccagc tctataacga gctcaatcta | 1500 |
| ggacgaagag aggagtacga tgttttggac aagagacgtg gccgggaccc tgagatgggg | 1560 |
| ggaaagccga aggaagaa ccctcaggaa ggcctgtaca tgaactgca gaaagataag | 1620 |
| atggcggagg cctacagtga gattgggatg aaaggcgagc gccggagggg caaggggcac | 1680 |
| gatggccttt accagggtct cagtacagcc accaaggaca cctacgacgc ccttcacatg | 1740 |

```
<210> SEQ ID NO 19
<211> LENGTH: 1884
<212> TYPE: DNA
<213> ORGANISM: Artificial Sequence
<220> FEATURE:
<223> OTHER INFORMATION: CD19-V 2-3-4-5

<400> SEQUENCE: 19
```

| | | | | | |
|---|---|---|---|---|---|
| atggattttc | aggtgcagat | tttcagcttc | tgctaatca | gtgcctcagt | cataatgtcc | 60 |
| agaggagaca | tccagatgac | acagactaca | tcctccctgt | ctgcctctct | gggagacaga | 120 |
| gtcaccatca | gttgcagggc | aagtcaggac | attagtaaat | atttaaattg | gtatcagcag | 180 |
| aaaccagatg | gaactgttaa | actcctgatc | taccatacat | caagattaca | ctcaggagtc | 240 |
| ccatcaaggt | tcagtggcag | tgggtctgga | acagattatt | ctctcaccat | tagcaacctg | 300 |
| gagcaagaag | atattgccac | ttactttgc | aacagggta | atacgcttcc | gtacacgttc | 360 |
| ggagggggga | ccaagctgga | gatcacaggt | ggcggtggct | cgggcggtgg | tgggtcgggt | 420 |
| ggcggcggat | ctgaggtgaa | actgcaggag | tcaggacctg | gcctggtggc | gccctcacag | 480 |
| agcctgtccg | tcacatgcac | tgtctcaggg | gtctcattac | ccgactatgg | tgtaagctgg | 540 |
| attcgccagc | ctccacgaaa | gggtctggag | tggctgggag | taatatgggg | tagtgaaacc | 600 |
| acatactata | attcagctct | caaatccaga | ctgaccatca | tcaaggacaa | ctccaagagc | 660 |
| caagttttct | taaaaatgaa | cagtctgcaa | actgatgaca | cagccattta | ctactgtgcc | 720 |
| aaacattatt | actacggtgg | tagctatgct | atggactact | ggggccaagg | aacctcagtc | 780 |
| accgtctcct | caagtccctg | tcctccaaat | agtttctcca | cgcagaggtg | gcaaaggacc | 840 |
| tgtgacatat | gcaggcagtg | taaaggtgtt | ttcaggacca | ggaaggagtg | ttcctccacc | 900 |
| agcaatgcag | agtgtgactg | cactccaggg | tttcactgcc | tggggcagg | atgcagcatg | 960 |
| tgtgaacagg | attgtaaaca | aggtcaagaa | ctgacaaaaa | aaggttgtaa | agactgttgc | 1020 |
| tttgggacat | ttaacgatca | gaaacgtggc | atctgtcgac | cctggacaaa | ctgttctttg | 1080 |
| gatggaaagt | ctgtgcttgt | gaatgggacg | aaggagaggg | acgtggtctg | tggaccatct | 1140 |
| ccagccgacc | tctctccggg | agcatcctct | gtgaccccgc | tgcccctgc | gagagagcca | 1200 |
| ggacactctc | gcagttttg | ggtgctggtg | gtggttggtg | gagtcctggc | ttgctatagc | 1260 |
| ttgctagtaa | cagtggcctt | tattattttc | tgggtgagga | gtaagaggag | caggctcctg | 1320 |
| cacagtgact | acatgaacat | gactccccgc | cgccccgggc | ccacccgcaa | gcattaccag | 1380 |
| ccctatgccc | caccacgcga | cttcgcagcc | tatcgctcca | acgggcag | aaagaaactc | 1440 |
| ctgtatatat | tcaaacaacc | atttatgaga | ccagtacaaa | ctactcaaga | ggaagatggc | 1500 |
| tgtagctgcc | gatttccaga | agaagaagaa | ggaggatgtg | aactgagagt | gaagttcagc | 1560 |
| aggagcgcag | agccccccgc | gtaccagcag | ggccagaacc | agctctataa | cgagctcaat | 1620 |
| ctaggacgaa | gagaggagta | cgatgttttg | gacaagagac | gtggccggga | ccctgagatg | 1680 |
| gggggaaagc | cgagaaggaa | gaaccctcag | gaaggcctgt | acaatgaact | gcagaaagat | 1740 |
| aagatggcgg | aggcctacag | tgagattggg | atgaaaggcg | agcgccggag | gggcaagggg | 1800 |
| cacgatggcc | tttaccaggg | tctcagtaca | gccaccaagg | acacctacga | cgcccttcac | 1860 |
| atgcaggccc | tgccccctcg | ctaa | | | | 1884 |

```
<210> SEQ ID NO 20
```

<211> LENGTH: 1950
<212> TYPE: DNA
<213> ORGANISM: Artificial Sequence
<220> FEATURE:
<223> OTHER INFORMATION: CD19-V 1-2-3-4-5

<400> SEQUENCE: 20

| | | | | | |
|---|---|---|---|---|---|
| atggattttc | aggtgcagat | tttcagcttc | ctgctaatca | gtgcctcagt | cataatgtcc | 60 |
| agaggagaca | tccagatgac | acagactaca | tcctccctgt | ctgcctctct | gggagacaga | 120 |
| gtcaccatca | gttgcagggc | aagtcaggac | attagtaaat | atttaaattg | gtatcagcag | 180 |
| aaaccagatg | gaactgttaa | actcctgatc | taccatacat | caagattaca | ctcaggagtc | 240 |
| ccatcaaggt | tcagtggcag | tgggtctgga | acagattatt | ctctcaccat | tagcaacctg | 300 |
| gagcaagaag | atattgccac | ttactttttgc | caacagggta | atacgcttcc | gtacacgttc | 360 |
| ggaggggga | ccaagctgga | gatcacaggt | ggcggtggct | cgggcggtgg | tgggtcgggt | 420 |
| ggcggcggat | ctgaggtgaa | actgcaggag | tcaggacctg | gcctggtggc | gccctcacag | 480 |
| agcctgtccg | tcacatgcac | tgtctcaggg | gtctcattac | ccgactatgg | tgtaagctgg | 540 |
| attcgccagc | ctccacgaaa | gggtctggag | tggctgggag | taatatgggg | tagtgaaacc | 600 |
| acatactata | attcagctct | caaatccaga | ctgaccatca | tcaaggacaa | ctccaagagc | 660 |
| caagttttct | taaaaatgaa | cagtctgcaa | actgatgaca | cagccattta | ctactgtgcc | 720 |
| aaacattatt | actacggtgg | tagctatgct | atggactact | ggggccaagg | aacctcagtc | 780 |
| accgtctcct | cattgcagga | tccttgtagt | aactgcccag | ctggtacatt | ctgtgataat | 840 |
| aacaggaatc | agatttgcag | tccctgtcct | ccaaatagtt | tctccagcgc | aggtggacaa | 900 |
| aggacctgtg | acatatgcag | gcagtgtaaa | ggtgttttca | ggaccaggaa | ggagtgttcc | 960 |
| tccaccagca | atgcagagtg | tgactgcact | ccagggtttc | actgcctggg | ggcaggatgc | 1020 |
| agcatgtgtg | aacaggattg | taaacaaggt | caagaactga | caaaaaaagg | ttgtaaagac | 1080 |
| tgttgctttg | gacatttaa | cgatcagaaa | cgtggcatct | gtcgaccctg | acaaactgt | 1140 |
| tctttggatg | gaaagtctgt | gcttgtgaat | gggacgaagg | agagggacgt | ggtctgtgga | 1200 |
| ccatctccag | ccgacctctc | tccgggagca | tcctctgtga | cccgcctgc | ccctgcgaga | 1260 |
| gagccaggac | actctccgca | gttttgggtg | ctggtggtgg | ttggtggagt | cctggcttgc | 1320 |
| tatagcttgc | tagtaacagt | ggcctttatt | attttctggg | tgaggagtaa | gaggagcagg | 1380 |
| ctcctgcaca | gtgactacat | gaacatgact | ccccgccgcc | ccgggcccac | ccgcaagcat | 1440 |
| taccagcccct | atgccccacc | acgcgacttc | gcagcctatc | gctccaaacg | ggcagaaaag | 1500 |
| aaactcctgt | atatattcaa | acaaccattt | atgagaccag | tacaaactac | tcaagaggaa | 1560 |
| gatggctgta | gctgccgatt | tccagaagaa | gaagaaggag | gatgtgaact | gagagtgaag | 1620 |
| ttcagcagga | gcgcagagcc | ccccgcgtac | cagcagggcc | agaaccagct | ctataacgag | 1680 |
| ctcaatctag | gacgaagaga | ggagtacgat | gttttggaca | agagacgtgg | ccgggaccct | 1740 |
| gagatggggg | gaaagccgag | aaggaagaac | cctcaggaag | gcctgtacaa | tgaactgcag | 1800 |
| aaagataaga | tggcggaggc | ctacagtgag | attgggatga | aggcgagcg | ccggaggggc | 1860 |
| aagggcacg | atggccttta | ccagggtctc | agtacagcca | ccaaggacac | ctacgacgcc | 1920 |
| cttcacatgc | aggccctgcc | ccctcgctaa | | | | 1950 |

<210> SEQ ID NO 21
<211> LENGTH: 1530
<212> TYPE: DNA
<213> ORGANISM: Artificial Sequence

<220> FEATURE:
<223> OTHER INFORMATION: GPC3-V 5

<400> SEQUENCE: 21

| | | | | |
|---|---|---|---|---|
| atggattttc | aggtgcagat | tttcagcttc | ctgctaatca | gtgcctcagt cataatgtcc | 60 |
| agaggagatg | ttgtgatgac | tcagtctcca | ctctccctgc | ccgtcacccc tggagagccg | 120 |
| gcctccatct | cctgcagatc | tagtcagagc | cttgtacaca | gtaatgccaa cacctattta | 180 |
| cattggtacc | tgcagaagcc | agggcagtct | ccacagctcc | tgatctataa agtttccaac | 240 |
| cgattttctg | ggtccctga | caggttcagt | ggcagtggat | caggcacaga ttttacactg | 300 |
| aaaatcagca | gagtggaggc | tgaggatgtt | ggggtttatt | actgctctca aaatacacat | 360 |
| gttcctccta | cgtttggcca | ggggaccaag | ctggagatca | aacgtggtgg aggcggttca | 420 |
| ggcggaggtg | gctctcaggt | gcagctggtg | cagtctggag | ctgaggtgaa gaagcctggg | 480 |
| gcctcagtga | aggtctcctg | caaggcttct | ggatacacct | tcaccgacta tgaaatgcac | 540 |
| tgggtgcgac | aggcccctgg | acaagggctt | gagtggatgg | gagctcttga tcctaaaact | 600 |
| ggtgatactg | cctacagtca | gaagttcaag | ggcagagtca | cgctgaccgc ggacgaatcc | 660 |
| acgagcacag | cctacatgga | gctgagcagc | ctgagatctg | aggacacggc cgtgtattac | 720 |
| tgtacaagat | tctactccta | tacttactgg | ggccagggaa | ccctggtcac cgtctcctca | 780 |
| ccatctccag | ccgacctctc | tccgggagca | tcctctgtga | cccgcctgc ccctgcgaga | 840 |
| gagccaggac | actctccgca | gttttgggtg | ctggtggtgg | ttggtggagt cctggcttgc | 900 |
| tatagcttgc | tagtaacagt | ggcctttatt | attttctggg | tgaggagtaa gaggagcagg | 960 |
| ctcctgcaca | gtgactacat | gaacatgact | ccccgccgcc | cgggcccac ccgcaagcat | 1020 |
| taccagcccct | atgccccacc | acgcgacttc | gcagcctatc | gctccaaacg gggcagaaag | 1080 |
| aaactcctgt | atatattcaa | acaaccattt | atgagaccag | tacaaactac tcaagaggaa | 1140 |
| gatggctgta | gctgccgatt | ccagaagaa | aagaaggag | gatgtgaact gagagtgaag | 1200 |
| ttcagcagga | gcgcagagcc | ccccgcgtac | cagcagggcc | agaaccagct ctataacgag | 1260 |
| ctcaatctag | gacgaagaga | ggagtacgat | gttttggaca | agagacgtgg ccggacccct | 1320 |
| gagatggggg | gaaagccgag | aaggaagaac | cctcaggaag | cctgtacaa tgaactgcag | 1380 |
| aaagataaga | tggcggaggc | ctacagtgag | attgggatga | aggcgagcg ccggaggggc | 1440 |
| aagggcacg | atgcctttta | ccagggtctc | agtacagcca | ccaaggacac ctacgacgcc | 1500 |
| cttcacatgc | aggccctgcc | ccctcgctaa | | | 1530 |

<210> SEQ ID NO 22
<211> LENGTH: 1653
<212> TYPE: DNA
<213> ORGANISM: Artificial Sequence
<220> FEATURE:
<223> OTHER INFORMATION: GPC3-V 4-5

<400> SEQUENCE: 22

| | | | | |
|---|---|---|---|---|
| atggattttc | aggtgcagat | tttcagcttc | ctgctaatca | gtgcctcagt cataatgtcc | 60 |
| agaggagatg | ttgtgatgac | tcagtctcca | ctctccctgc | ccgtcacccc tggagagccg | 120 |
| gcctccatct | cctgcagatc | tagtcagagc | cttgtacaca | gtaatgccaa cacctattta | 180 |
| cattggtacc | tgcagaagcc | agggcagtct | ccacagctcc | tgatctataa agtttccaac | 240 |
| cgattttctg | ggtccctga | caggttcagt | ggcagtggat | caggcacaga ttttacactg | 300 |
| aaaatcagca | gagtggaggc | tgaggatgtt | ggggtttatt | actgctctca aaatacacat | 360 |

-continued

```
gttcctccta cgtttggcca ggggaccaag ctggagatca aacgtggtgg aggcggttca      420
ggcggaggtg gctctcaggt gcagctggtg cagtctggag ctgaggtgaa gaagcctggg      480
gcctcagtga aggtctcctg caaggcttct ggatacacct tcaccgacta tgaaatgcac      540
tgggtgcgac aggcccctgg acaagggctt gagtggatgg gagctcttga tcctaaaact      600
ggtgatactg cctacagtca gaagttcaag ggcagagtca cgctgaccgc ggacgaatcc      660
acgagcacag cctacatgga gctgagcagc ctgagatctg aggacacggc cgtgtattac      720
tgtacaagat tctactccta tacttactgg ggccagggaa ccctggtcac cgtctcctca      780
gactgttgct ttgggacatt aacgatcag aaacgtggca tctgtcgacc ctggacaaac      840
tgttctttgg atggaaagtc tgtgcttgtg aatgggacga aggagaggga cgtggtctgt      900
ggaccatctc cagccgacct ctctccggga gcatcctctg tgaccccgcc tgcccctgcg      960
agagagccag acactctccg cagttttgg gtgctggtgg tggttggtgg agtcctggct     1020
tgctatagct tgctagtaac agtggccttt attattttct gggtgaggag taagaggagc     1080
aggctcctgc acagtgacta catgaacatg actccccgcc gcccccgggcc cacccgcaag     1140 cattaccagc cctatgcccc accacgcgac ttcgcagcct atcgctccaa cggggcaga     1200 aagaaactcc tgtatatatt caacaacca tttatgagac agtacaaac tactcaagag     1260 gaagatggct gtagctgccg atttccagaa gaagaagaag aggatgtga actgagagtg     1320 aagttcagca ggagcgcaga gccccccgcg taccagcagg gccagaacca gctctataac     1380
gagctcaatc taggacgaag agaggagtac gatgttttgg acaagagacg tggccgggac     1440
cctgagatgg ggggaaagcc gagaaggaag aaccctcagg aaggcctgta caatgaactg     1500
cagaaagata agatggcgga ggcctacagt gagattggga tgaaaggcga gcgccggagg     1560
ggcaaggggc acgatggcct ttaccagggt ctcagtacag ccaccaagga cacctacgac     1620
gcccttcaca tgcaggccct gccccctcgc taa                                  1653
```

<210> SEQ ID NO 23
<211> LENGTH: 1749
<212> TYPE: DNA
<213> ORGANISM: Artificial Sequence
<220> FEATURE:
<223> OTHER INFORMATION: GPC3-V 3-4-5

<400> SEQUENCE: 23

```
atggattttc aggtgcagat tttcagcttc ctgctaatca gtgcctcagt cataatgtcc       60
agaggagatg ttgtgatgac tcagtctcca ctctccctgc ccgtcacccc tggagagccg      120
gcctccatct cctgcagatc tagtcagagc cttgtacaca gtaatgccaa cacctattta      180
cattggtacc tgcagaagcc agggcagtct ccacagctcc tgatctataa agtttccaac      240
cgattttctg gggtccctga caggttcagt ggcagtggat caggcacaga ttttacactg      300
aaaatcagca gagtggaggc tgaggatgtt ggggtttatt actgctctca aaatacacat      360
gttcctccta cgtttggcca ggggaccaag ctggagatca aacgtggtgg aggcggttca      420
ggcggaggtg gctctcaggt gcagctggtg cagtctggag ctgaggtgaa gaagcctggg      480
gcctcagtga aggtctcctg caaggcttct ggatacacct tcaccgacta tgaaatgcac      540
tgggtgcgac aggcccctgg acaagggctt gagtggatgg gagctcttga tcctaaaact      600
ggtgatactg cctacagtca gaagttcaag ggcagagtca cgctgaccgc ggacgaatcc      660
acgagcacag cctacatgga gctgagcagc ctgagatctg aggacacggc cgtgtattac      720
tgtacaagat tctactccta tacttactgg ggccagggaa ccctggtcac cgtctcctca      780
```

```
gactgcactc cagggtttca ctgcctgggg gcaggatgca gcatgtgtga acaggattgt    840
aaacaaggtc aagaactgac aaaaaaaggt tgtaaagact gttgctttgg gacatttaac    900
gatcagaaac gtggcatctg tcgaccctgg acaaactgtt ctttggatgg aaagtctgtg    960
cttgtgaatg ggacgaagga gagggacgtg gtctgtggac catctccagc cgacctctct   1020
ccgggagcat cctctgtgac cccgcctgcc cctgcgagag agccaggaca ctctccgcag   1080
ttttgggtgc tggtggtggt tggtggagtc ctggcttgct atagcttgct agtaacagtg   1140
gcctttatta ttttctgggt gaggagtaag aggagcaggc tcctgcacag tgactacatg   1200
aacatgactc cccgccgccc cgggcccacc cgcaagcatt accagcccta tgccccacca   1260
cgcgacttcg cagcctatcg ctccaaacgg ggcagaaaga aactcctgta tatattcaaa   1320
caaccattta tgagaccagt acaaactact caagaggaag atggctgtag ctgccgattt   1380
ccagaagaag aagaaggagg atgtgaactg agagtgaagt tcagcaggag cgcagagccc   1440
cccgcgtacc agcagggcca gaaccagctc tataacgagc tcaatctagg acgaagagag   1500
gagtacgatg tttggacaa gagacgtggc cgggaccctg agatgggggg aaagccgaga   1560
aggaagaacc ctcaggaagg cctgtacaat gaactgcaga agataagat ggcggaggcc    1620
tacagtgaga ttgggatgaa aggcgagcgc cggaggggca aggggcacga tggcctttac   1680
cagggtctca gtacagccac caaggacacc tacgacgccc ttcacatgca ggccctgccc   1740
cctcgctaa                                                           1749

<210> SEQ ID NO 24
<211> LENGTH: 1872
<212> TYPE: DNA
<213> ORGANISM: Artificial Sequence
<220> FEATURE:
<223> OTHER INFORMATION: GPC3-V 2-3-4-5

<400> SEQUENCE: 24
atggattttc aggtgcagat tttcagcttc ctgctaatca gtgcctcagt cataatgtcc     60
agaggagatg ttgtgatgac tcagtctcca ctctccctgc ccgtcacccc tggagagccg    120
gcctccatct cctgcagatc tagtcagagc cttgtacaca gtaatgccaa cacctattta    180
cattggtacc tgcagaagcc agggcagtct ccacagctcc tgatctataa agtttccaac    240
cgattttctg ggtccctga caggttcagt ggcagtggat caggcacaga ttttacactg    300
aaaatcagca gtgtggaggc tgaggatgtt ggggtttatt actgctctca aaatacacat    360
gttcctccta cgtttggcca ggggaccaag ctggagatca acgtggtgg aggcggttca    420
ggcggaggtg gctctcaggt gcagctggtg cagtctggag ctgaggtgaa gaagcctggg    480
gcctcagtga aggtctcctg caaggcttct ggatacacct tcaccgacta tgaaatgcac    540
tgggtgcgac aggcccctgg acaagggctt gagtggatgg agctcttga tcctaaaact    600
ggtgatactg cctacagtca gaagttcaag ggcagagtca cgctgaccgc ggacgaatcc    660
acgagcacag cctacatgga gctgagcagc ctgagatctg aggacacggc cgtgtattac    720
tgtacaagat tctactccta tacttactgg ggccagggaa ccctggtcac cgtctcctca    780
agtccctgtc ctccaaatag tttctccagc gcaggtggac aaaggacctg tgacatatgc    840
aggcagtgta aggtgttttt caggaccagg aaggagtgtt cctccaccag caatgcagag    900
tgtgactgca ctccagggtt tcactgcctg ggggcaggat gcagcatgtg tgaacaggat    960
tgtaaacaag gtcaagaact gacaaaaaaa ggttgtaaag actgttgctt tgggacattt   1020
```

| | |
|---|---|
| aacgatcaga aacgtggcat ctgtcgaccc tggacaaact gttctttgga tggaaagtct | 1080 |
| gtgcttgtga atgggacgaa ggagagggac gtggtctgtg gaccatctcc agccgacctc | 1140 |
| tctccgggag catcctctgt gaccccgcct gcccctgcga gagagccagg acactctccg | 1200 |
| cagttttggg tgctggtggt ggttggtgga gtcctggctt gctatagctt gctagtaaca | 1260 |
| gtggccttta ttattttctg ggtgaggagt aagaggagca ggctcctgca cagtgactac | 1320 |
| atgaacatga ctccccgccg ccccgggccc acccgcaagc attaccagcc ctatgcccca | 1380 |
| ccacgcgact tcgcagccta tcgctccaaa cggggcagaa agaaactcct gtatatattc | 1440 |
| aaacaaccat ttatgagacc agtacaaact actcaagagg aagatggctg tagctgccga | 1500 |
| tttccagaag aagaagaagg aggatgtgaa ctgagagtga agttcagcag gagcgcagag | 1560 |
| ccccccgcgt accagcaggg ccagaaccag ctctataacg agctcaatct aggacgaaga | 1620 |
| gaggagtacg atgttttgga caagagacgt ggccgggacc ctgagatggg gggaaagccg | 1680 |
| agaaggaaga accctcagga aggcctgtac aatgaactgc agaaagataa gatggcggag | 1740 |
| gcctacagtg agattgggat gaaaggcgag cgccggaggg caaggggca cgatggcctt | 1800 |
| taccagggtc tcagtacagc caccaaggac acctacgacg cccttcacat gcaggccctg | 1860 |
| ccccctcgct aa | 1872 |

<210> SEQ ID NO 25
<211> LENGTH: 1938
<212> TYPE: DNA
<213> ORGANISM: Artificial Sequence
<220> FEATURE:
<223> OTHER INFORMATION: GPC3-V 1-2-3-4-5

<400> SEQUENCE: 25

| | |
|---|---|
| atggatttc aggtgcagat tttcagcttc ctgctaatca gtgcctcagt cataatgtcc | 60 |
| agaggagatg ttgtgatgac tcagtctcca ctctccctgc ccgtcacccc tggagagccg | 120 |
| gcctccatct cctgcagatc tagtcagagc cttgtacaca gtaatgccaa cacctattta | 180 |
| cattggtacc tgcagaagcc agggcagtct ccacagctcc tgatctataa agtttccaac | 240 |
| cgattttctg ggtccctga caggttcagt ggcagtggat caggcacaga ttttacactg | 300 |
| aaaatcagca gagtggaggc tgaggatgtt ggggtttatt actgctctca aaatacacat | 360 |
| gttcctccta cgtttggcca ggggaccaag ctggagatca acgtggtgg aggcggttca | 420 |
| ggcggaggtg gctctcaggt gcagctggtg cagtctggag ctgaggtgaa gaagcctggg | 480 |
| gcctcagtga aggtctcctg caaggcttct ggatacaccct tcaccgacta tgaaatgcac | 540 |
| tgggtgcgac aggcccctgg acaagggctt gagtggatgg gagctcttga tcctaaaact | 600 |
| ggtgatactg cctacagtca gaagttcaag ggcagagtca cgctgaccgc ggacgaatcc | 660 |
| acgagcacag cctacatgga gctgagcagc ctgagatctg aggacacggc cgtgtattac | 720 |
| tgtacaagat tctactccta tacttactgg ggccagggaa ccctggtcac cgtctcctca | 780 |
| ttgcaggatc cttgtagtaa ctgcccagct ggtacattct gtgataataa caggaatcag | 840 |
| atttgcagtc cctgtcctcc aaatagtttc tccagcgcag gtggacaaag gacctgtgac | 900 |
| atatgcaggc agtgtaaagg tgttttcagg accaggaagg agtgttcctc caccagcaat | 960 |
| gcagagtgtg actgcactcc agggttcac tgcctggggg caggatgcag catgtgtgaa | 1020 |
| caggattgta acaaggtca agaactgaca aaaaaggtt gtaaagactg ttgctttggg | 1080 |
| acatttaacg atcagaaacg tggcatctgt cgaccctgga caaactgttc tttgatgga | 1140 |
| aagtctgtgc ttgtgaatgg gacgaaggag agggacgtgg tctgtggacc atctccagcc | 1200 |

```
gacctctctc cgggagcatc ctctgtgacc ccgcctgccc ctgcgagaga gccaggacac   1260
tctccgcagt tttgggtgct ggtggtggtt ggtggagtcc tggcttgcta tagcttgcta   1320
gtaacagtgg cctttattat tttctgggtg aggagtaaga ggagcaggct cctgcacagt   1380
gactacatga acatgactcc ccgccgcccc gggcccaccc gcaagcatta ccagccctat   1440
gccccaccac gcgacttcgc agcctatcgc tccaaacggg gcagaaagaa actcctgtat   1500
atattcaaac aaccatttat gagaccagta caaactactc aagaggaaga tggctgtagc   1560
tgccgatttc agaagaaga agaaggagga tgtgaactga gagtgaagtt cagcaggagc   1620
gcagagcccc ccgcgtacca gcagggccag aaccagctct ataacgagct caatctagga   1680
cgaagagagg agtacgatgt tttggacaag agacgtggcc gggaccctga tgggggga    1740 aagccgagaa ggaagaaccc tcaggaaggc ctgtacaatg aactcagaa agataagatg   1800 gcggaggcct acagtgagat tgggatgaaa ggcgagcgcc ggaggggcaa ggggcacgat   1860
ggcctttacc agggtctcag tacagccacc aaggacacct cgacgccct tcacatgcag    1920 gccctgcccc ctcgctaa                                                 1938

<210> SEQ ID NO 26
<211> LENGTH: 777
<212> TYPE: DNA
<213> ORGANISM: Artificial Sequence
<220> FEATURE:
<223> OTHER INFORMATION: HER2

<400> SEQUENCE: 26
atggattttc aggtgcagat tttcagcttc ctgctaatca gtgcctcagt cataatgtcc     60
agaggagata tccagatgac ccagtccccg agctccctgt ccgcctctgt gggcgatagg    120
gtcaccatca cctgccgtgc cagtcaggat gtgaatactg ctgtagcctg gtatcaacag    180
aaaccaggaa aagctccgaa actactgatt tactcggcat ccttccttta ttctggagtc    240
ccttctcgct tctctggatc tagatctggg acggatttca ctctgaccat cagcagtctg    300
cagccggaag acttcgcaac ttattactgt cagcaacatt atactactcc tcccacgttc    360
ggacagggta ccaaggtgga gatcaaaggt ggtggtggtt ctggcggcgg cggctccgag    420
gttcagctgg tggagtctgg cggtggcctg gtgcagccag ggggctcact ccgtttgtcc    480
tgtgcagctt ctggcttcaa cattaaagac acctatatac actgggtgcg tcaggccccg    540
ggtaagggcc tggaatgggt tgcaaggatt tatcctacga atggttatac tagatatgcc    600
gatagcgtca agggccgttt cactataagc gcagacacat ccaaaaacac agcctacctg    660
cagatgaaca gcctgcgtgc tgaggacact gccgtctatt attgttctag atggggaggg    720
gacggcttct atgctatgga cgtgtggggt caaggaaccc tggtcaccgt ctcctcg       777

<210> SEQ ID NO 27
<211> LENGTH: 778
<212> TYPE: DNA
<213> ORGANISM: Artificial Sequence
<220> FEATURE:
<223> OTHER INFORMATION: GPC3

<400> SEQUENCE: 27
atggattttc aggtgcagat tttcagcttc ctgctaatca gtgcctcagt cataatgtcc     60
agaggagatg ttgtgatgac tcagtctcca ctctccctgc ccgtcacccc tggagagccg    120
gcctcctctc ctgcagatct agtcagagcc ttgtacacag taatgccaac acctatttac    180
```

```
attggtacct gcagaagcca gggcagtctc cacagctcct gatctataaa gtttccaacc      240
gattttctgg ggtccctgac aggttcagtg gcagtggatc aggcacagat tttacactga      300
aaatcagcag agtggaggct gaggatgttg gggtttatta ctgctctcaa aatacacatg      360
ttcctcctac gtttggccag gggaccaagc tggagatcaa acgtgtggag gcggttcagg      420
cggaggtggc tctcaggtgc agctggtgca gtctggagct gaggtgaaga agcctggggc      480
ctcagtgaag gtctcctgca aggcttctgg atacaccttc accgactatg aaatgcactg      540
ggtgcgacag gcccctggac aagggcttga gtggatggga gctcttgatc ctaaaactgg      600
tgatactgcc tacagtcaga gttcaaggg  cagagtcacg ctgaccgcgg acgaatccac      660
gagcacagcc tacatggagc tgagcagcct gagatctgag gacacggccg tgtattactg      720
tacaagattc tactcctata cttactgggg ccagggaacc ctggtcaccg tctcctca       778
```

```
<210> SEQ ID NO 28
<211> LENGTH: 792
<212> TYPE: DNA
<213> ORGANISM: Artificial Sequence
<220> FEATURE:
<223> OTHER INFORMATION: CD19

<400> SEQUENCE: 28
atggattttc aggtgcagat tttcagcttc ctgctaatca gtgcctcagt cataatgtcc      60
agaggagaca tccagatgac acagactaca tcctccctgt ctgcctctct gggagacaga      120
gtcaccatca gttgcagggc aagtcaggac attagtaaat atttaaattg gtatcagcag      180
aaaccagatg gaactgttaa actcctgatc taccatacat caagattaca ctcaggagtc      240
ccatcaaggt tcagtggcag tgggtctgga acagattatt ctctcaccat tagcaacctg      300
gagcaagaag atattgccac ttactttgc  aacagggta atacgcttcc gtacacgttc      360
ggagggggga ccaagctgga gatcacaggt ggcggtggct cggcggtgg tgggtcgggt      420 ggcggcggat ctgaggtgaa actgcaggag tcaggacctg gcctggtggc gccctcacag      480
agcctgtccg tcacatgcac tgtctcaggg gtctcattac ccgactatgg tgtaagctgg      540
attcgccagc ctccacgaaa gggtctggag tggctgggag taatatgggg tagtgaaacc      600
acatactata attcagctct caaatccaga ctgaccatca tcaaggacaa ctccaagagc      660 caagtttttct aaaaatgaa cagtctgcaa actgatgaca cagccattta ctactgtgcc      720
aaacattatt actacggtgg tagctatgct atggactact ggggccaagg aacctcagtc      780
accgtctcct ca                                                          792
```

```
<210> SEQ ID NO 29
<211> LENGTH: 135
<212> TYPE: DNA
<213> ORGANISM: Artificial Sequence
<220> FEATURE:
<223> OTHER INFORMATION: hinge domain

<400> SEQUENCE: 29
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg      120
gacttcgcct gtgat                                                       135
```

```
<210> SEQ ID NO 30
<211> LENGTH: 135
<212> TYPE: DNA
<213> ORGANISM: Artificial Sequence
```

```
<220> FEATURE:
<223> OTHER INFORMATION: hinge domain

<400> SEQUENCE: 30
gatatttact tctgcaaaat tgaagttatg tatcctcctc cttacctaga caatgagaag      60
agcaatggaa ccattatcca tgtgaaaggg aaacaccttt gtccaagtcc cctatttccc     120
ggaccttcta agccc                                                     135

<210> SEQ ID NO 31
<211> LENGTH: 316
<212> TYPE: DNA
<213> ORGANISM: Artificial Sequence
<220> FEATURE:
<223> OTHER INFORMATION: hinge domain

<400> SEQUENCE: 31
taaagccaaa gggcagcccc gagaaccaca ggtgtacacc ctgcccccat cccgggatga      60
gctgaccaag aaccaggtca gcctgacctg cctggtcaaa ggcttctatc ccagcgacat     120
cgccgtggag tgggagagca atgggcagcc ggagaacaac tacaagacca cgcctcccgt     180
gctggactcc gacggctcct tcttcctcta cagcaagctc accgtggaca agagcaggtg     240
gcagcagggg aacgtcttct catgctccgt gatgcatgag gctctgcaca accactacac     300
gcagaagagc ctctcc                                                    316
```